United States Patent
Reigan et al.

(10) Patent No.: US 12,220,415 B2
(45) Date of Patent: Feb. 11, 2025

(54) WEE1 KINASE INHIBITORS AND METHODS OF TREATING CANCER USING THE SAME

(71) Applicant: The Regents of the University of Colorado, A Body Corporate, Denver, CO (US)

(72) Inventors: Philip Reigan, Denver, CO (US); Donald S. Backos, Aurora, CO (US); Christopher J. Matheson, Denver, CO (US); Kimberly A. Casalvieri, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 16/975,818

(22) PCT Filed: Feb. 28, 2019

(86) PCT No.: PCT/US2019/019936
§ 371 (c)(1),
(2) Date: Aug. 26, 2020

(87) PCT Pub. No.: WO2019/169065
PCT Pub. Date: Sep. 6, 2019

(65) Prior Publication Data
US 2020/0405723 A1 Dec. 31, 2020

Related U.S. Application Data

(60) Provisional application No. 62/636,831, filed on Feb. 28, 2018.

(51) Int. Cl.
*A61K 31/519* (2006.01)
*A61K 31/635* (2006.01)
*A61K 31/704* (2006.01)
*A61K 31/7068* (2006.01)
*A61K 33/243* (2019.01)
*A61P 35/02* (2006.01)

(52) U.S. Cl.
CPC .......... *A61K 31/519* (2013.01); *A61K 31/635* (2013.01); *A61K 31/704* (2013.01); *A61K 31/7068* (2013.01); *A61K 33/243* (2019.01); *A61P 35/02* (2018.01)

(58) Field of Classification Search
None
See application file for complete search history.

(56) References Cited

U.S. PATENT DOCUMENTS

| 8,791,125 B2* | 7/2014 | Sagara | A61K 31/4162 |
| | | | 514/262.1 |
| 9,073,916 B2* | 7/2015 | Smaill | A61K 31/519 |
| 10,947,238 B2* | 3/2021 | Reigan | C07D 487/04 |
| 2007/0254892 A1* | 11/2007 | Sagara | A61P 35/00 |
| | | | 514/262.1 |
| 2016/0031877 A1 | 2/2016 | Smaill et al. | |
| 2020/0017528 A1 | 1/2020 | Qian et al. | |

FOREIGN PATENT DOCUMENTS

| GB | 884151 A | 12/1961 |
| JP | 2013503859 A | 2/2013 |
| JP | 2020505356 A | 2/2020 |
| JP | 2020510630 A | 4/2020 |
| JP | 2020529993 A | 10/2020 |
| WO | WO-2006091737 A1 | 8/2006 |
| WO | WO 2007/126122 A1 | 11/2007 |
| WO | WO-2007126128 A1 | 11/2007 |
| WO | WO 2015/092431 A1 | 6/2015 |
| WO | WO 2017/075629 A2 | 5/2017 |
| WO | WO-2018133829 A1 | 7/2018 |
| WO | WO-2019028008 A1 * | 2/2019 ........... A61K 31/519 |
| WO | WO-2019169065 A2 | 9/2019 |

OTHER PUBLICATIONS

A WEE1 Inhibitor Analog of AZD1775 Maintains Synergy with Cisplatin and Demonstrates Reduced Single-Agent Cytotoxicity in Medulloblastoma Cells Matheson et al. ACS Chem. Biol. 2016, 11, 921-930 (Year: 2016).*
Bridges K.A. et al. "MK-1775, a Novel Wee1 Kinase Inhibitor, Radiosensitizes p53-Defective Human Tumor Cells", Clinical Cancer Research 2011,17(17):5638-5648.
Bucher N. et al. "G2 checkpoint abrogation and checkpoint kinase-1 targeting in the treatment of cancer", British Journal of Cancer, 2008, 98(3):523-528.
Chen T. et al. "Targeting the S and G2 checkpoint to treat cancer", Drug Discovery Today, 2012; 17(5-6):194-202.
De Witt Hamer P.C. et al. "WEE1 Kinase Targeting Combined with DNA-Damaging Cancer Therapy Catalyzes Mitotic Catastrophe", Clinical Cancer Research, 2011,17(13):4200-4207.

(Continued)

Primary Examiner — Jeffrey S Lundgren
Assistant Examiner — Eric Tran
(74) Attorney, Agent, or Firm — Snell & Wilmer L.L.P.

(57) ABSTRACT

A compound, or a pharmaceutically acceptable salts or prodrugs thereof, having the chemical structure:

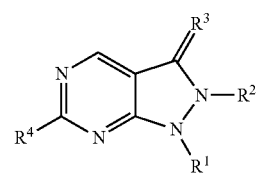

and methods of using these compounds to inhibit WEE1 kinase and treat cancer in a subject.

15 Claims, 4 Drawing Sheets

(56) References Cited

OTHER PUBLICATIONS

Do K. et al. "Wee1 kinase as a target for cancer therapy", Cell Cycle, 2013, 12(19):3159-3164.
Forte S. et al. "Gene Expression Analysis of PTEN Positive Glioblastoma Stem Cells Identifies DUB3 and Wee1 Modulation in a Cell Differentiation Model", PLoS One 2013, 8(12):e81432.
Harris E.S. et al. "Integrated genomic analysis identifies the mitotic checkpoint kinase WEE1 as a novel therapeutic target in medulloblastoma", Molecular Cancer, 2014, 13:72.
Hirai H. et al. "Small-molecule inhibition of Wee1 kinase by MK-1775 selectively sensitizes p53-deficient tumor cells to DNA-damaging agents", Molecular Cancer Therapy, 2009, 8(11):2992-3000.
Hirai H. et al. "MK-1775, a small molecule Wee1 inhibitor, enhances anti-tumor efficacy of various DNAdamaging agents, including 5-fluorouracil", 2010, 9(7):514-522.
Igarashi M et al. "Wee1+-like gene in human cells", Letters to Nature, 1991, 353(6339):80-83.
Indovina P. et al. "Targeting the checkpoint kinase WEE1: Selective sensitization of cancer cells to DNA-damaging drugs", Cancer Biology & Therapy, 2010 9(7):523-525.
Jin P. et al. "Role of Inhibitory CDC2 Phosphorylation in Radiation-induced G2 Arrest in Human Cells", The Journal of Cell Biology, 1996,134(4):963-970.
Leijen S et al. "Abrogation of the G2 Checkpoint by Inhibition of Wee-1 Kinase Results in Sensitization of p53-Deficient Tumor Cells to DNA-Damaging Agents", Current Clinical Pharmacology, 2010, 5(3):186-191.
McGowan C. H. et al. "Human Wee1 kinase inhibits cell division by phosphorylating p34cdc2 exclusively on Tyr15", The EMBO Journal, 1993, 12(1):75-85.
Mir S.E. et al. "In Silico Analysis of Kinase Expression Identifies WEE1 as a Gatekeeper against Mitotic Catastrophe in Glioblastoma", Cancer Cell, 2010, 18(3):244-257.
O'Conner, LJ et al., "Efficient synthesis of 2-nitroimidazole derivatives and the bioreductive clinical candidate Evofosfamide (TH-302)", Organic Chemistry Frontiers 2015, 2, pp. 1-4 (1026-1029).
Orgogozo et al. "Thedifferentialviewofgenotype—phenotyperelationships", Frontiers in Genetics, Hypothesis and Theory, 2015, 6:70.
Parker L. L. et al. "Inactivation of the p34cdc2-Cyclin B Complex by the Human WEE1 Tyrosine Kinase", Science, 1992, 257(5078):1955-1957.
Tanabe, K. et al., "Current molecular design of intelligent drugs and imaging probes targeting tumor-specific microenvironments", Organic & Biomolecular Chemistry, 2007, 5:3745-3757.
Tercel, M. et al., "Hypoxia-Selective Antitumor Agents. 16. Nitroarylmethyl Quaternary Salts—as Bioreductive Prodrugs of the Alkylating Agent Mechlorethamine", Journal of Medicinal Chemistry, 2001, 44(21): 3511-3522.
Tuel-Ahlgren et al. "Role of Tyrosine Phosphorylation in Radiation—Induced Cell Cycle—Arrest of Leukemic B-Cell Precursors at the G2-M Transition Checkpoint", Leukemia & Lymphoma 1996, 20(5-6):417-426.
Wang et al. "Global Profiling of Signaling Networks: Study of Breast Cancer Stem Cells and Potential Regulation", The Oncologist, 2011, 16(7):966-979.
Zhou et al. "A regimen combining the Wee1 inhibitor AZD1775 with HDAC inhibitors targets human acute myeloid leukemia cells harboring various genetic mutations", Leukemia, 2015, 29(4):807-818.
Van Linden et al. "Inhibition of Wee1 Sensitizes Cancer Cells to Antimetabolite Chemotherapeutics In Vitro and In Vivo, Independent of p53 Functionality", Molecular Cancer Therapeutics, 2013, 12(12):2675-2684.
Matheson C. J. et al. "Development of Potent Pyrazolopyrimidinone-Based WEE1 Inhibitors with Limited Single-Agent Cytotoxicity for Cancer Therapy", ChemMedChem Communications, vol. 13, No. 16, 2018, pp. 1681-1694.
Hauser et al., "Pyrazolono (3, 4-d) pyrimidines. II. 6-Methylpyrazolono (3, 4-d) pyrimidines and Some Reactions of Pyrazolono (3, 4-d) pyrimidines1, 2". The Journal of Organic Chemistry. Feb. 1961; 26(2): 451-5.
Shen et al., "3-aminopyrazolopyrazine Derivatives as Spleen Tyrosine Kinase Inhibitors," Chemical Biology & Drug Design. Nov. 2016; 88(5): 690-8.
Office Action dated Jan. 24, 2024 in Australian Patent Application No. 2019227823.
Office Action dated Oct. 30, 2023 in Japanese Patent Application No. 2020-545351.
Office Action dated Apr. 4, 2024 in Canadian Patent Application No. 3,088,997.

\* cited by examiner

WEE1 KINASE INHIBITORS AND METHODS OF TREATING CANCER USING THE SAME

CROSS REFERENCE TO RELATED APPLICATION

This application is a U.S. National Phase application, filed under U.S.C. § 371, of International Application No. PCT/US2019/019936, filed Feb. 28, 2019, which claims the benefit of U.S. Provisional Patent Application Ser. No. 62/636,831, filed Feb. 28, 2018, the entire contents of each of which are incorporated herein by reference in their entireties.

GOVERNMENT INTEREST

This invention was made with Government support under grant number R21NS084084 awarded by the National Institutes of Health (NIH). The U.S. Government has certain rights in this invention.

TECHNICAL FIELD

The invention relates to improvements in cancer chemotherapy.

BACKGROUND OF DISCLOSURE

Cell cycle checkpoints are surveillance mechanisms that monitor and coordinate the order and fidelity of cell cycle events. When defects in the division program of a cell are detected, checkpoints prevent the pursuant cell cycle transition through regulation of the relevant cyclin-cdk complexes. Checkpoints that respond to DNA damage have been described for the G1, S and G2 phases of the cell cycle. For example, the p53 tumor suppressor is a key regulator of G1/S checkpoints, and can promote cell cycle delay or apoptosis in response to DNA damage. Cancer cells that possess a deficient G1 checkpoint, which impairs the ability of the cell to halt the cell cycle in order to repair DNA damage prior to replication, gives these cancer cells a means to accumulate mutations and propagate irregularities that are favorable to cancer formation. These cancer cells are therefore reliant on the G2 checkpoint to prevent excessive DNA damage that leads to apoptosis via mitotic catastrophe (Chen T, et al. Drug Discovery Today. 2012; 17(5-6):194-202; Bucher N, et al., British Journal of Cancer. 2008; 98(3):523-8). In normal cells, the G1 checkpoint is not compromised; therefore, the G2 checkpoint is not burdened with halting the cell cycle prior to DNA damage repair. Thus, modulation of the G2 checkpoint selectively impacts tumorigenesis rather than normal cell growth.

WEE1 is a tyrosine kinase that is a critical component of the ataxia-telangiectasia-mutated-and-Rad3-related (ATR)-mediated G2 cell cycle checkpoint control that prevents entry into mitosis in response to cellular DNA damage (Do K, et al., Cell Cycle. 2013; 12(19):3159-64). ATR phosphorylates and activates CHK1, which in turn activates WEE1, leading to the selective phosphorylation of cyclin-dependent kinase 1 (CDK1) at Tyr15 (Parker L L, et al., Science. 1992; 257(5078):1955-7; McGowan C H, et al., The EMBO Journal. 1993; 12(1):75-85), thereby stabilizing the CDK1-cyclin B complex and halting cell-cycle progression (Indovina P, et al., Cancer Biol. Ther. 9(7):523-5; Jin P, et al., J Cell Biol. 1996; 134(4):963-70). This process confers a survival advantage by allowing tumor cells time to repair damaged DNA prior to entering mitosis (Igarashi M, et al., 1991; 353(6339):80-3). Inhibition of WEE1 abrogates the G2 checkpoint, forcing cancer cells with DNA damage to enter into unscheduled mitosis and undergo cell death via mitotic catastrophe (De Witt Hamer P C, et al., Clin Cancer Res. 2011; 17(13):4200-7; Hirai H, et al., Mol Cancer Ther. 2009; 8(11):2992-3000; Hirai H, et al., 2010; 9(7):514-22; Indovina P, et al., Cancer biology & therapy. 2010; 9(7): 523-5; Leijen S, et al. Current clinical pharmacology. 2010; 5(3):186-91. Mir S E, et al., Cancer Cell. 2010; 18(3):244-57; Bridges K, et al., Clinical cancer research 2011; 17(17): 5638-48).

SUMMARY

One aspect of this disclosure provides a compound, or a pharmaceutically acceptable salt or prodrug thereof, having a chemical structure of formula (I):

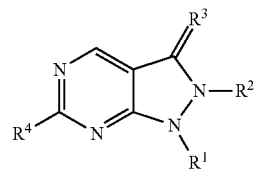

wherein:

$R^1$ is $C_{1-6}$ alkyl, aryl, or heteroaryl, that are optionally mono-, di-, or tri-substituted with $C_{1-6}$alkyl, $C_{2-6}$alkenyl, hydroxy, amino, amide, carboxylic acid, carboxylate ester, carbamate, hydrazide, hydroxamate, guanidino acetate, guanidine acetate esters, glycinate, or a combination thereof;

$R^2$ is H, $C_{1-6}$ alkyl, $C_{2-6}$ alkenyl, $C_{1-6}$ alkoxy, or $C_{1-6}$ alkyl optionally substituted with $C_{1-6}$ alkyl, hydroxy, amino, amide, carboxylic acid, carboxylate ester, aryl, substituted aryl, heteroaryl, or substituted heteroaryl;

$R^3$ is O, S, NH, $N^+HR^5$ wherein $R^5$ is substituted or unsubstituted $C_{1-6}$ alkyl;

$R^4$ is $OR^6$ or $R^4$ is $NR^7R^8$ wherein $R^6$ is H, $C_{1-6}$ alkyl, $C_{3-8}$ cycloalkyl, benzamidyl, heterocycloalkyl, aryl or heteroaryl that are optionally mono-, di-, or tri-substituted with $C_{1-6}$ alkyl, $C_{2-6}$ alkenyl, hydroxy, amino, amide, carboxylic acid, carboxylate ester, $C_{1-6}$alkylamino, ($C_{1-6}$ alkylamino)$C_{1-6}$alkyl, ($C_{1-6}$alkylamino)$C_{1-6}$alkoxy, benzamidyl, heterocycloalkyl, substituted heterocycloalkyl, aryl, substituted aryl, heteroaryl, or substituted heteroaryl, or a combination thereof; and, wherein $R^7$ and $R^8$ are independently H, $C_{1-6}$alkyl, $C_{3-8}$ cycloalkyl, benzamidyl, heterocycloalkyl, aryl or heteroaryl that are optionally mono-, di-, or tri-substituted with $C_{1-6}$alkyl, $C_{2-6}$alkenyl, hydroxy, amino, amide, carboxylic acid, carboxylate ester, $C_{1-6}$ alkylamino, ($C_{1-6}$alkylamino)$C_{1-6}$alkyl, ($C_{1-6}$alkylamino)$C_{1-6}$alkoxy, benzamidyl, heterocycloalkyl, substituted heterocycloalkyl, aryl, substituted aryl, heteroaryl, or substituted heteroaryl, or a combination thereof.

Another aspect of this disclosure provides pharmaceutical compositions comprising at least one WEE1 inhibitor compound of this disclosure and at least one pharmaceutically acceptable additive.

Another aspect of this disclosure provides pharmaceutical kits containing a pharmaceutical composition of this disclosure, prescribing information for the composition, and a container.

Another aspect of this disclosure provides methods for inhibiting WEE1 kinase activity in a subject, including administering to the subject a therapeutically effective amount of a WEE1 inhibitor compound of this disclosure, or a pharmaceutically acceptable salt thereof.

This disclosure also provides methods of preventing, treating, or ameliorating cancer, or preventing metastasis of a cancer in a subject, including administering a therapeutically-effective amount of a compound of this disclosure that inhibits WEE1 kinase to a subject in need thereof. In these methods, the cancer may be an advanced solid tumor, a blood cancer (including, for example, acute myeloid leukemia), a brain tumor, an ovarian tumor, cervical cancer, squamous cell cancer of the head and neck, pancreatic cancer, and lung cancer.

In these methods, the WEE1 inhibitor compound may be administered to the subject within a pharmaceutical composition. The pharmaceutical composition may be a monophasic pharmaceutical composition suitable for parenteral or oral administration consisting essentially of a therapeutically-effective amount of the WEE1 inhibitor compound, and a pharmaceutically acceptable additive.

In these methods, the pharmaceutical composition may be administered in combination with one or more DNA-targeted agents, including DNA alkylating agents and topoisomerase inhibitors, including cisplatin, capecitabine, carboplatin, cyclophosphamide, cytarabine, dauoribicin, docetaxel, doxorubicin, 5-fluorouracil, gemcitabine, methotrexate, paclitaxel, premetrexed, irinotecan temozolomide, topotecan, radiation, or combinations thereof.

In these methods, the pharmaceutical composition may be administered in combination with at least one of cisplatin, cytarabine, temozolomide, doxorubicin, Bcl-2 inhibitors (such as ABT199), or combinations of these compounds.

In related aspects, this disclosure also provides the use of a WEE1 inhibitor compound of this disclosure, or a pharmaceutically acceptable salt thereof, in the manufacture of a medicament for the treatment of cancer. Similarly, this disclosure provides a WEE1 inhibitor compound of this disclosure, or a pharmaceutically acceptable salt thereof, for use in the treatment of cancer.

This Summary is neither intended nor should it be construed as being representative of the full extent and scope of the present invention. Moreover, references made herein to "the present disclosure," or aspects thereof, should be understood to mean certain embodiments of the present invention and should not necessarily be construed as limiting all embodiments to a particular description. The present invention is set forth in various levels of detail in this Summary as well as in the attached drawings and the Detailed Description and no limitation as to the scope of the present invention is intended by either the inclusion or non-inclusion of elements, components, etc. in this Summary. Additional aspects of the present disclosure will become readily apparent from the Description of Embodiments, particularly when taken together with the drawings.

BRIEF DESCRIPTION OF DRAWINGS

FIG. 1A is a dose-response study for ONS-76 cells treated with a concentration range of WEE1 inhibitors for 72 hours in an MTS assay. AZD1775 inhibits cellular metabolic viability most potently (EC50=159±31 nM), with CM181 (EC50=203±40 nM) and KAC034 (EC50=252±9 nM) displaying comparable results. Limited effects were observed for other inhibitors within the series (n=3, error bars/ ±=S.D.). FIG. 1B is a dose-response study for Daoy cells treated with a concentration range of WEE1 inhibitors for 72 hours in an MTS assay. AZD1775 (EC50=179±16 nM) exhibits significantly more potent effects on cellular metabolic viability than CM181 (81% activity at 600 nM) and KAC034 (84% activity at 600 nM). No other analogs displayed any reduction in MTS signal up to 600 nM inhibitor dose (n=3, error bars/±=S.D.).

FIG. 2B shows the results of a quantitative ELISA determination of pCDK1(Tyr15) levels in Daoy cell lysates (0.05 mg/mL total protein) after treatment for 24 hours with a single 220 nM dose of all active WEE1 inhibitors. A decrease in pCDK1 concentration when compared to DMSO control was observed for AZD1775, KAC034, and CM181, whereas the decrease in pCDK1 upon treatment with CM169 was statistically the same as that for AZD1775 (n=3, error bars=S.D., compared with DMSO; *=$p<0.05$, =$p<0.01$, *=$p<0.001$; compared to AZD1775; n.s.=no significance). FIG. 2B shows pCDK1(Tyr15) ELISA dose response for Daoy cell lysates (0.05 mg/mL total protein) after treatment for 24 hours with AZD1775, KAC034, CM181, and CM169 (n=3, error bars/±=S.D.).

DETAILED DESCRIPTION

Figure 1A:
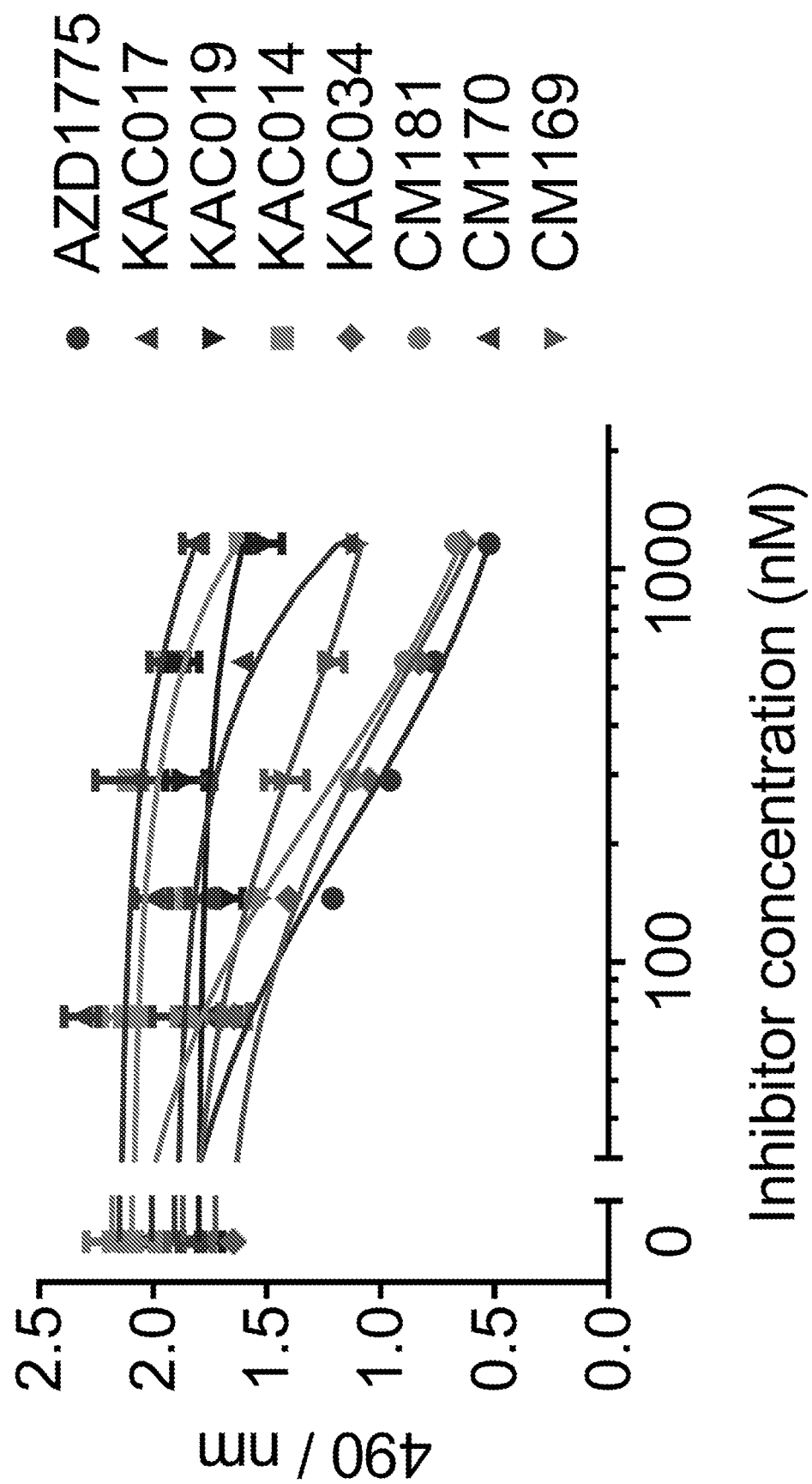
FIGS. 1A and 1B show the effects of WEE1 inhibitors of this disclosure on cell viability in medulloblastoma cells.

The present disclosure is drawn to WEE1 kinase inhibitors with significantly improved WEE1 kinase selectivity and/or inhibitory potency that demonstrate low cytotoxicity and synergy with standard chemotherapy in the treatment of patients with advanced solid tumors or blood cancers.

To facilitate an understanding of the embodiments presented, the following definitions are provided.

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

"Administration of" and "administering a" compound or agent should be understood to mean providing a compound or agent, a prodrug of a compound or agent, or a pharmaceutical composition as described herein. The compound, agent or composition can be administered by another person to the subject (e.g., intravenously) or it can be self-administered by the subject (e.g., tablets or capsules).

The terms "subject" and "individual" refers to mammals (for example, humans and veterinary animals such as dogs, cats, pigs, horses, sheep, and cattle).

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, amino groups, amido groups, carboxylate groups, halogens, and aryl groups.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, nitro, sulfate, carboxy, aryloxy, aryl, arylalkyl, amino, alkylamino, dialkylamino, (dialkylamino)alkyl, (dialkylamino)alkoxy, benzamidyl, or other R-groups.

"Acyl" refers to a group having the structure RCO—, where R may be alkyl, or substituted alkyl. "Lower acyl" groups are those that contain one to six carbon atoms.

"Acyloxy refers to a group having the structure RCOO—, where R may be alkyl or substituted alkyl. "Lower acyloxy" groups contain one to six carbon atoms.

"Alkenyl" refers to a cyclic, branched or straight chain group containing only carbon and hydrogen, and unless otherwise mentioned typically contains one to twelve carbon atoms and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, isobutyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_2-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$ alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms and contains one or more triple bonds. Alkynyl groups may be unsubstituted or substituted. "Lower alkynyl" groups are those that contain one to six carbon atoms.

The term "halogen" refers to fluoro, bromo, chloro, and iodo substituents.

"Aryl" refers to a monovalent unsaturated aromatic carbocyclic group having a single ring (e.g., phenyl or benzyl) or multiple condensed rings (e.g., naphthyl or anthryl), which can optionally be unsubstituted or substituted.

The term "heterocyclic" refers to ring structures containing one or more N, O, or, S atom(s) and can be saturated heterocycloalkyl (e.g., morpholino, piperidino, piperazinyl, 4-acetylpiperazinylphenyl, or pyrrolidinyl) or unsaturated heteroaryl (e.g., pyridyl, pyrimidyl, imidazolyl, oxazolyl, or thiazolyl) ring systems.

The term "amino" refers to an R-group having the structure —$NH_2$, which can be optionally substituted with, for example, lower alkyl groups, to yield an amino group having the general structure —NHR or —$NR_2$.

"Nitro" refers to an R-group having the structure —$NO_2$.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically un-hybridized p-orbitals.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid, and the like.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine, and the like.

Some of the compounds described herein may also exist in their tautomeric form.

A "therapeutically effective amount" of the disclosed compounds is a dosage of the compound that is sufficient to achieve a desired therapeutic effect, such as promotion of cell cycle, mitotic catastrophe, promotion of apoptosis, inhibition of angiogenesis, or an anti-tumor or anti-metastatic effect, inhibition of TNF-alpha activity, inhibition of immune cytokines, or treatment of a neurodegenerative disease. In some examples, a therapeutically effective amount is an amount sufficient to achieve tissue concentrations at the site of action that are similar to those that are shown to modulate angiogenesis, TNF-alpha activity, or immune cytokines, in tissue culture, in vitro, or in vivo. For example, a therapeutically effective amount of a compound may be such that the subject receives a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day.

The term "stereoisomer" refers to a molecule that is an enantiomer, diasteromer, or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

The term "modulate" refers to the ability of a disclosed compound to alter the amount, degree, or rate of a biological function, the progression of a disease, or amelioration of a condition. For example, modulating can refer to the ability of a compound to elicit an increase or decrease in angiogenesis, to inhibit TNF-alpha activity, or to inhibit tumor metastasis or tumorigenesis.

The term "angiogenic activity" refers to the ability of a disclosed compound or a particular concentration of a disclosed compound to stimulate angiogenesis. Angiogenic activity may be detected in vivo or in vitro. Angiogenic compounds or angiogenic concentrations of disclosed compounds stimulate angiogenesis, and such compounds and/or concentrations may be readily identified by those of ordinary skill in the art, using, for example, the methods described in the Examples that follow.

The term "anti-angiogenic activity" refers to the ability of a compound or a particular concentration of a disclosed compound to inhibit angiogenesis. Anti-angiogenic activity may be detected in vivo or in vitro. Anti-angiogenic or anti-angiogenic concentrations of disclosed compounds inhibit angiogenesis, and such compounds and/or concentrations may be readily identified by those of ordinary skill in the art, using, for example, the methods described in the Examples that follow.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactically administering a composition to a subject who does not exhibit signs of a disease or exhibits only early signs of the disease, for the purpose of decreasing the risk of developing a pathology or condition, or diminishing the severity of a pathology or condition.

As used herein, a "prodrug" is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability, and are readily metabolized into the active WEE1 inhibitors in vivo. Prodrugs of compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999. In general, protecting groups are removed under conditions which will not affect the remaining portion of the molecule. These methods are well known in the art and include acid hydrolysis, hydrogenolysis, and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers. Thus, these compounds can exist in different stereoisomeric forms. Accordingly, compounds and compositions may be provided as individual pure enantiomers or as stereoisomeric mixtures, including racemic mixtures. The compounds disclosed herein may be synthesized in, or are purified to be in, substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is itself substituted (e.g. substituted aryl). In some embodiments, the number of substituted groups linked together is limited to two (e.g. substituted alkyl is substituted with substituted aryl, wherein the substituent present on the aryl is not further substituted). In exemplary embodiments, a substituted group is not substituted with another substituted group (e.g. substituted alkyl is substituted with unsubstituted aryl).

One aspect of this disclosure are compounds that inhibit WEE1 kinase enzymes with significantly improved specificity for WEE1 kinase and can therefore be used to treat a wide variety of advanced solid tumors and blood cancers. Pharmaceutically acceptable salts, prodrugs, stereoisomers, and metabolites of all the WEE1 inhibitor compounds of this disclosure also are contemplated.

An aspect of this disclosure provides compounds, or pharmaceutically acceptable salts thereof, having the following chemical structure:

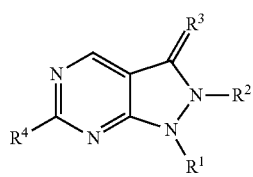

wherein:

$R^1$ is $C_{1-6}$ alkyl, aryl, or heteroaryl, that can be optionally mono-, di-, or tri-substituted with $C_{1-6}$alkyl, $C_{2-6}$alkenyl, hydroxy, amino, amide, carboxylic acid, carboxylate ester, carbamate, hydrazide, hydroxamate, guanidino acetate, guanidine acetate esters, glycinate, or a combination thereof;

$R^2$ is H, $C_{1-6}$ alkyl, $C_{2-6}$ alkenyl, $C_{1-6}$ alkoxy, or $C_{1-6}$ alkyl optionally substituted with $C_{1-6}$ alkyl, hydroxy, amino, amide, carboxylic acid, carboxylate ester, aryl, substituted aryl, heteroaryl, or substituted heteroaryl;

$R^3$ is O, S, NH, $N^+HR^5$ wherein $R^5$ is substituted or unsubstituted $C_{1-6}$ alkyl;

$R^4$ is $OR^6$ or $R^4$ is $NR^7R^8$ wherein $R^6$ is H, $C_{1-6}$ alkyl, $C_{3-8}$ cycloalkyl, benzamidyl, heterocycloalkyl, aryl or heteroaryl that are optionally mono-, di-, or tri-substituted with $C_{1-6}$ alkyl, $C_{2-6}$ alkenyl, hydroxy, amino, amide, carboxylic acid, carboxylate ester, $C_{1-6}$alkylamino, ($C_{1-6}$ alkylamino)$C_{1-6}$alkyl, ($C_{1-6}$alkylamino)$C_{1-6}$alkoxy, benzamidyl, heterocycloalkyl, substituted heterocycloalkyl, aryl, substituted aryl, heteroaryl, or substituted heteroaryl, or a combination thereof;

wherein $R^7$ and $R^8$ are independently H, $C_{1-6}$alkyl, $C_{3-8}$ cycloalkyl, benzamidyl, heterocycloalkyl, aryl or heteroaryl that are optionally mono-, di-, or tri-substituted with $C_{1-6}$alkyl, $C_{2-6}$alkenyl, hydroxy, amino, amide, carboxylic acid, carboxylate ester, $C_{1-6}$ alkylamino, ($C_{1-6}$alkylamino)$C_{1-6}$alkyl, ($C_{1-6}$alkylamino)$C_{1-6}$alkoxy, benzamidyl, heterocycloalkyl, substituted heterocycloalkyl, aryl, substituted aryl, heteroaryl, or substituted heteroaryl, or a combination thereof;

Within exemplary compounds of this disclosure, $R^1$ may be phenyl, pyridinyl, 3-(2-hydroxypropan-2-yl)phenyl, 6-(hydroxymethyl)pyridin-2-yl, 6-(2-hydroxypropan-2-yl)pyridin-2-yl optionally substituted with $C_{1-6}$alkyl, $C_{2-6}$alkenyl, hydroxy, amino, amide, carboxylic acid, carboxylate ester, carbamate, hydrazide, hydroxamate, guanidino acetate, guanidine acetate esters, glycinate, or a combination thereof.

Within exemplary compounds of this disclosure, $R^2$ may be H, $C_{1-6}$alkyl, $C_{2-6}$ alkenyl, $C_{1-6}$alkoxy, or $C_{1-6}$alkyl optionally substituted with $C_{1-6}$alkyl, hydroxy, amino, amide, carboxylic acid, carboxylate ester, aryl, substituted aryl, heteroaryl, substituted heteroaryl, or combinations thereof. Within exemplary compounds of this disclosure, $R^3$ may be O, S, NH, $N^+HR^5$ wherein $R^5$ is substituted or unsubstituted $C_{1-6}$alkyl.

Within exemplary compounds of this disclosure, $R^4$ may be $NR^7R^8$ wherein $R^7$ and $R^8$ are independently H, $C_{1-8}$ alkyl, substituted $C_{1-8}$alkyl, $C_{3-8}$ cycloalkyl, $C_{2-4}$ alkenyl, aryl such as a phenyl or benzyl, substituted aryl such as a methoxybenzyl, dialkylaminophenyl, ((dialkylamino)alkyl)phenyl, N,N-dialkylbenzamide, (dialkylamino)alkyl)phenyl, (dialkylamino)alkoxy)phenyl, piperazinylphenyl, 4-aklylpiperazin-1-yl)phenyl, (4-acylpiperazin-1-yl)phenyl, heteroaryl, substituted heteroaryl, or combinations thereof.

Within exemplary compounds of this disclosure, $R^7$ and $R^8$ may independently be a substituted phenyl such as 4-(2-(dimethylamino)ethyl)phenyl-, but when $R^1$ is 6-(2-hydroxy-2-propanyl)-2-pyridinyl or $R^2$ is allyl, $R^6$ and $R^7$ cannot independently be 4-(1-piperidinyl)phenyl-, 4-(4-morpholinyl)phenyl-, 4-(1-piperazinyl)phenyl-, or substituted 4-(1-piperazinyl)phenyl-, such as 4-(4-methyl-1-piperazinyl)phenyl.

Illustrative compounds of this disclosure include:
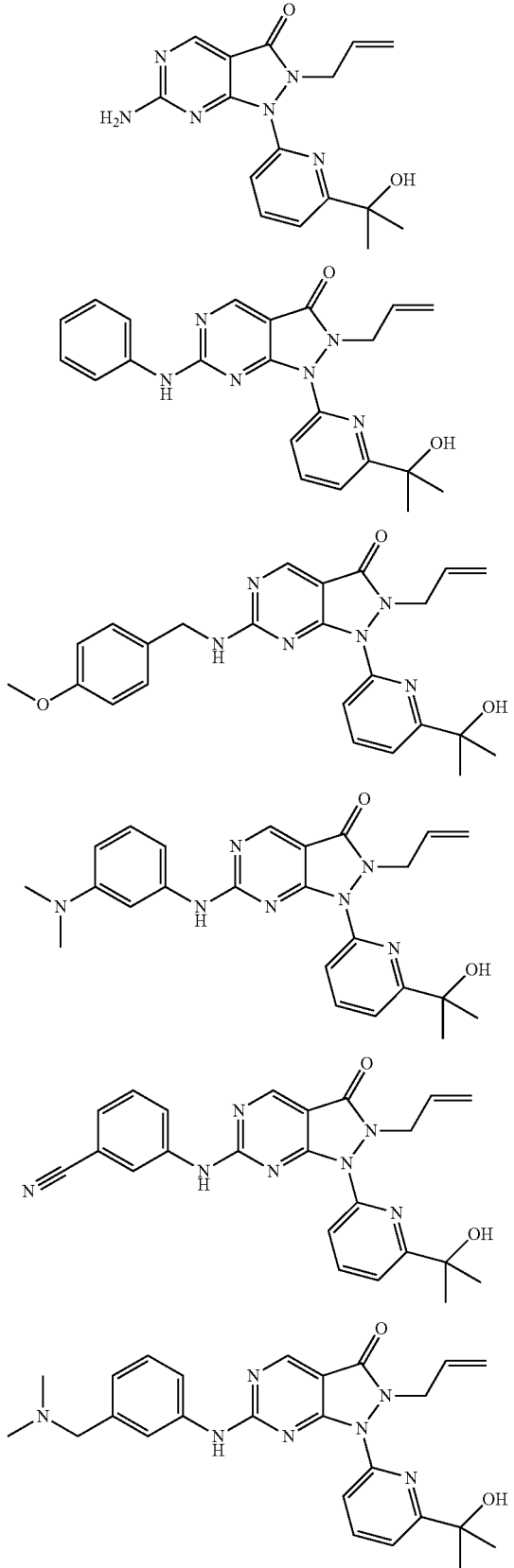
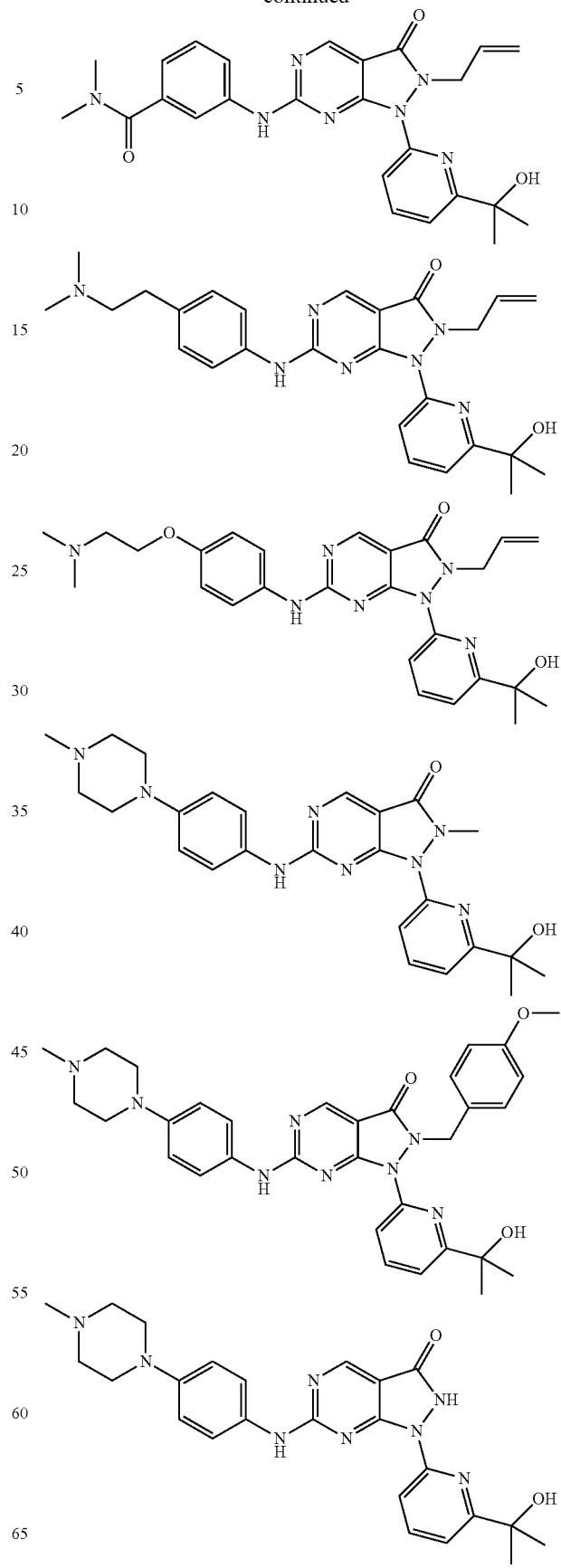

13
-continued
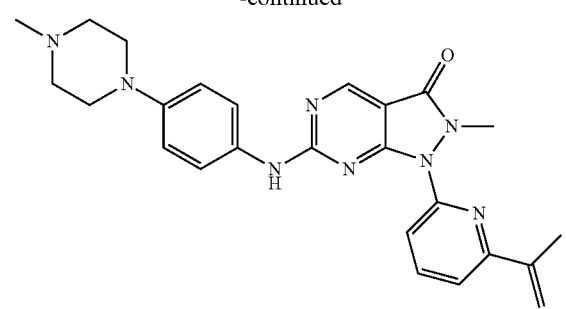
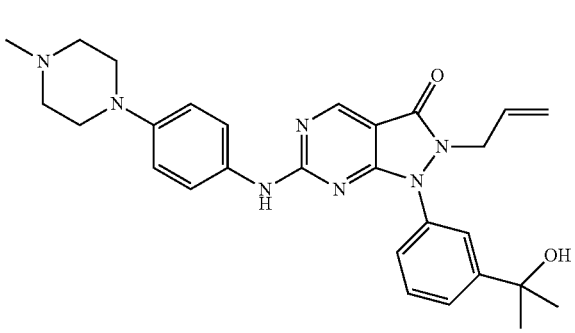
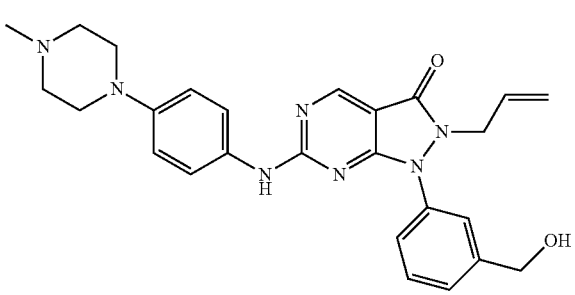
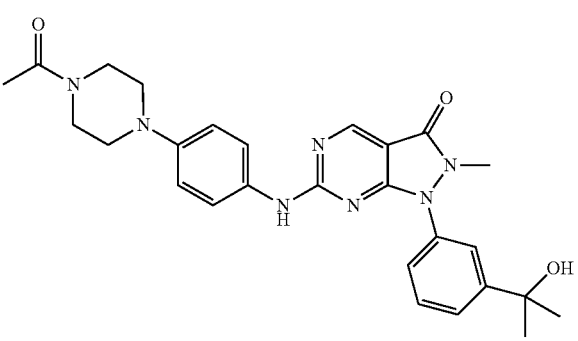
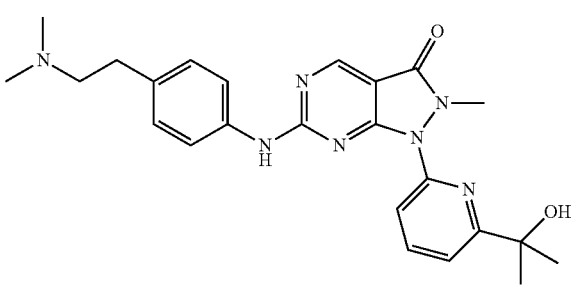
14
-continued
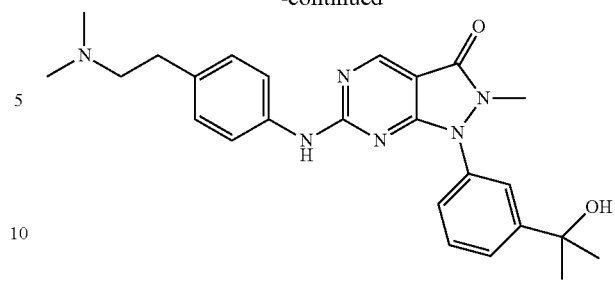
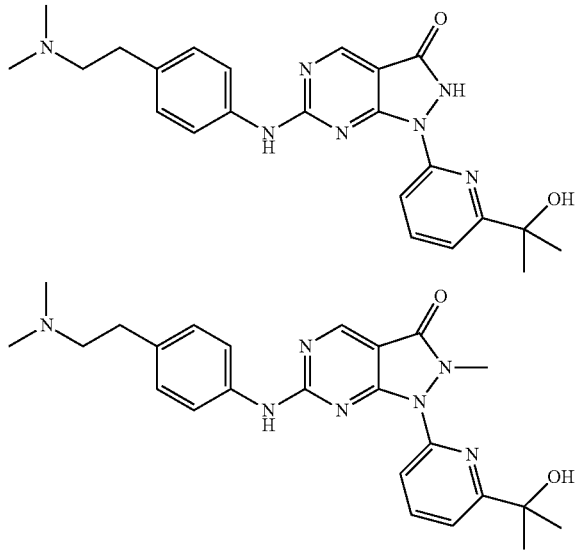
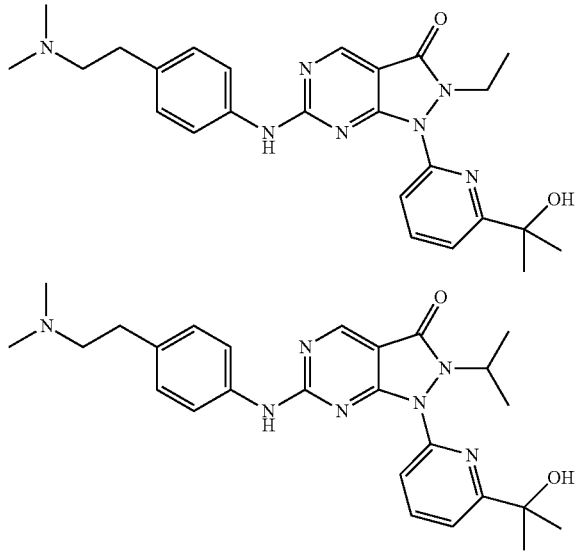
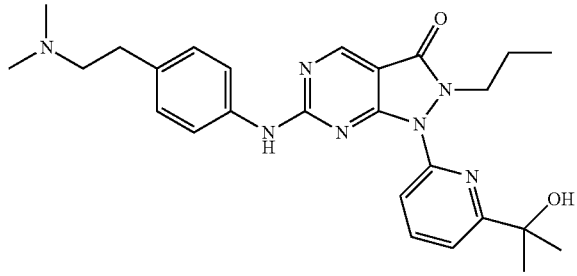

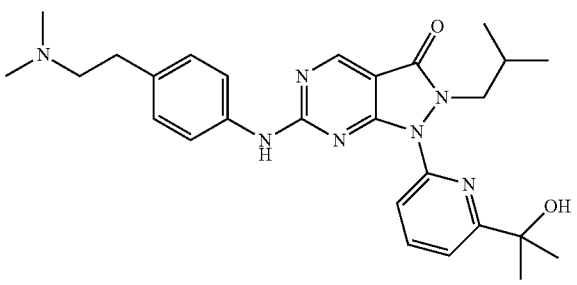
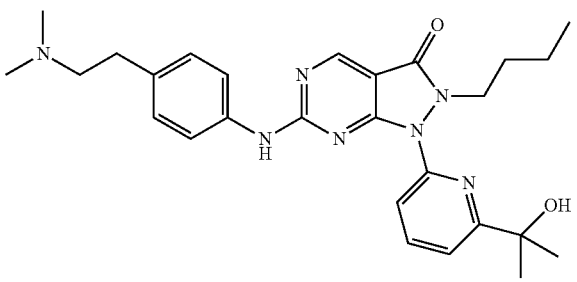
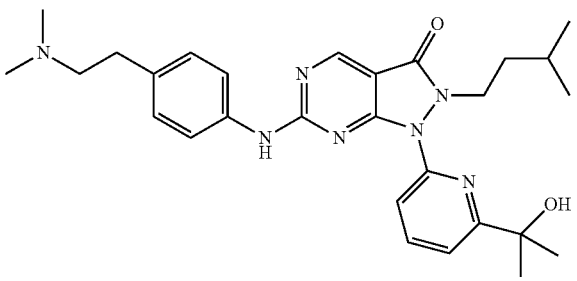
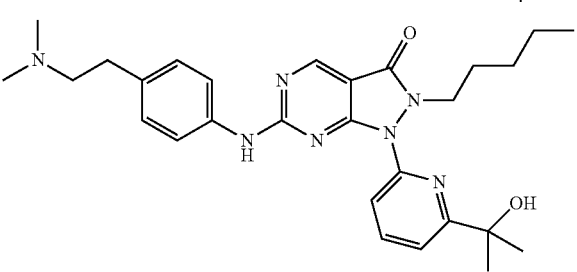
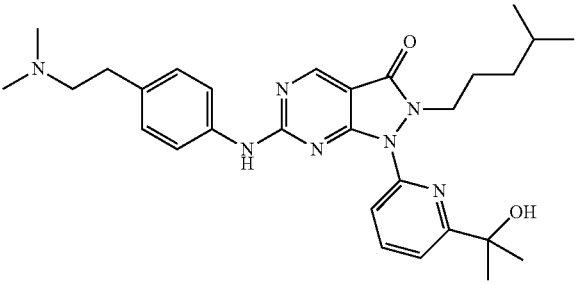
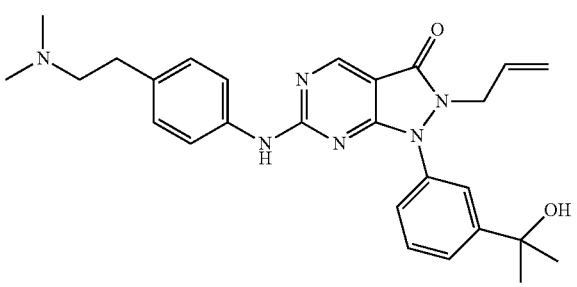

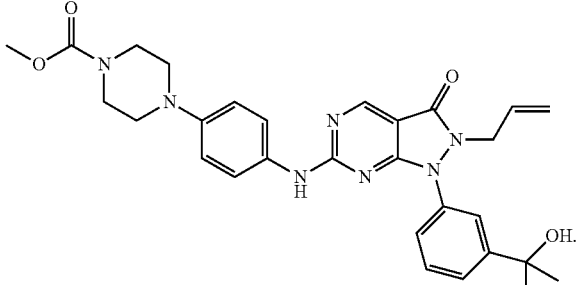
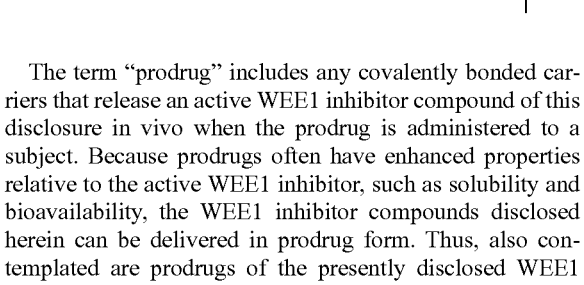

The term "prodrug" includes any covalently bonded carriers that release an active WEE1 inhibitor compound of this disclosure in vivo when the prodrug is administered to a subject. Because prodrugs often have enhanced properties relative to the active WEE1 inhibitor, such as solubility and bioavailability, the WEE1 inhibitor compounds disclosed herein can be delivered in prodrug form. Thus, also contemplated are prodrugs of the presently disclosed WEE1 inhibitor compounds, methods of delivering prodrugs, and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs may include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. For example, a prodrug of the WEE1 inhibitor compounds of this disclosure may include a lower alkyl phosphonate ester, such as an isopropyl phosphonate ester.

Exemplary prodrug moieties that form active prodrug compounds in combination with the WEE1 inhibitor compounds of this disclosure are nitroimidazoles that relies on bioreduction by a nitroreductase or oxidoreductase, in a hypoxic environment, for prodrug activation and release of the active WEE1 kinase inhibitor. These prodrugs provide additional tumor-selectivity into the prodrugs of this disclosure and reduce systemic side effects, such as cardiotoxicity and neurotoxicity often observed with many kinase inhibitors. Additional useful prodrugs include any prodrug compound described in US Patent Application Publication No. 2012/0077811, which is incorporated herein by this reference, in its entirety, for this purpose.

Thus, exemplary nitroimidazole prodrug moieties of this disclosure include compounds having the structure:

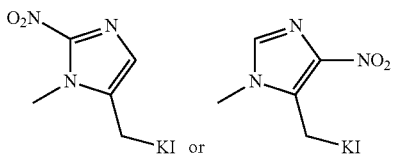

wherein 'KI' is a WEE1 kinase inhibitor of this disclosure. These nitroimidazole prodrug moieties are linked to the WEE1 kinase inhibitor through a tertiary nitrogen atom present in the kinase inhibitor chemical structure. Thus, examples of the prodrug WEE1 kinase inhibitor chemical structures of this disclosure include:

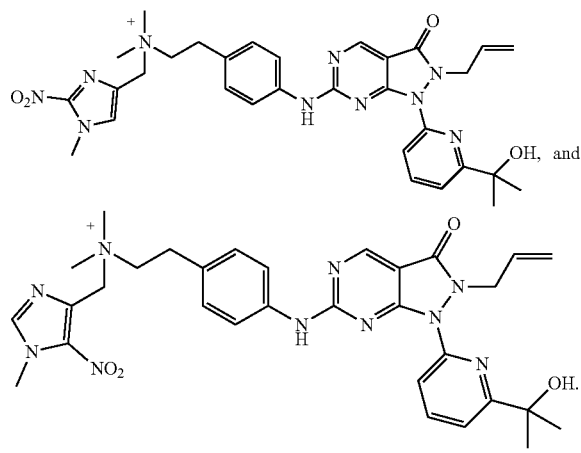

The WEE1 inhibitor compounds, and prodrugs thereof, disclosed herein may be used to prevent, treat, or ameliorate cancer, or prevent metastasis of cancer, in a subject by administering a therapeutically-effective amount of a compound of this disclosure that inhibits WEE1 kinase. For example, the disclosed compounds may be used to treat an advanced solid tumor, a blood cancer, a brain tumor, an ovarian tumor, cervical cancer, squamous cell cancer of the head and neck, pancreatic cancer, or lung cancer. These compounds may be particularly useful in treating acute myeloid leukemia. These compounds are small molecular weight lipophilic compounds with physicochemical properties that readily pass through the blood-brain barrier, thereby successfully treating brain tumors following systemic administration.

Therapeutically effective amounts of the disclosed compounds can be administered to a subject with a tumor to achieve an anti-tumor effect, such as inhibition of tumorigenesis or tumor metastasis. The disclosed compounds are also useful in the treatment of both primary and metastatic solid tumors. The disclosed compounds are also useful in treating hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds may be useful in the treatment of solid tumors arising from hematopoietic malignancies. In addition, these compounds may be useful in the prevention of metastases from the tumors described above either when used alone or in combination with radiotherapy and/or other chemotherapeutic agents. The compounds are also useful in treating multiple myeloma.

Further, a method for inhibiting the activity of the WEE1 kinase in a subject using the disclosed compounds is provided. The method includes administering a therapeutically effective amount of a disclosed compound to a subject to achieve a WEE1 inhibitory effect. The compounds of this disclosure having WEE1-inhibitory effects are useful for treating many inflammatory, infectious, immunological, and malignant diseases. These include, but are not limited to, cancer, tumor growth, undesirable angiogenesis, and autoimmune diseases.

WEE1 has been implicated in the maintenance and survival of cancer stem cells, including, specifically, glioblastoma (Forte et al PLoS One 2013 8(12):e81432), leukemia (Tuel-Ahlgren et al, Leuk Lymphoma 1996; 20(5-6):417-26; Zhou et al. Leukemia. 2015; 29(4):807-18), breast (Wang et al. Oncologist 2011; 16(7):966-79), and lung (Syljuasen et al. Front Genet. 2015; 6:70) cancers. Thus, further methods for inhibiting the activity of the WEE1 kinase in cancer stem cells using the disclosed compounds is provided. These methods may be particularly effective in preventing metastases of a tumor in a patient and/or treating drug-resistant cancers in a patient, which may include sensitizing cancer cells to other anticancer drugs that may be administered in combination with the WEE1 inhibitors of this disclosure.

The disclosed compounds can be used in combination with other compositions and procedures for the treatment of diseases. For example, a cancer may be treated conventionally with surgery, radiation, and/or chemotherapy in combination with one or more of the WEE1 kinase inhibitor compounds disclosed herein. Additionally, a cancer may be treated conventionally with a chemotherapeutic and one or more of the WEE1 kinase inhibitor compounds disclosed herein may be administered to reduce chemotherapeutic drug resistance of the cancer cells to the other chemotherapeutic.

The disclosed compounds exhibiting WEE1-inhibitory activity may be combined with other kinase inhibitory agents. The disclosed compounds exhibiting WEE1-inhibitory activity may be combined with other conventional anticancer therapies, for example, steroids such as dexamethasone and prednisolone.

Examples of other chemotherapeutic agents that can be used in combination with the disclosed compounds include DNA-targeted agents, including DNA alkylating agents and topoisomerase inhibitors, including cisplatin, capecitabine, carboplatin, cyclophosphamide, cytarabine, dauoribicin, docetaxel, doxorubicin, 5-fluorouracil, gemcitabine, methotrexate, paclitaxel, premetrexed, irinotecan temozolomide, topotecan, radiation, or combinations thereof. Particularly useful chemotherapeutic agents that can be used in combination with the disclosed compounds include cisplatin, cytarabine, temozolomide, doxorubicin, Bcl-2 inhibitors (such as ABT199), and combinations thereof.

The disclosed compounds also may be combined with radiotherapy employing radioisotopes (such as $^{32}P$, $^{90}Y$, $^{125}I$, $^{131}I$, and $^{177}Lu$), particle beams (such as proton, neutron and electron beams) and electromagnetic radiation (such as gamma rays, x-rays and photodynamic therapy using photosensitizers and visible or ultraviolet rays).

The disclosed compounds may be combined with pharmaceutically acceptable excipients, and optionally sustained-release matrices, such as biodegradable polymers, to form therapeutic compositions. Therefore, also disclosed are pharmaceutical compositions including one or more of any of the compounds of this disclosure and a pharmaceutically acceptable carrier. The composition may comprise a unit dosage form of the composition, and may further comprise instructions for administering the composition to a subject to inhibit cancer progression or metastasis, for example, instructions for administering the composition to achieve an anti-tumor effects or to inhibit a pathological cellular proliferation. Such pharmaceutical compositions may be used in methods for treating or preventing cancer growth in a subject by administering to the subject a therapeutically effective amount of the composition.

These pharmaceutical compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Pharmaceutical compositions can be administered systemically or locally in any manner appropriate to the treatment of a given condition, including orally, parenterally, intrathecally, rectally, nasally, buccally, vaginally, topically, optically, by inhalation, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions may readily penetrate the blood-brain barrier when peripherally or intraventricularly administered.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of, for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic, parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, for example buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture. For example, a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day can be useful for treatment of a particular condition.

The compounds can be used in the form of pharmaceutically acceptable salts derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, for example, with such agents as $C_{1-8}$ alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

Pharmaceutically acceptable salts of the presently disclosed WEE1 inhibitor compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function, such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

Each publication or patent cited herein is incorporated herein by reference in its entirety. The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1

The Role of WEE1 in Cancer

The inventors have examined the expression of WEE1 in a panel of pediatric brain tumors and found WEE1 to be overexpressed in the high-grade tumors including medulloblastoma (medullo), primitive neuroectodermal tumor (PNET) and pediatric GBM, and in the low-grade pilocytic astrocytoma (PA) compared with normal brain. These data support increased WEE1 expression is implicated in tumorigenesis.

To further support targeting WEE1 in medulloblastoma the inventors examined the expression of WEE1 in 90 medulloblastoma tissue samples. There was significant overexpression of WEE1 in the medulloblastoma tissue compared with normal cerebellum, and importantly there was no significant difference in WEE1 expression between the 4 medulloblastoma sub-groups (Wnt, Shh, Group 3 and Group 4), suggesting that targeting medulloblastoma would be effective in all sub-groups. Furthermore, the inventors evaluated WEE1 expression in a panel of well-characterized medulloblastoma cell lines. WEE1 was not present in pediatric (UPN 514 and 605) or adult cerebellum tissue samples, but was present in the 6 medulloblastoma cell lines. To determine the functional consequence of inhibiting WEE1 the inventors used siRNA against WEE1 and measured cell proliferation using the xCELLigence real-time cell analysis (RTCA) system in Daoy and UW228 cells. A decrease in cell growth was observed in the Daoy and UW228 cell lines. Then the inventors used the colony-forming assay to determine the ability of medulloblastoma cells to undergo an unlimited number of divisions following inhibition of WEE1 by siRNA. The siRNA targeting WEE1 showed a decrease in the relative colony number compared with the non-silencing siRNA in Daoy and UW228 cell lines.

Several small molecule inhibitors of WEE1 have been described (Clin Cancer Res. 2011; 17(13):4200-7; Mol Cancer Ther. 2009; 8(11):2992-3000; Cancer Cell. 2010; 18(3):244-57), but none are highly selective for WEE1 and the most potent, AZD1775, is currently being evaluated in clinical trials in combination with DNA damaging agents for several cancer types. A high-throughput screen (HTS) conducted by Merck Research Laboratories on a small chemical compound library identified MK1775 (now known as AZD1775) as a small-molecule nanomolar inhibitor of WEE1 kinase. Inhibition of WEE1 by AZD1775 has been shown in some cancers to abrogate the G2 checkpoint, forcing cancer cells with DNA damage to enter unscheduled mitosis to undergo cell death (Cancer biology & therapy. 2010; 9(7):523-5; Current clinical pharmacology. 2010; 5(3):186-91). Like Chk1, inhibition of WEE1 in combination with DNA-damaging agents has been explored as a therapeutic strategy for tumors with dysregulated p53 (Clinical cancer research, 2011; 17(17):5638-48). However, WEE1 is downstream of Chk1; therefore, inhibition of WEE1 kinase activity is less likely to produce the severe side effects associated with the inhibition of the upstream master regulators. The inventors have shown that WEE1 inhibition by the small molecule inhibitor AZD1775 suppressed cell growth, induced apoptosis, and decreased tumor growth as a single agent and displayed synergistic activity with cisplatin in medulloblastoma cells (Mol Cancer. 2014; 13:72). Furthermore, the inventors' data suggests that cell growth inhibition induced by AZD1775 as a single agent is independent of p53 status in medulloblastoma and acute myelogenous leukemia (AML) cell lines (Mol Cancer Ther. 2013; 12(12):2675-84). Collectively, their data support that WEE1 is a promising candidate for targeted therapy in medulloblastoma and that inhibition of WEE1 kinase activity has the potential to chemosensitize the tumor to DNA-damaging agents.

The structure-activity relationship (SAR) data for AZD1775 is limited, as it was not developed through a focused medicinal chemistry effort, but discovered from a HTS, and it is known to have nanomolar activity with at least 8 other kinases. This lack of SAR and kinase selectivity data and the potent single agent cellular toxicity of AZD1775 was a concern as off-target effects resulting in cellular toxicity that are unrelated to WEE1 inhibition may exacerbate therapy-related adverse effects in patients with medulloblastoma. Although AZD1775 has been reported to be "well-tolerated" in clinical trials, there has been no single agent safety and tolerability study for AZD1775 and its toxicity could be masked by combination therapies. These concerns supported the current inventors' development of new selective WEE1 inhibitors for the treatment of medulloblastoma. The inventors developed a small series of WEE1 inhibitors based on AZD1775 to establish assay systems and further examine the effects of WEE1 inhibition in medulloblastoma. Interestingly, the inventors' compounds that inhibited WEE1 in the same nanomolar range as AZD1775 in an in vitro kinase assay did not exhibit the same potent inhibitory effect on medulloblastoma cell growth as single agents, yet these compounds reduced pCDK levels and demonstrated synergy with cisplatin at non-toxic inhibitor concentrations. The inventors have now developed inhibitors with improved selectivity for WEE1, evaluating their single agent cytotoxicity, synergy with cisplatin, blood-brain barrier (BBB) penetration, pharmacokinetic profiles, and inhibition of tumor growth in xenograft models.

Example 2

The Identification of WEE1 Kinase in Brain Cancer

To identify novel molecular targets for medulloblastoma therapy, the inventors performed an integrated genomic screen using pathway analysis of gene expression in tumor tissue and a kinome-wide siRNA screen in the Daoy medulloblastoma cell line. The inventors performed gene expression profiling on 16 medulloblastoma and 3 normal cerebellar tissue samples, measured by Affymetrix microarrays (Int J Cancer. 2012; 131(8):1800-9). A pathway analysis was performed using IPA software (Ingenuity) and gene set enrichment analysis to identify specific signaling networks. Cell cycle-related genes were the most abundant in the molecular category and kinases were the most abundant in the functional category. The comparison of the molecular and functional categories with the total dysregulated genes in medulloblastoma identified 50 specific genes, with 29 significantly overexpressed in medulloblastoma compared with normal cerebellum. The inventors then performed a kinome-wide siRNA screen to identify kinases that are essential for medulloblastoma cell proliferation. The medulloblastoma Daoy cell line was transfected with 2130 siRNAs targeting each of 710 kinase genes or a non-silencing control.

Cell proliferation was evaluated by MTS assay after 72 hours of transfection. Absorbance values were normalized to controls and the average Z score was calculated. A total of 95 genes were identified (Z score of ≤2) that decreased Daoy cell growth when inhibited. The combined analysis of the 29 genes overexpressed from the gene expression data and the 95 kinases identified in the siRNA screen identified cell cycle-related kinases in the G2 checkpoint, implicating the G2 checkpoint control as a target for medulloblastoma therapy.

Many cancers possess a deficient G1 checkpoint that impairs the ability of the cell to halt the cell cycle to repair DNA damage prior to replication (Drug Discovery Today. 2012; 17(5-6):194-202). This gives cancer cells a means to accumulate mutations and propagate irregularities that are favorable to cancer formation. In normal cells, the G1 checkpoint is not compromised; therefore, the G2 checkpoint is not burdened with halting the cell cycle prior to DNA damage repair. This demonstrates abrogation of the G2 checkpoint selectively impacts tumorigenesis rather than normal cell growth. The inventors' combined genomic analysis and siRNA screen identified WEE1 as a focal kinase in two signaling pathways demonstrating that targeting WEE1 for inhibition has the potential to disrupt multiple tumor survival mechanisms.

WEE1 is a tyrosine kinase that is a critical component of the ATR-mediated G2 cell cycle checkpoint control that prevents entry into mitosis in response to cellular DNA damage (Cell Cycle. 2 013; 12(19):3159-64). ATR phosphorylates and activates CHK1, which in turn activates WEE1, leading to the selective phosphorylation of cyclin-dependent kinase 1 (CDK1) at Tyr15, thereby stabilizing the CDK1-cyclin B complex and halting cell-cycle progression. This process confers a survival advantage by allowing tumor cells time to repair damaged DNA prior to entering mitosis. Inhibition of WEE1 abrogates the G2 checkpoint, forcing cancer cells with DNA damage to enter into unscheduled mitosis and undergo cell death via mitotic catastrophe.

Example 3

Identification of WEE1 in Acute Myeloid Leukemia

WEE1 has been identified as a mediator of acute myelogenous leukemia (AML) cell survival after treatment with cytarabine, an antimetabolite that induces S-phase arrest, and a key component of successful AML therapy. The addition of a WEE1 inhibitor to cytarabine impairs the cell-cycle checkpoint and induces more apoptosis than cytarabine alone. These data were generated in cell lines that are reported to have normal p53 function.

To determine whether the function of p53 influences the sensitivity to WEE1 inhibition with chemotherapy, the inventors tested a broad panel of AML cell lines with various molecular abnormalities (Mol. Cancer Ther., 12(12):2675-84 (2013)). In contrast to data from solid tumor models sensitized to DNA-damaging agents, the functionality of p53 had no bearing on the chemosensitization of AML cells to cytarabine as all the cell lines tested were sensitized to cytarabine with WEE1 inhibition. Additionally, the chemosensitization to antimetabolite chemotherapeutics was not limited to leukemia, as lung cancer cells were equally sensitized to cytarabine and pemetrexed, whether p53 function was impaired or not. Finally, in mice with AML, the combination of WEE1 inhibition with cytarabine slowed disease progression and prolonged survival better than cytarabine alone.

To confirm that the combination of antimetabolite chemotherapy plus WEE1 inhibition is tolerable and effective in vivo, the inventors modeled therapy in mice. Mice without leukemia were treated with cytarabine (50 mg/kg/d), with or without a WEE1 inhibitor (40 mg/kg/d) for 5, 7, or 10 days, demonstrating that the longer courses of single or combination therapy were toxic, resulting in pancytopenia. In a second toxicity study, mice without leukemia were treated with cytarabine and/or a WEE1 inhibitor for 5 of 7 days for 3 consecutive weeks. The addition of the WEE1 inhibitor did not enhance the hematologic effects of cytarabine with this regimen. The inventors then used an aggressive model of murine AML-expressing MLL-ENL, FLT3-ITD, and luciferase, to determine whether WEE1 inhibition would enhance the anti-leukemia effects of cytarabine. In these tests, cytarabine alone slowed the progression of the leukemia, as measured by luciferase expression over time. The addition of the WEE1 inhibitor to the cytarabine treatments markedly enhanced the effects of cytarabine in slowing disease progression, and significantly enhanced survival as compared with cytarabine alone, demonstrating that WEE1 inhibition can be effectively combined with cytarabine to slow leukemia progression in vivo.

Taken together, these data show that the combination of WEE1 inhibition and cytarabine is a broadly applicable therapeutic strategy for AML, independent of several known molecular abnormalities, including mutation in TP53. Furthermore, the inhibition of WEE1 in combination with other clinically relevant antimetabolites should be tested, as this strategy may be applicable across a number of different cancer types, including lung cancer.

Example 4

LanthaScreen TR-FRET Assay to Determine Inhibition of WEE1 Kinase Activity

A LanthaScreen™ kinase activity assay was conducted to assess WEE1 kinase inhibitory activity for compounds of this disclosure. LanthaScreen Eu time-resolved fluorescence resonance energy transfer (TR-FRET) kinase binding assays (Invitrogen) were performed in 384-well, low-volume plates (Corning) using recombinant WEE1 kinase, Kinase Tracer 178 and LanthaScreen Eu-anti-GST antibody (Invitrogen). Assays were performed at 25° C. in a reaction mixture consisting of 5 μL serially diluted inhibitor solution, 5 μL Kinase Tracer 178 solution, and 5 μL kinase/antibody solution. All reagents were prepared as solutions in 1× kinase buffer A (Invitrogen) at 3× final desired concentration. Inhibitor solutions were prepared such that final DMSO concentrations did not exceed 0.5%, which was shown to have no effect on kinase activity. Inhibitors were assayed in the final concentration range of 0.04 nM to 10 μM. Kinase Tracer 178 was used at a final concentration of 150 nM and the antibody and kinase were used at final concentrations of 3 nM and 5 nM, respectively. All reagents were incubated together for 1 hour at room temperature and read using a PerkinElmer Envision 2104 Multilabel Reader enabled for TR-FRET (Excitation=340 nm; Tracer emission=665 nm; Antibody emission=615 nm; Delay=100 μs; Integration=200 μs). Emission ratios (665 nm/615 nm) were determined for each inhibitor concentration and the data analyzed usinga non-linear regression analysis of the log dose-response curve todetermine $IC_{50}$ values.

Calculated IC50 values from this assay are shown for specific WEE1 inhibitor compounds in the following table:

| Compound | IC$_{50}$ |
|---|---|
| 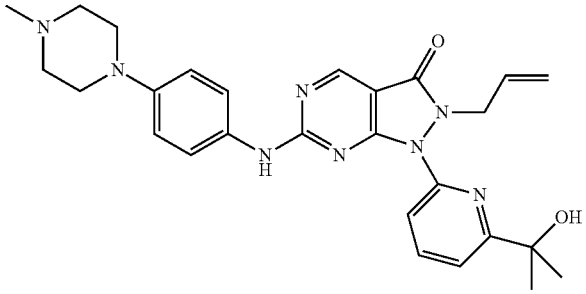 AZD1775 | 5.1 nM |
| 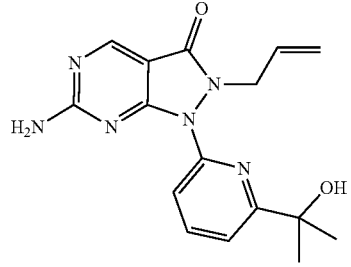 KAC-030 | 17.7 nM |
| 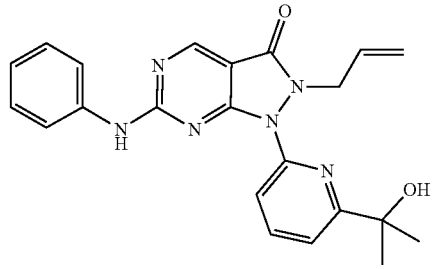 KAC-017 | 9.6 nM |
| 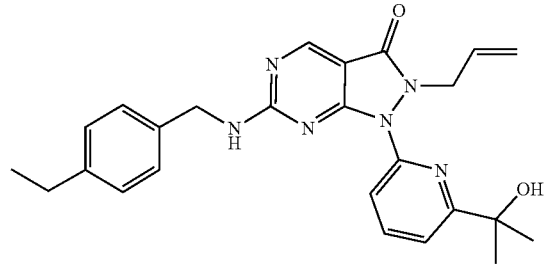 KAC-011 | 13.6 nM |
| 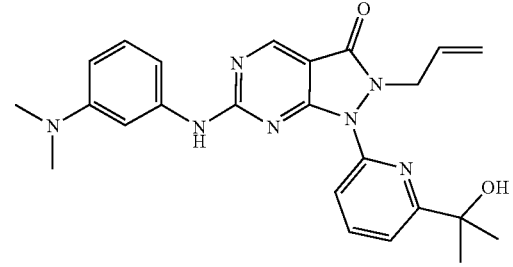 KAC-019 | 6.3 nM |

| Compound | IC$_{50}$ |
|---|---|
| 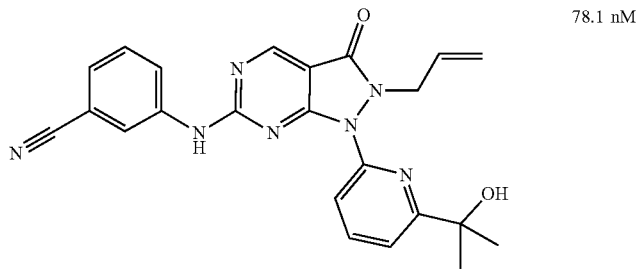<br>KAC-012 | 78.1 nM |
| 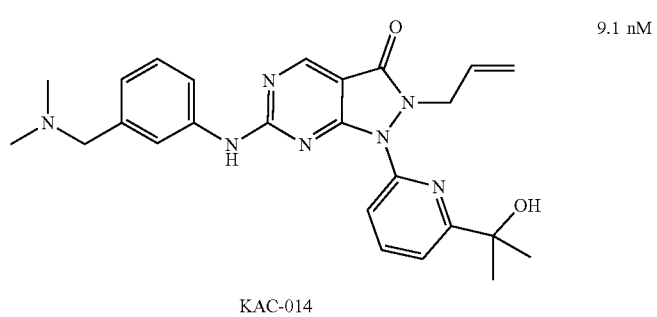<br>KAC-014 | 9.1 nM |
| 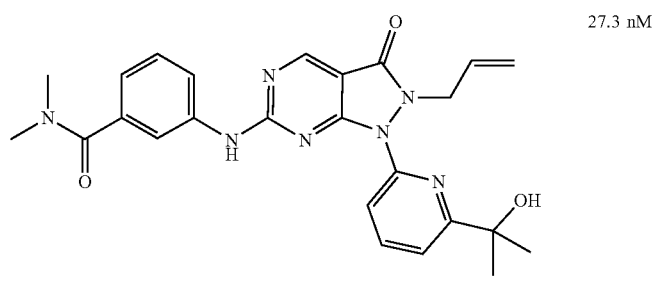<br>KAC-016 | 27.3 nM |
| 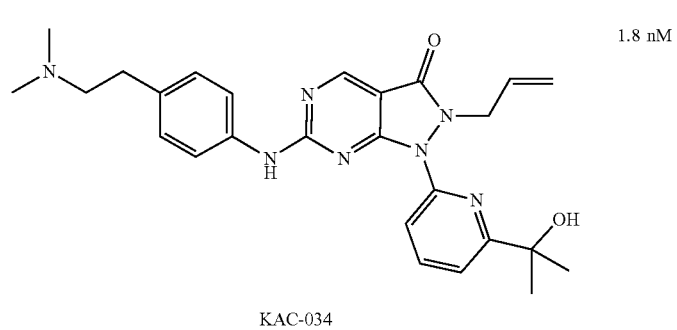<br>KAC-034 | 1.8 nM |
| 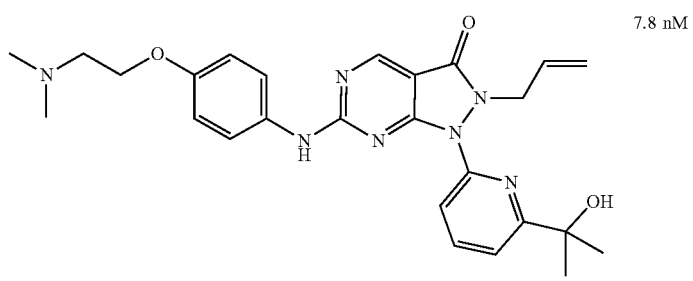<br>CM-181 | 7.8 nM |

-continued
| Compound | IC$_{50}$ |
|---|---|
| 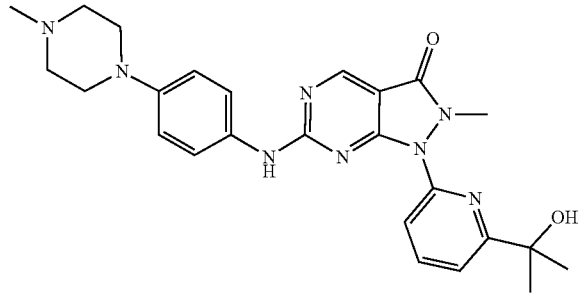"CM-185" | 19.9 nM |
| 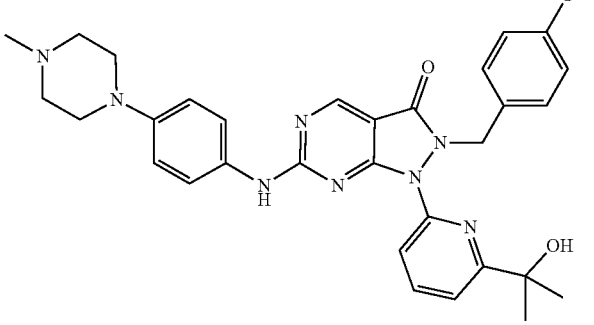"CM-188" | 89.7 nM |
| 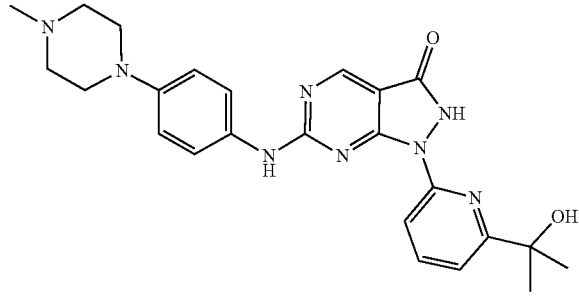"CM-235" | 152 nM |
| 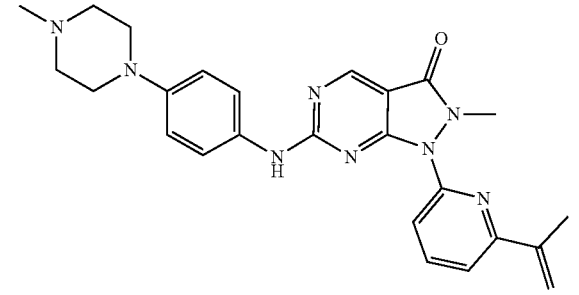"CM-189" | 179 nM |

| Compound | IC$_{50}$ |
|---|---|
| 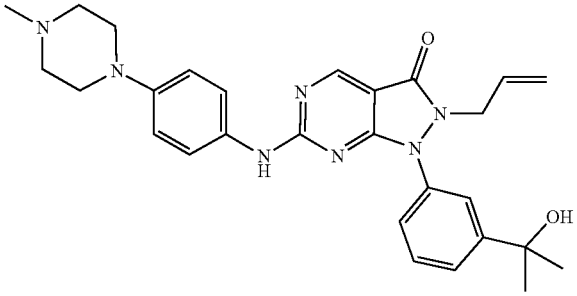 CM-169 | 6.9 nM |
| 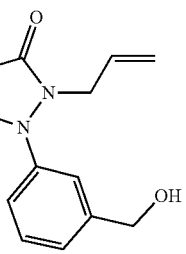 CM-170 | 10.4 nM |

Example 5

Effect of WEE1 Inhibitors on Cell Viability in Medulloblastoma Cells

Figure 1B:
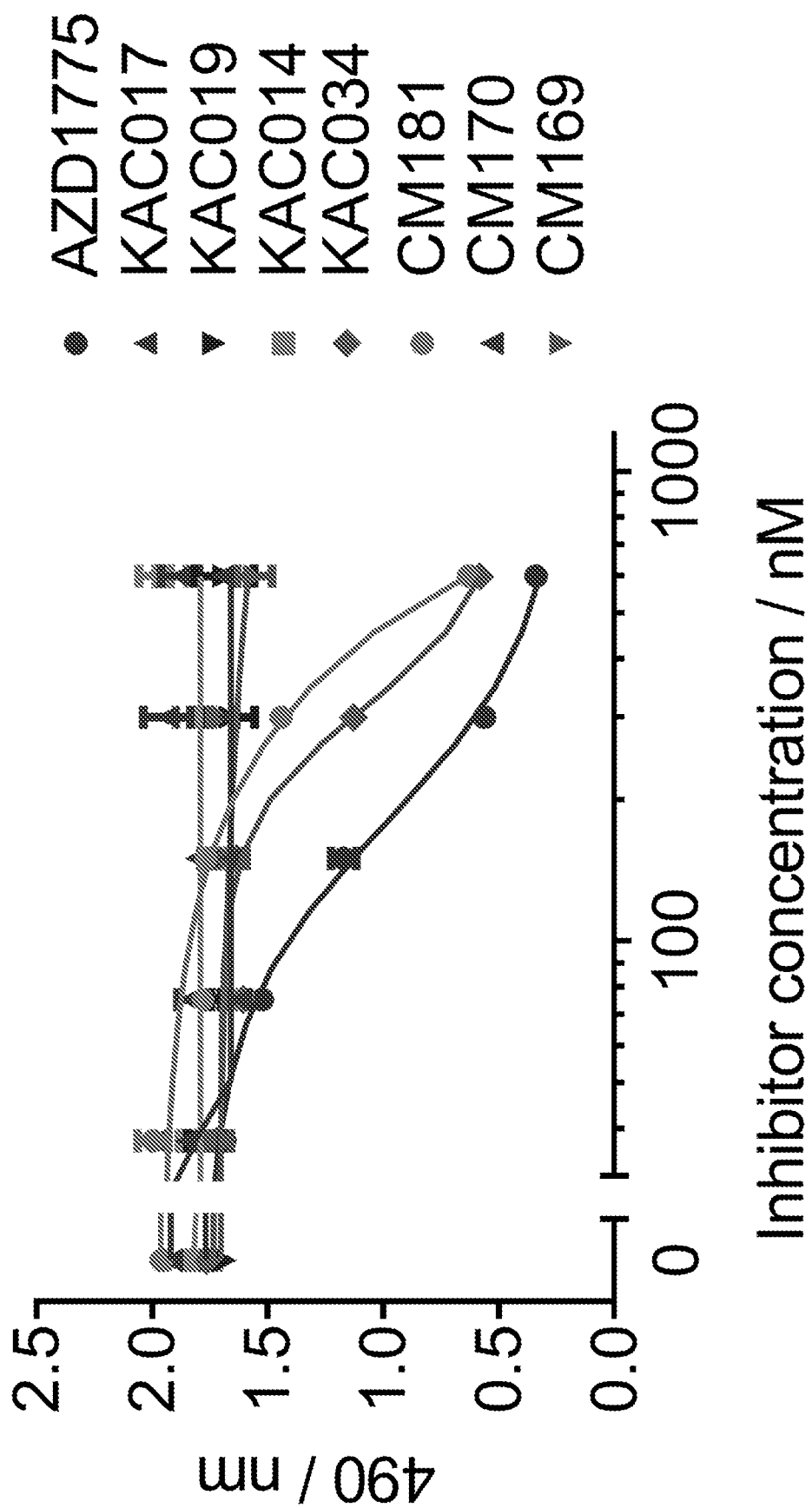

To evaluate the effect of the WEE1 kinase inhibitors, Daoy cells and ONS-76 cells (human primary medulloblastoma cell lines) were treated with test compounds and cell growth was by MTS assay (FIGS. 1A and 1B). Daoy and ONS-76 cells were seeded into sterile 96-well plates (Corning Inc.) at 2000 cells/well in 100 µL media. Inhibitors were administered at the MTS EC$_{50}$ of AZD1775 (Daoy; EC$_{50}$=150 nM, ONS-76; EC$_{50}$=290 nM) and concentrations above and below the EC$_{50}$. Cells were incubated for 72 hr with 50 µL of each diluted drug solution. Cell viability was measured by 2 hr incubation with 30 µL CellTiter 96® AQueous One Cell Proliferation reagent (Promega) and formazan concentration assessed through colorimetric analysis using a BioTek Synergy H1 plate reader (Absorption=490 nm). Mean IC$_{50}$ values, or percent cell inhibition, for the tested compounds are listed in the following table:

| CMPD | DAOY | ONS-76 |
|---|---|---|
| AZD1775 | 378 nM | 221 nM |
| KAC-014 | ND | 40% @ 1160 nM |
| KAC-017 | ND | 32% @ 1160 nM |
| KAC-019 | ND | 33% @ 1160 nM |
| KAC-034 | 83% @ 600 nM | 495 nM |
| CM-169 | ND | 61% @ 1160 nM |
| CM-170 | ND | 59% @ 1160 nM |
| CM-181 | 82% @ 600 nM | 273 nM |

ND = Not determined. There was no appreciable decrease in cell viability over the concentration range for the time period examined.

Example 6

CDK ELISA to Determine Inhibition of WEE1 Kinase Activity in DAOY Cells

Figure 2A:
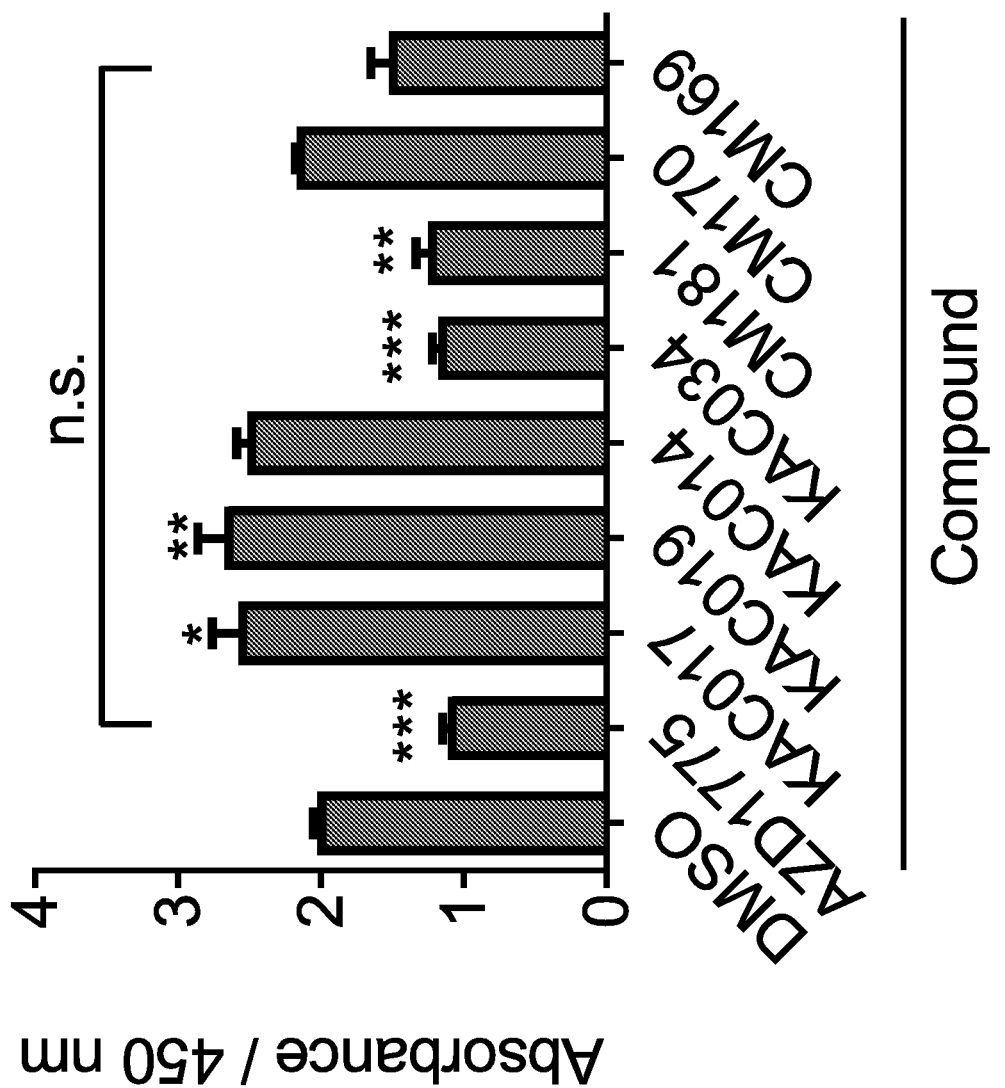
FIGS. 2A and 2B show the effects of WEE1 inhibition by WEE1 inhibitors of this disclosure on DAOY cells.
Figure 2B:
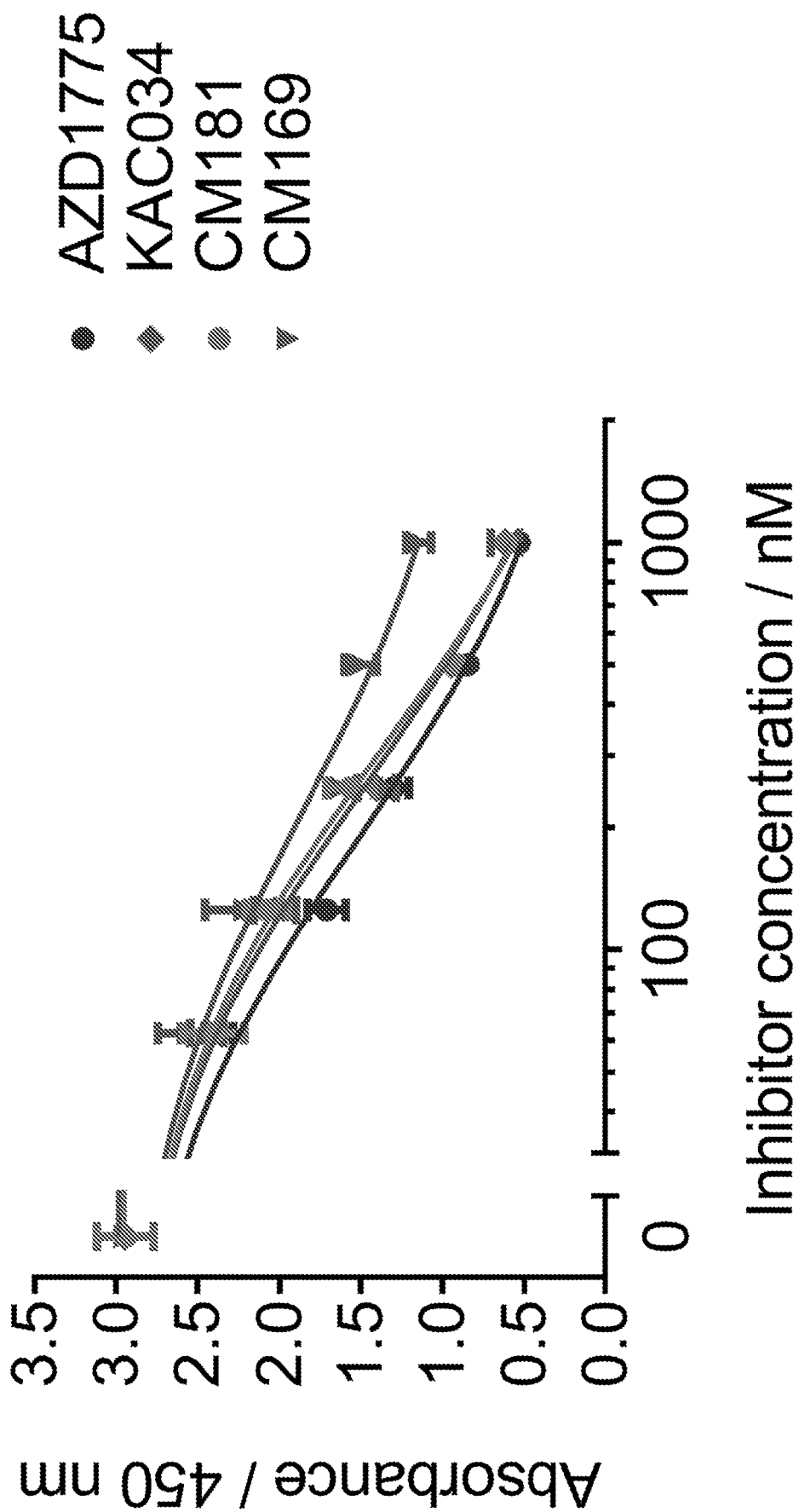

WEE1 inactivates CDC2 through selective phosphorylation of the Tyr15 residue of cyclin-dependent kinase 1 (CDK1) stabilizing the CDC2-cyclin B complex. Therefore, inhibition of WEE1 kinase activity will prevent the phosphorylation of its substrate CDK1 at Tyr15. For quantitative analysis, an ELISA assay was utilized to determine the relative levels of pCDK1 (Tyr15) in Daoy cell lysates following treatment with WEE1 inhibitors of this disclosure at a single concentration (220 nM; FIG. 2A) and over a concentration range (FIG. 2B). Daoy cells were plated in sterile 6-well plates at 200,000 cells/well and treated with active inhibitors at a dose of 220 nM and incubated for 24 hr prior to preparing cell lysates. Any compounds that were found to inhibit cellular p-CDK1 levels at this concentration when compared to DMSO control were tested across a concentration range from 1000 µM to 62.5 µM. Following drug incubation, the media was aspirated from cells before cells were trypsinized and resuspended in TES/SB buffer containing protease inhibitors. Cells were lysed on ice through sonication, and cell lysates were diluted with ELISA Pathscan® sample diluent to a final volume of 100 µL and protein concentration of 0.05 mg/ml prior to use. The relative concentration of p-CDK1 Tyr15 was determined using an enzyme-linked immunosorbent assay according to recommended protocol (Cell Signaling, ELISA Pathscan® phosphor-Cdc2 (Tyr15)).

Example 7

Synthesis of Inhibitors

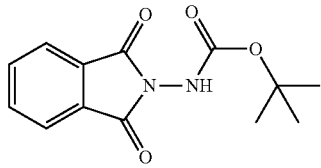 [SMILES: CC(C)(C)OC(=O)NN1C(=O)c2ccccc2C1=O]

Synthesis of tert-butyl (1,3-dioxoisoindolin-2-yl)carbamate tert-Butyl carbazate (9.40 g, 70.9 mmol) was added portion-wise to a solution of phthalic anhydride (10.0 g, 67.5 mmol) in refluxing toluene (110 ml). The resultant suspension was heated under reflux conditions for 18 h, before being cooled and the precipitate removed by filtration. The filtrand was washed with hexanes and dried under vacuum to give the desired product as a white crystalline solid (16.1 g, 61.4 mmol, 91%). Rf 0.68 (1:1 Hexane:EtOAc); M.p. 191-194° C. (Lit.=186° C.); [37] IR (cm$^{-1}$) 3316, 2979, 1796, 1730, 1614, 1490; $^1$H NMR (400 MHz, DMSO-d$_6$) 1.45 (9H, s, —OC(CH$_3$)$_3$), 7.87-8.04 (4H, m, H-4/5/6/7), 9.86 (1H, s, NH); $^{13}$C NMR (100 MHz, DMSO-d$_6$) 28.3 (C(CH$_3$)$_3$), 81.6 (C(CH$_3$)$_3$), 124.2 (Ar—C), 129.8 (Ar—C), 135.8 (Ar—C), 154.4 (C=O), 165.9 (C=O).

General Procedure for the Alkylation of tert-butyl (1,3-dioxoisoindolin-2-yl)carbamate To a suspension of the tert-butyl (1,3-dioxoisoindolin-2-yl)carbamate (1.0 equiv.) in acetonitrile (2 mL/mmol) was added benzyltriethylammonium chloride (0.1-0.2 equiv.), potassium carbonate (4.0 equiv.) and the relevant alkylhalide (1.5-5.0 equiv.) sequentially. The reaction mixture was stirred at RT or 50° C. for 18-48 h, before water (2 mL/mmol) was added and the organic phase was extracted with diethyl ether (2×5 mL/mmol). The combined organic extracts were dried (MgSO4) and evaporated to dryness, and were purified by chromatography on silica if necessary.

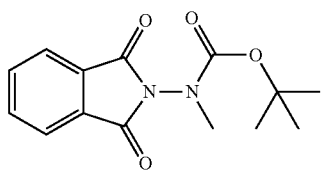 [SMILES: CN(C(=O)OC(C)(C)C)N1C(=O)c2ccccc2C1=O]

Synthesis of tert-butyl (1,3-dioxoisoindolin-2-yl)(methyl)carbamate tert-Butyl (1,3-dioxoisoindolin-2-yl)carbamate (100 mg, 0.38 mmol), benzyltriethylammonium chloride (17 mg, 0.08 mmol), potassium carbonate (210 mg, 1.52 mmol) and methyl iodide (118 μL, 1.90 mmol) were reacted in acetonitrile (1 mL) according to the described general procedure with heating at 50° C. for 48 hr required for completion. Purification on silica gel (1:1 Hexanes:EtOAc) afforded the target compound as a white crystalline solid (93 mg, 0.34 mmol, 89%). Rf 0.38 (1:1 Hexanes:EtOAc); M.p. 118-120° C. (Lit.=123° C.); [37] IR (cm$^{-1}$) 2972, 2934, 1791, 1723, 1609; $^1$H NMR (400 MHz, CDCl$_3$) 1.34 (5.1H, s, C(CH$_3$)$_{3\text{-}major}$), 1.53 (3.9H, S, C(CH$_3$)$_{3\text{-}minor}$), 3.29 (1.7H, s, N—CH$_{3\text{-}major}$), 3.32 (1.3H, s, N—CH$_{3\text{-}minor}$), 7.74-7.93 (4H, m, H-4/5/6/7); $^{13}$C NMR (100 MHz, CDCl$_3$) 27.9 (C(CH$_3$)$_{3\text{-}major}$), 28.1 (C(CH$_3$)$_{3\text{-}minor}$), 36.5 (N—CH$_{3\text{-}major}$), 38.1 (N—CH$_{3\text{-}minor}$), 82.2 (C(CH$_3$)$_{3\text{-}major}$), 82.9 (C(CH$_3$)$_{3\text{-}minor}$), 123.8 (Ar—C), 129.9 (Ar—C), 130.1 (Ar—C), 134.6 (Ar—C), 134.7 (Ar—C), 153.6 (C=O$_{-major}$), 153.8 (C=O$_{-minor}$), 165.0 (C=O$_{-major}$), 165.3 (C=O$_{-minor}$); MS [M+H]$^+$ m/z 276.8.

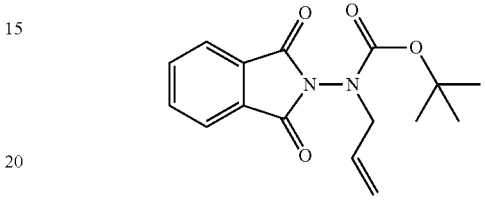

Synthesis of tert-butyl allyl(1,3-dioxoisoindolin-2-yl)carbamate tert-Butyl (1,3-dioxoisoindolin-2-yl)carbamate (16.1 g, 61.2 mmol), benzyltriethylammonium chloride (1.39 g, 6.12 mmol), potassium carbonate (16.1 g, 116 mmol) and allyl bromide (8.00 mL, 91.8 mmol) were reacted in acetonitrile (110 mL) according to the described general procedure with stirring at RT for 18 hr required for completion. Trituration with hexanes at 0° C. afforded the desired product as a white crystalline solid (15.7 g, 52.1 mmol, 85%) with no further purification needed. Rf 0.52 (4:1 Hexane:EtOAc); M.p. 72-75° C. (Lit.=76-78° C.); [37] IR (cm$^{-1}$) 2978, 2936, 1792, 1719, 1641; $^1$H NMR (400 MHz, DMSO-d$_6$) 1.25 & 1.46 (9H, s, C(CH$_3$)$_3$), 4.19 (2H, d$_{app}$, J=6.1 Hz, N—CH$_2$), 5.10-5.17 (1H, m, allyl C—H$^{trans}$), 5.27 (1H, dd, J=17.3, 1.3 Hz, allyl C—H$^{cis}$), 5.78-5.93 (1H, m, allyl C—H), 7.93-8.02 (4H, m, H-4/5/6/7); $^{13}$C NMR (100 MHz, DMSO-d$_6$) 27.9 (C(CH$_3$)$_{3\text{-}major}$), 28.1 (C(CH$_3$)$_{3\text{-}minor}$), 51.7 (N—CH$_{2\text{-}major}$), 53.7 (N—CH$_{2\text{-}minor}$), 82.1 (C(CH$_3$)$_{3\text{-}major}$), 82.8 (C(CH$_3$)$_{3\text{-}minor}$), 119.1 (allyl-CH$_{2\text{-}major}$), 119.7 (allyl-CH$_{2\text{-}minor}$), 124.3, 124.4, 129.5, 129.6, 132.8 (Ar—C), 133.3 (Ar—C), 135.9 (Ar—C), 136.0 (Ar—C), 153.0 (C=O$_{-major}$), 153.1 (C=O$_{-minor}$), 165.3 (C=O$_{-major}$), 165.5 (C=O$_{-minor}$).

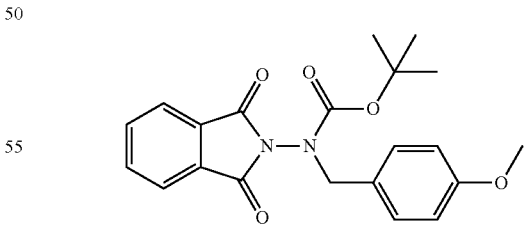

Synthesis of tert-butyl (1,3-dioxoisoindolin-2-yl)(4-methoxybenzyl)carbamate Diethyl azodicarboxylate (45 μL, 0.29 mmol) in dry THF (0.5 mL) was added dropwise over 10 minutes to a solution of tert-butyl (1,3-dioxoisoindolin-2-yl)carbamate (50 mg, 0.19 mmol), 4-methoxybenzyl alcohol (72 uL, 0.57 mmol)

and triphenylphosphine (75 mg, 0.29 mmol) in dry THF (1 mL) at RT. The mixture was stirred for 16 hr at RT before being concentrated in vacuo and the residue triturated in EtOAc (2 mL) and stored at 4° C. overnight. The precipitated $PPh_3O$ was removed by filtration and the filtrate was concentrated and purified on silica gel (3:1 Hexanes:EtOAc) to give the target compound as a pale orange solid observed to be a pair of rotamers by NMR (65 mg, 0.17 mmol, 89%). Rf 0.42 (3:1 Hexanes:EtOAc); M.p. 106-108° C.; IR (cm$^{-1}$) 3003, 2979, 2962, 2934, 2836, 1793, 1737, 1715, 1610, 1511; $^1$H NMR (400 MHz, CDCl$_3$) 1.37 (5.4H, s, C(CH$_3$)$_{3\text{-}major}$), 1.55 (3.6H, s, C(CH$_3$)$_{3\text{-}minor}$), 3.77 (1.8H, s, OCH$_{3\text{-}major}$), 3.78 (1.2H, s, OCH$_{3\text{-}minor}$), 4.80 (0.8H, s, benzyl CH$_{2\text{-}minor}$), 4.83 (1.2H, s, benzyl CH$_{2\text{-}major}$), 6.82 (2H, dd, J=10.0, 8.5 Hz, H-4/7), 7.31 (2H, dd, J=10.0, 8.5 Hz, H-5/6), 7.72-7.77 (2H, m, benzyl H-3/5), 7.80-7.86 (2H, m, benzyl H-2/6); $^{13}$C NMR (100 MHz, CDCl$_3$) 27.9 (C(CH$_3$)$_{3\text{-}major}$), 28.2 (C(CH$_3$)$_{3\text{-}minor}$), 52.0 (benzyl-CH$_{2\text{-}major}$), 53.9 (benzyl-CH$_{2\text{-}minor}$), 55.2 (OCH$_3$), 82.4 (C(CH$_3$)$_{3\text{-}major}$), 83.2 (C(CH$_3$)$_{3\text{-}minor}$), 113.7 (Ar—C), 123.7 (Ar—C), 127.1 (Ar—C), 129.8 (Ar—C), 130.0 (Ar—C), 130.5 (Ar—C), 134.5 (Ar—C), 153.5 (C=O$_{minor}$), 159.3 (C=O$_{major}$), 165.0 (C=O$_{major}$), 165.4 (C=O$_{minor}$); MS [M+NH$_4$]$^+$ m/z 400.2.

General Procedure for the Removal of Phthlalimide Protecting Groups

Methylhydrazine (1.25 equiv.) was added to an ice cooled solution of phthalimide (1.0 equiv.) in THF (2 mL/mmol). The reaction mixture was allowed to warm to RT and was stirred for 18 h. The resultant white suspension was passed through a filter, and the filtrate was concentrated in vacuo. A mixture of Hexanes:EtOAc (3:1, 1 mL/mmol) was added, and the precipitate formed was removed via filtration. This process was repeated a further 2 times, and the final filtrate was concentrated to give the target compound.

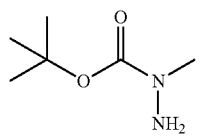

Synthesis of tert-butyl 1-methylhydrazine-1-carboxylate

Methylhydrazine (198 µL, 3.77 mmol) and tert-butyl (1,3-dioxoisoindolin-2-yl)(methyl)carbamate (0.833 g, 3.01 mmol) were reacted in THF (6 mL) according to the described general procedure. The target compound was obtained as a pale-yellow oil (0.338 g, 2.31 mmol, 77%). Rf 0.20 (1:1 Hexanes:EtOAc); IR (cm$^{-1}$) 3247, 2924, 2854, 1697, 1640, 1568; $^1$H NMR (400 MHz, CDCl$_3$) 1.47 (9H, s, C(CH$_3$)$_3$), 3.05 (3H, s, N—CH$_3$), 4.10 (2H, br s, NH$_2$).

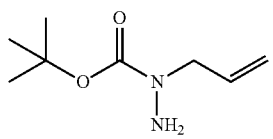

Synthesis of tert-butyl 1-allylhydrazine-1-carboxylate

Methylhydrazine (3.40 mL, 64.3 mmol) and tert-butyl alyl(1,3-dioxoisoindolin-2-yl)carbamate (15.6 g, 51.5 mmol) were reacted in THF (100 mL) according to the described general procedure. The target compound was obtained as a pale-yellow oil (8.47 g, 49.2 mmol, 96%). Rf 0.22 (4:1 Hexane:EtOAc); IR (cm$^{-1}$) 3336, 2977, 2932, 1690; $^1$H NMR (400 MHz, DMSO-d$_6$) 1.40 (9H, s, —C(CH$_3$)$_3$), 3.85 (2H, ddd, J=5.5, 1.4, 1.4 Hz, N—CH$_2$), 4.46 (2H, s, NH$_2$), 5.06-5.09 (1H, m, allyl C—H$^{trans}$), 5.11 (1H, br, allyl C—H$^{cis}$), 5.74-5.86 (1H, m, allyl C—H); $^{13}$C NMR (125 MHz, DMSO-d$_6$) 28.5 (C(CH$_3$)$_3$), 53.6 (N—CH$_2$), 79.4 (C(CH$_3$)$_3$), 116.2 (allyl-CH$_2$), 134.6 (allyl-CH), 156.5 (C=O).

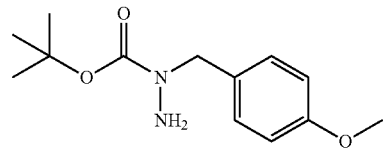 [SMILES: COc1ccc(CN(N)C(=O)OC(C)(C)C)cc1]

Synthesis of tert-butyl 1-(4-methoxybenzyl)hydrazine-1-carboxylate

Methylhydrazine (80 µL, 1.80 mmol) and tert-butyl (1,3-dioxoisoindolin-2-yl)(4-methoxybenzyl)carbamate (0.470 g, 1.44 mmol) were reacted in THF (3 mL) according to the described general procedure. Following purification on silica gel (4:1 Hexanes:EtoAc) the target compound was obtained as a pale yellow oil (0.275 g, 1.09 mmol, 76%). Rf 0.24 (4:1 Hexane:EtOAc); IR (cm$^{-1}$) 3336, 2975, 2933, 2836, 1688, 1612, 1511; $^1$H NMR (400 MHz, CDCl$_3$) 1.51 (9H, s, C(CH$_3$)$_3$), 3.81 (3H, s, OCH$_3$), 4.04 (2H, br s, NH$_2$), 4.50 (2H, s, N—CH$_2$), 6.88 (2H, d, J=8.4 Hz, H-3/5), 7.24 (2H, d, J=8.4 Hz, H-2/6); $^{13}$C NMR (100 MHz, CDCl$_3$) 28.5 (C(CH$_3$)$_3$), 53.7 (OCH$_3$), 55.3 (NCH$_2$), 80.7 (C(CH$_3$)$_3$), 113.9 (Ar—C), 129.3 (Ar—C), 130.0 (Ar—C), 156.8 (Ar—C), 159.0 (C=O); MS [M+H]$^+$ m/z 253.2.

General Procedure for the Synthesis of Pyrazolopyrimidinones

DIPEA (2.5 equiv.) and the relevant hydrazine (1.05 equiv.) were added to a solution of ethyl 4-chloro-2-methylthio-5-pyrimidinecarboxylate (1.0 equiv.) in THF (3 mL/mmol). The reaction mixture was heated at reflux for 72 h, before being concentrated in vacuo. Et$_2$O (1 mL/mmol) was added to the residue, and the resultant precipitate was collected by filtration. The filtrate was evaporated to dryness, and the residue was cooled in an ice bath, after which TFA (1 mL/mmol) was added. The resultant solution was stirred at RT for 1 h, followed by 70° C. for 1 h. The solvent was removed in vacuo and the residue was dissolved in EtOH (1 mL/mmol) and cooled in an ice bath, after which 6M NaOH (2 mL/mmol) was added. The resultant solution was stirred at RT for 15 min, before being acidified (pH 3) via the addition of conc. HCl. The solution was evaporated to dryness and the resultant residue was partitioned between chloroform (2 mL/mmol) and water (2 mL/mmol), and the organic phase was washed with brine (1 mL/mmol), dried (Mg$_2$SO$_4$), and concentrated in vacuo to afford the target compound.

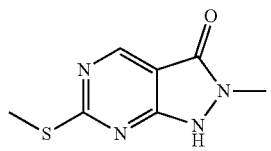

Synthesis of 1-(6-(2-hydroxypropan-2-yl)pyridin-2-yl)-2-methyl-6-(methylthio)-1,2-dihydro-3H-pyrazolo[3,4-d]pyrimidin-3-one Ethyl 4-chloro-2-methylthio-5-pyrimidinecarboxylate (0.480 g, 2.06 mmol), tert-butyl 1-methylhydrazine-1-carboxylate (0.316 g, 2.16 mmol) and DIPEA (1.87 mL, 10.7 mmol) were reacted in THF (6 mL) according to the described general procedure. Purification on KP—NH silica (4:1 DCM:MeOH) yielded the desired compound as a yellow solid (0.302 g, 1.54 mmol, 75%). Rf 0.23 (4:1 DCM:MeOH); M.p. 256-265° C. (decomposed); IR (cm$^{-1}$) 3336, 3024, 2940, 1683, 1638, 1587; $^1$H NMR (400 MHz, DMSO-d$_6$) 2.53 (3H, s, SCH$_3$), 3.36 (3H, s, N$^2$—CH$_3$), 8.68 (1H, s, H-4), 12.60 (1H, br s, N$^1$—H); $^{13}$C NMR (100 MHz, DMSO-d$_6$) 13.9 (SCH$_3$), 31.0 (N$^2$—CH$_3$), 103.8, 158.1; MS [M+H]$^+$ m/z 196.8.

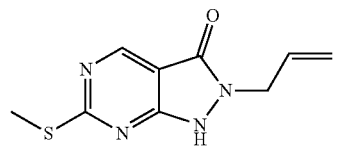

Synthesis of 2-allyl-6-(methylthio)-1,2-dihydro-3H-pyrazolo[3,4-d]pyrimidin-3-one Ethyl 4-chloro-2-methylthio-5-pyrimidinecarboxylate (11.1 g, 47.8 mmol), tert-butyl 1-allylhydrazine-1-carboxylate (8.64 g, 50.2 mmol) and DIPEA (20.8 mL, 120 mmol) were reacted in THF (150 mL) according to the described general procedure. Trituration with hexanes afforded the target compound as a yellow solid (5.44 g, 24.5 mmol, 51%). Rf 0.45 (9:1 DCM:MeOH); M.p. 125-128° C.; IR (cm$^{-1}$) 3032, 2979, 2926, 2659, 1656, 1615, 1566, 1514; $^1$H NMR (400 MHz, DMSO-d$_6$) 2.53 (3H, s, SCH$_3$), 4.38 (2H, d$_{app}$, J=5.2 Hz, N$^2$—CH$_2$), 5.06-5.20 (2H, m, allyl C—H$^{cis/trans}$), 5.87 (1H, ddt, J=17.2, 10.5, 5.3 Hz, alkene C—H), 8.67 (1H, s, H-4), 12.65 (1H, br, N$^1$—H); MS [M+H]$^+$ m/z 223.1.

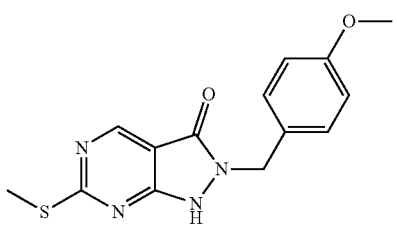

Synthesis of 2-(4-methoxybenzyl)-6-(methylthio)-1,2-dihydro-3H-pyrazolo[3,4-d]pyrimidin-3-one DIPEA (806 µL, 4.63 mmol) was added to a solution of ethyl 4-chloro-2-methylthio-5-pyrimidinecarboxylate (0.207 g, 0.89 mmol) and tert-butyl 1-(4-methoxybenzyl)hydrazine-1-carboxylate (0.235 g, 0.94 mmol) in THF (3 mL) and the reaction mixture was heated at reflux for 72 h. The solvent was removed in vacuo and the residue was partitioned between DCM (20 mL) and 0.1M HCl (15 mL) and the organic phase was washed with brine (10 mL) and dried (MgSO$_4$) before being concentrated in vacuo. The residue was dissolved in DCM (4 mL) and TFA (1.37 mL, 17.8 mmol) was added, with stirring at RT for 18 h. The solvent was removed in vacuo and the residue was taken up in DCM (20 mL) and washed with sat. NaHCO$_3$ (3×15 mL). The organic extract was washed with brine (10 mL) and dried (MgSO$_4$) before being evaporated to dryness. The residue was suspended in 0.5M NaOH (10 mL), and the mixture was refluxed with rapid stirring until the yellow oil residue entered solution after approximately 4 h. The solution was acidified to pH 2 (2M HCl), extracted with EtOAc (2×20 mL) before being dried (MgSO$_4$) and evaporated to dryness. The resultant residue was purified by chromatography on silica gel (9:1 DCM:MeOH) to afford the desired compound as a yellow solid (0.142 g, 0.47 mmol, 50%). Rf 0.41 (9:1 DCM:MeOH); M.p. 209-212° C.; IR (cm$^{-1}$) 3034, 2930, 1609, 1577, 1510; $^1$H NMR (400 MHz, CDCl$_3$) 2.53 (3H, s, SCH$_3$), 3.78 (3H, s, OCH$_3$), 5.03 (2H, s, N$^2$—CH$_2$), 6.84 (2H, d, J=8.5 Hz, benzyl H-3/5), 7.28 (2H, d, J=8.5 Hz, benzyl H-2/6), 8.66 (1H, s, H-4); $^{13}$C NMR (100 MHz, DMSO-d$_6$) 13.8 (SCH$_3$), 46.8 (N$^2$—CH$_2$), 55.5 (OCH$_3$), 103.7, 114.0, 114.1, 114.3, 129.5, 130.5, 158.3, 159.1; MS [M+H]$^+$ m/z 303.2.

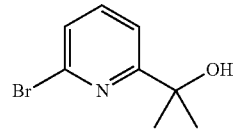

Synthesis of 2-(6-bromopyridin-2-yl)propan-2-ol

Methylmagnesium iodide (3M in Et$_2$O, 1.50 ml, 4.48 mmol) was added to a solution of methyl 6-bromopyridine-2-carboxylate (0.430 g, 1.99 mmol) in dry Et$_2$O (15 ml) under N$_2$. After 5 min at RT the reaction was quenched with 1M HCl (10 ml) and extracted with EtOAc (15 ml). The organic extract was washed with sat. NaHCO$_3$ solution (15 ml) and brine (10 ml), dried (MgSO$_4$) and concentrated in vacuo. The desired product was obtained as a yellow oil (0.365 g, 1.69 mmol, 85%). Rf 0.60 (1:1 Hexane:EtOAc); IR (cm$^{-1}$) 3420, 2975, 2930, 1731, 1701, 1580, 1553; $^1$H NMR (400 MHz, DMSO-d$_6$) 1.42 (6H, s, C(CH$_2$)$_2$), 5.33 (1H, s, OH), 7.47 (1H, dd, J=7.7, 0.9 Hz, H-5), 7.67 (1H, dd, J=7.7, 0.9 Hz, H-3), 7.73 (1H, dd, J=7.7, 7.7 Hz, H-4); $^{13}$C NMR (100 MHz, DMSO-d$_6$) 30.9 (C(CH$_2$)$_2$), 72.6 (C(CH$_2$)$_2$), 118.5 (Ar—C), 126.0 (Ar—C), 140.4 (Ar—C), 140.5 (Ar—C), 170.8 (Ar—C).

General Procedure for the Preparation of Pyridyl Pyrazolopyrimidinones

N,N'-Dimethylethylenediamine (2.0 equiv.) was added to a solution of the relevant pyrazolopyrimidine (1.0 equiv.), the relevant bromopyridine (1.3 equiv.), copper iodide (1.0 equiv.) and K$_2$CO$_3$ (1.4 equiv.) in 1,4-dioxane (2 mL/mmol) at 80° C. The resultant suspension was heated at 95° C. for 18 h, over which time a color change of orange to dark green occurred. The reaction mixture was cooled to RT and diluted with NH$_4$OH (10 ml) before being extracted with EtOAc (2×10 mL/mmol). The combined organic extracts were washed with brine (10 mL/mmol), dried (MgSO$_4$) and evaporated to dryness before the crude material was purified via chromatography on silica.

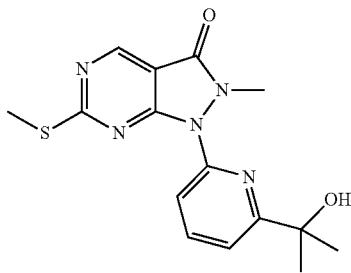 [SMILES: CSc1ncc2c(=O)n(C)n(-c3cccc(C(C)(C)O)n3)c2n1]

Synthesis of 1-(6-(2-hydroxypropan-2-yl)pyridin-2-yl)-2-methyl-6-(methylthio)-1,2-dihydro-3H-pyrazolo[3,4-d]pyrimidin-3-one 1-(6-(2-Hydroxypropan-2-yl)pyridin-2-yl)-2-methyl-6-(methylthio)-1,2-dihydro-3H-pyrazolo[3,4-d]pyrimidin-3-one (0.177 g, 0.90 mmol), 2-(6-bromopyridin-2-yl)propan-2-ol (0.253 g, 1.17 mmol), copper iodide (0.172 g, 0.90 mmol), K$_2$CO$_3$ (0.174 g, 1.26 mmol) and N,N'-dimethylethylenediamine (194 µL, 1.80 mmol) were reacted in 1,4-dioxane (2 mL) according to the described general procedure. Purification on silica gel (19:1 DCM:MeOH) gave the desired compound as a white solid (0.215 g, 0.65 mmol, 72%). Rf 0.34 (19:1 DCM:MeOH); M.p. 155-158° C.; IR (cm$^{-1}$) 3432, 2973, 2928, 1683, 1604, 1562; $^1$H NMR (400 MHz, DMSO-d$_6$) 1.46 (6H, s, C(CH$_3$)$_2$), 2.56 (3H, s, SCH$_3$), 3.49 (3H, s, N$^2$—CH$_3$), 5.35 (1H, s, OH), 7.67 (1H, d$_{app}$, J=7.7 Hz, H-5'), 7.79 (1H, d$_{app}$, J=8.2 Hz, H-3'), 8.06 (1H, dd$_{app}$, J=8.2, 7.7 Hz, H-4'), 9.00 (1H, s, H-4); $^{13}$C NMR (100 MHz, DMSO-d$_6$) 14.4 (SCH$_3$), 30.9 (C(CH$_3$)$_2$), 32.8 (N$^2$—CH$_3$), 72.8 (C(CH$_3$)$_2$), 104.8, 116.6, 117.5, 139.7, 146.8, 154.7, 158.3, 160.4, 168.4, 175.9; MS [M+H]$^+$ m/z 332.6.

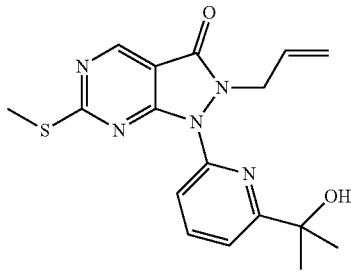 [SMILES: C=CCn1c(=O)c2cnc(SC)nc2n1-c1cccc(C(C)(C)O)n1]

Synthesis of 2-allyl-1-(6-(2-hydroxypropan-2-yl)pyridin-2-yl)-6-(methylthio)-1,2-dihydro-3H-pyrazolo[3,4-d]pyrimidin-3-one 2-Allyl-6-(methylthio)-1,2-dihydro-3H-pyrazolo[3,4-d]pyrimidin-3-one (0.500 g, 2.25 mmol), 2-(6-bromopyridin-2-yl)propan-2-ol (0.643 g, 2.93 mmol), copper iodide (0.428 g, 2.25 mmol), K$_2$CO$_3$ (0.435 g, 3.15 mmol) and N,N'-dimethylethylenediamine (266 µL, 4.47 mmol) were reacted in 1,4-dioxane (5 mL) according to the described general procedure. Purification on silica gel (1:1 Hexanes:EtOAc) gave the desired compound as a white solid (0.653 g, 1.82 mmol, 81%). Rf 0.63 (9:1 DCM:MeOH); M.p. 108-111° C.; IR (cm$^{-1}$) 3337, 3081, 2966, 2924, 1663, 1601, 1559; $^1$H NMR (400 MHz, CDCl$_3$) 1.61 (6H, s, C(CH$_3$)$_2$), 2.61 (3H, s, S—CH$_3$), 3.77 (1H, s, OH), 4.82 (2H, d$_{app}$, J=5.9 Hz, N$^2$—CH$_2$), 4.95 (1H, d$_{app}$, J=16.9 Hz, alkene C—H$^{trans}$), 5.08 (1H, d$_{app}$, J=10.3 Hz, alkene C—H), 5.72 (1H, ddt, J=16.9, 10.3, 5.9 Hz, alkene C—H), 7.42 (1H, d$_{app}$, J=7.7 Hz, H-5'), 7.78 (1H, d$_{app}$, J=8.0 Hz, H-3'), 7.93 (1H, dd, J=8.0, 7.7 Hz, H-4'), 8.96 (1H, s, H-4); $^{13}$C NMR (100 MHz, CDCl$_3$) 14.5 (SCH$_3$), 30.5 (C(CH$_3$)$_2$), 47.5 (N$^2$—CH$_2$), 72.5 (C(CH$_3$)$_2$), 116.4 (Ar—C), 116.6 (Ar—C), 119.3 (allyl-CH$_2$), 131.2, 139.2, 147.0 (Ar—C), 154.3 (Ar—C), 159.2 (C=O), 161.0 (Ar—C), 166.1 (Ar—C), 177.0 (Ar—C); MS [M+H]$^+$ m/z 359.3.

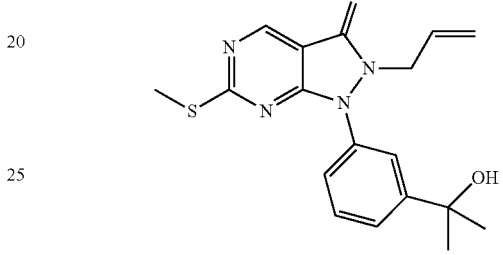

Synthesis of 2-allyl-1-(3-(2-hydroxypropan-2-yl)phenyl)-6-(methylthio)-1,2-dihydro-3H-pyrazolo[3,4-d]pyrimidin-3-one 2-Allyl-6-(methylthio)-1,2-dihydro-3H-pyrazolo[3,4-d]pyrimidin-3-one (0.200 g, 0.90 mmol), 2-(3-bromophenyl)propan-2-ol (0.252 g, 1.17 mmol), copper iodide (0.171 g, 0.90 mmol), K$_2$CO$_3$ (0.175 g, 1.26 mmol) and N,N'-dimethylethylenediamine (194 µL, 1.80 mmol) were reacted in 1,4-dioxane (2 mL) according to the described general procedure. Purification on silica gel (19:1 DCM:MeOH) gave the desired compound as a colorless oil (0.245 g, 0.68 mmol, 76%). Rf 0.26 (19:1 DCM:MeOH); IR (cm$^{-1}$) 3400, 3077, 2973, 2928, 2871, 1676, 1594, 1561; $^1$H NMR (400 MHz, CDCl$_3$) 1.64 (6H, s, C(CH$_3$)$_2$), 2.51 (3H, s, SCH$_3$), 4.45 (2H, d$_{app}$, J=6.0 Hz, N2-CH$_2$), 4.99 (1H, d$_{app}$, J=17.0, allyl C—H$^{trans}$), 5.14 (1H, d$_{app}$, J=10.2 Hz, allyl C—H), 5.71 (1H, ddt, J=17.0, 10.2, 6.0 Hz, allyl C—H), 7.29 (1H, d$_{app}$, J=7.2 Hz, H-6'), 7.47-7.56 (2H, m, H-4'/5'), 7.58 (1H, s$_{app}$, H-2'), 8.92 (1H, s, H-4); $^{13}$C NMR (100 MHz, CDCl$_3$) 14.3 (SCH$_3$), 31.9 (C(CH$_3$)$_2$), 46.2 (N$^2$—CH$_2$), 72.3 (C(CH$_3$)$_2$), 104.1, 119.4, 121.5, 123.2, 124.3, 129.3, 130.8, 135.4, 151.1, 154.3, 160.4, 161.6, 177.0; MS [M+H]$^+$ m/z 357.2.

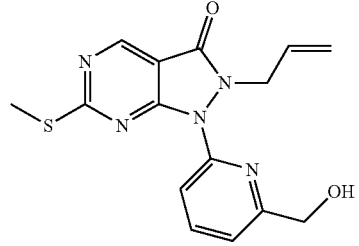 [SMILES: C=CCn1c(=O)c2cnc(SC)nc2n1-c1cccc(CO)n1]

Synthesis of 2-allyl-1-(6-(hydroxymethyl)pyridin-2-yl)-6-(methylthio)-1,2-dihydro-3H-pyrazolo[3,4-d]pyrimidin-3-one 2-Allyl-6-(methylthio)-1,2-dihydro-3H-pyrazolo[3,4-d]pyrimidin-3-one (0.200 g, 0.90 mmol), (6-bromopyridin-2-yl)methanol (0.220 g, 1.17 mmol), copper iodide (0.171 g, 0.90 mmol), K$_2$CO$_3$ (0.174 g, 1.26 mmol) and N,N'-dimethylethylenediamine (194 µL, 1.80 mmol) were reacted in 1,4-dioxane (2 mL) according to the described general procedure. Purification on silica gel (19:1 DCM:MeOH) gave the desired compound as a white solid (0.201 g, 0.61 mmol, 68%). Rf 0.23 (19:1 DCM:MeOH); M.p. 105-107° C.; IR (cm$^{-1}$) 3361, 3239, 2924, 2838, 1695, 1666, 1590, 1559; $^1$H NMR (400 MHz, CDCl$_3$) 2.60 (3H, s, SCH$_3$), 3.04 (1H, br, OH), 4.76-4.86 (4H, m, N$^2$—CH$_2$/CH$_2$OH), 4.97 (1H, d$_{app}$, J=17.1, allyl C—H$^{trans}$), 5.09 (1H, d$_{app}$, J=10.3 Hz, allyl C—H$^{cis}$), 5.73 (1H, ddt, J=17.1, 10.3, 6.2 Hz, allyl C—H), 7.30 (1H, d$_{app}$, J=8.0 Hz, H-5'), 7.80 (1H, d$_{app}$, J=8.1 Hz, H-3'), 7.92 (1H, dd$_{app}$, J=8.1, 8.0 Hz, H-4'), 8.96 (1H, s, H-4); $^{13}$C NMR (100 MHz, CDCl$_3$) 14.5 (SCH$_3$), 47.5 (N$^2$—CH$_2$), 64.4 (CH$_2$OH), 104.5, 117.0, 118.4, 119.3, 131.2, 138.9, 147.8, 154.3, 159.2, 161.0, 177.0; MS [M+H]$^+$ m/z 330.0.

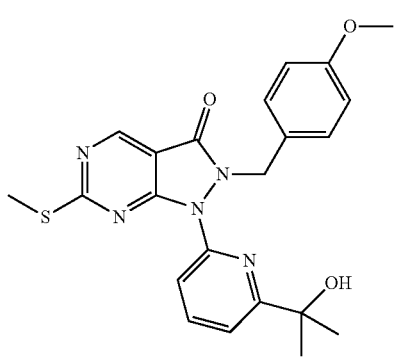

Synthesis of 1-(6-(2-hydroxypropan-2-yl)pyridin-2-yl)-2-(4-methoxybenzyl)-6-(methylthio)-1,2-dihydro-3H-pyrazolo[3,4-d]pyrimidin-3-one 2-(4-Methoxybenzyl)-6-(methylthio)-1,2-dihydro-3H-pyrazolo[3,4-d]pyrimidin-3-one (80 mg, 0.26 mmol), 2-(6-bromopyridin-2-yl)propan-2-ol (74 mg, 0.34 mmol), copper iodide (50 mg, 0.26 mmol), K$_2$CO$_3$ (50 mg, 0.37 mmol) and N,N'-dimethylethylenediamine (57 µL, 0.53 mmol) were reacted in 1,4-dioxane (1 mL) according to the described general procedure. Purification on silica gel (1:1 Hexanes:EtOAc) gave the desired compound as an off-white solid (84 mg, 0.19 mmol, 74%). Rf 0.26 (1:1 Hexanes:EtOAc); M.p. 143-145° C.; IR (cm$^{-1}$) 3349, 2972, 2929, 2829, 1691, 1601, 1560; $^1$H NMR (400 MHz, CDCl$_3$) 1.65 (6H, s, C(CH$_3$)$_2$), 2.55 (3H, s, SCH$_3$), 3.73 (3H, s, OCH$_3$), 5.34 (2H, s, N$^2$—CH$_2$), 6.68 (2H, d, J=8.4 Hz, benzyl H-3/5), 6.83 (2H, d, J=8.4 Hz, benzyl H2/6), 7.44 (1H, d$_{app}$, J=7.5 Hz, H-5'), 7.56 (1H, d$_{app}$, J=8.0 Hz, H-3'), 7.87 (1H, dd$_{app}$, J=8.0, 7.5 Hz, H-4'), 8.95 (1H, s, H-4); $^{13}$C NMR (100 MHz, CDCl$_3$) 14.4 (SCH$_3$), 30.6 (C(CH$_3$)$_2$), 47.9 (N$^2$—CH$_2$), 55.2 (OCH$_3$), 72.6 (C(CH$_3$)$_2$), 104.5, 114.0, 116.6, 127.3, 129.4, 139.2, 146.9, 154.3, 158.9, 159.4, 161.3, 166.1, 176.9; MS [M+H]$^+$ m/z 438.2.

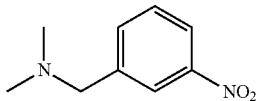

Synthesis of N,N-dimethyl-1-(3-nitrophenyl)methanamine

Triethylamine (1.94 mL, 13.8 mmol) was added dropwise to a solution of 3-nitrobenzylbromide (1.00 g, 4.63 mmol) and dimethylamine hydrochloride (0.755 g, 9.26 mmol) in DCM (10 mL). The resultant mixture was stirred at RT for 2 h, before being evaporated to dryness and the residue partitioned between EtOAc (50 mL) and water (30 mL). The organic phase was washed with brine (20 mL) and dried (MgSO$_4$), before being evaporated to dryness to give the target compound as yellow oil (0.601 g, 3.34 mmol, 72%). Rf 0.28 (1:1 Hexanes:EtOAc); IR (cm$^{-1}$) 2976, 2944, 2859, 2820, 2774, 1523; $^1$H NMR (400 MHz, CDCl$_3$) 2.28 (6H, s, N(CH$_3$)$_2$), 3.53 (2H, s, ArCH$_2$), 7.51 (1H, dd, J=8.0, 7.9 Hz, H-5), 7.68 (1H, d$_{app}$, J=7.9 Hz, H-6), 8.13 (1H, dd, J=8.0, 2.0 Hz, H-4), 8.21 (1H, S$_{app}$, H-2); $^{13}$C NMR (100 MHz, CDCl$_3$) 45.4 (N(CH$_3$)$_2$), 63.4 (NCH$_2$), 122.2 (Ar—C), 123.7 (Ar—C), 129.2 (Ar—C), 135.0 (Ar—C), 141.4 (Ar—C), 148.4 (Ar—C).

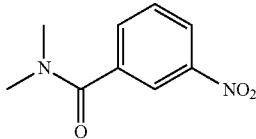

Synthesis of N,N-dimethyl-3-nitrobenzamide 1,1'-Carbonyldiimidazole (0.970 g, 5.98 mmol) and DIPEA (1.56 mL, 8.97 mmol) were added to a solution of 3-nitrobenzoic acid (0.500 g, 2.99 mmol) in dry DMF (20 mL). After stirring at RT for 2 h, dimethylamine hydrochloride (0.487 g, 5.98 mmol) was added and the resultant mixture was stirred at RT for a further 16 h. The solvent was removed in vacuo and the residue was dissolved in EtOAc (40 mL) and washed with saturated NaHCO$_3$ solution (30 mL) and 0.1M HCl (20 mL), followed by brine (20 mL) and drying (MgSO$_4$). The solvent was evaporated under vacuum to afford the desired compound as a pale-yellow oil/low-melting solid (0.468 g, 2.41 mmol, 81%). Rf 0.23 (1:1 Hexanes:EtOAc); IR (cm$^{-1}$) 3081, 3027, 2929, 2869, 1625, 1527; $^1$H NMR (400 MHz, CDCl$_3$) 3.01 (3H, s, NCH$_3$), 3.14 (3H, s, NCH$_3$), 7.62 (1H, dd$_{app}$, J=8.0, 7.8 Hz, H-5), 7.77 (1H, ddd, J=7.8, 1.3, 1.2 Hz, H-6), 8.24-8.29 (2H, m, H-2/4); $^{13}$C NMR (100 MHz, CDCl$_3$) 35.5 (NCH$_3$), 39.5 (NCH$_3$), 112.3 (Ar—C), 124.4 (Ar—C), 129.7 (Ar—C), 133.1 (Ar—C), 137.9 (Ar—C), 148.0 (Ar—C), 168.9 (C=O).

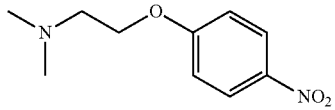

Synthesis of N,N-dimethyl-2-(4-nitrophenoxy)ethan-1-amine

Potassium carbonate (2.81 g, 2.03 mmol) and dimethylamine hydrochloride (1.65 g, 2.03 mmol) were added to a solution of 1-(2-bromoethoxy)-4-nitrobenzene (1.00 g, 4.10 mmol) in dry MeCN (3 mL) and the mixture was heated in a sealed tube at 80° C. for 2 h. The solvent was removed in vacuo and the crude residue was partitioned between DCM (50 mL) and water (50 mL). The organic phase was washed with water (50 mL) and brine (20 mL) before being dried (MgSO$_4$) and evaporated to dryness. The target compound was obtained as a yellow oil (0.860 g, 4.09, 100%). Rf 0.27 (19:1 DCM:MeOH); IR (cm$^{-1}$) 3114, 3084, 2945, 2824, 2774, 1737, 1591, 1508; $^1$H NMR (400 MHz, CDCl$_3$) 2.36 (6H, s, N(CH$_3$)$_2$), 2.78 (2H, t, J=5.6 Hz, OCH$_2$CH$_2$), 4.17 (2H, t, J=5.6 Hz, OCH$_2$CH$_2$), 6.99 (2H, d, J=9.2 Hz, H-2/6), 8.20 (2H, d, J=9.2 Hz, H-3/5); $^{13}$C NMR (100 MHz, CDCl$_3$) 45.9 (N(CH$_3$)$_2$), 57.9 (OCH$_2$CH$_2$), 66.8 (OCH$_2$CH$_2$), 114.5 (Ar—C), 125.9 (Ar—C), 141.6 (Ar—C), 163.8 (Ar—C).

General Procedure for the Reduction of Aromatic Nitro Groups with Iron Powder Iron powder (10.0 equiv.) was added to a solution of the relevant nitro aromatic (1.0 equiv.) in acetic acid (5 mL/mmol). The reaction mixture was stirred at 50° C. for 1 h, before being filtered through celite. The solvent was removed under reduced pressure and the residue was dissolved in EtOAc (10 mL/mmol) and washed with saturated NaHCO$_3$ solution (2×10 mL/mmol). The organic phase was washed with water (10 mL/mmol) and brine (5 mL/mmol) before being dried (MgSO$_4$) and concentrated in vacuo. The material was purified via chromatography if necessary.

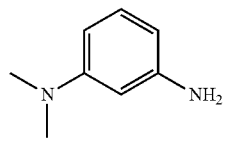

Synthesis of N$^1$,N$^1$-dimethylbenzene-1,3-diamine

N,N-Dimethyl-3-nitroaniline (0.500 g, 3.01 mmol) and iron powder (1.68 g, 30.1 mmol) were reacted in acetic acid (15 mL) according to the described general procedure. Purification on silica gel (1:1 Hexanes:EtOAc) afforded the target compound as a red oil (0.328 g, 2.40 mmol, 80%). Rf 0.44 (1:1 Hexanes:EtOAc); IR (cm$^{-1}$) 3343, 3220, 2878, 2800, 1606, 1579, 1501; $^1$H NMR (400 MHz, CDCl$_3$) 2.94 (6H, s, N(CH$_3$)$_2$), 3.62 (2H, br s, NH$_2$), 6.10-6.16 (2H, m, H-2/6), 6.24 (1H, dd, J=8.1, 2.3 Hz, H-4), 7.07 (1H, dd, J=8.1, 7.9 Hz, H-5); $^{13}$C NMR (100 MHz, CDCl$_3$) 40.6 (N(CH$_3$)$_2$), 99.6 (Ar—C), 103.8 (Ar—C), 104.3 (Ar—C), 129.9 (Ar—C), 147.3 (Ar—C), 151.9 (Ar—C).

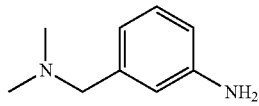

Synthesis of 3-((dimethylamino)methyl)aniline

N,N-dimethyl-1-(3-nitrophenyl)methanamine (0.579 g, 3.21 mmol) and iron powder (1.79 g, 32.1 mmol) were reacted in acetic acid (16 mL) according to the described general procedure. Purification on silica gel (19:1 DCM:MeOH) afforded the target compound as a pale red oil (0.347 g, 2.31 mmol, 72%). Rf 0.16 (19:1 DCM:MeOH); IR (cm$^{-1}$) 3270, 3147, 3079, 2974, 2942, 2858, 2816, 2774, 1666, 1610, 1552; $^1$H NMR (400 MHz, CDCl$_3$) 2.26 (6H, s, N(CH$_3$)$_2$), 3.35 (2H, s, ArCH$_2$), 3.65 (2H, br s, NH$_2$), 6.59-6.62 (1H, m, H-4), 6.69-6.72 (2H, m, H-2/6), 7.12 (1H, dd, J=8.0, 7.9 Hz, H-5); $^{13}$C NMR (100 MHz, CDCl$_3$) 45.3 (N(CH$_3$)$_2$), 64.1 (ArCH$_2$), 118.9 (Ar—C), 120.5 (Ar—C), 125.0 (Ar—C), 128.9 (Ar—C), 138.1 (Ar—C), 139.6 (Ar—C).

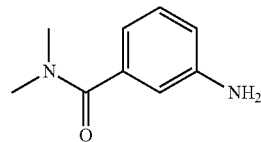

Synthesis of 3-amino-N,N-dimethylbenzamide

N,N-dimethyl-3-nitrobenzamide (0.455 g, 2.34 mmol) and iron powder (1.31 g, 23.4 mmol) were reacted in acetic acid (12 mL) according to the described general procedure. Purification on silica gel (1:1 Hexanes:EtOAc) afforded the target compound as an off-white solid (0.327 g, 1.99 mmol, 85%). Rf 0.26 (19:1 DCM:MeOH); M.p. 87-89° C.; IR (cm$^{-1}$) 3419, 3345, 3240, 2928, 2850, 1649, 1579; $^1$H NMR (400 MHz, CDCl$_3$) 2.99 (3H, s, NCH$_3$), 3.11 (3H, s, NCH$_3$), 3.76 (2H, br s, NH$_2$), 6.68-6.80 (3H, m, H-2/4/6), 7.18 (1H, dd, J=7.7, 7.6 Hz, H-5); $^{13}$C NMR (100 MHz, CDCl$_3$) 35.2 (NCH$_3$), 39.5 (NCH$_3$), 113.5 (Ar—C), 116.0 (Ar—C), 116.9 (Ar—C), 129.2 (Ar—C), 137.5 (Ar—C), 146.6 (Ar—C), 171.8 (C=O).

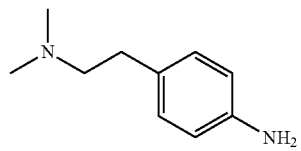

Synthesis of 4-(2-(dimethylamino)ethyl)aniline

To a solution of 4-nitrophenethyl bromide (1.02 g, 4.35 mmol) and dimethylamine hydrochloride (1.46 g, 17.4 mmol) in dry DCM (10 mL) was added triethylamine dropwise (3.00 mL, 21.5 mmol) and the reaction was stirred at RT for 16 h. The reaction mixture was concentrated in vacuo before the sample was partitioned between EtOAc (40 mL) and H$_2$O (30 mL). The aqueous phase was extracted with EtOAc (2×40 mL), and the combined organic extracts were dried (MgSO$_4$) and concentrated in vacuo. The crude nitro aromatic was dissolved in MeOH (30 mL) to which palladium on carbon was added (10% Pd, 0.150 g) and the mixture was stirred under H$_2$ at RT for 16 h. The catalyst was removed over celite and the solvent removed under reduced pressure. Purification of the crude material on silica gel (9:1

DCM:MeOH) yielded the target compound as a yellow oil (0.422 g, 2.57 mmol, 59%—2 steps). Rf 0.16 (9:1 DCM:MeOH); IR (cm$^{-1}$) 3317, 3018, 2771, 2705, 2448, 1612, 1518; $^1$H NMR (400 MHz, CDCl$_3$) 2.33 (6H, s, N(CH$_3$)$_2$), 2.50-2.55 (2H, m, ArCH$_2$CH$_2$), 2.68-2.73 (2H, m, ArCH$_2$CH$_2$), 3.55 (2H, br s, NH$_2$), 6.65 (2H, d, J=8.5 Hz, H-2/6), 7.01 (2H, d, J=8.5 Hz, H-3/5); $^{13}$C NMR (100 MHz, CDCl$_3$) 33.2 (ArCH$_2$CH$_2$), 45.3 (N(CH$_3$)$_2$), 61.8 (ArCH$_2$CH$_2$), 115.3 (Ar—C), 129.4 (Ar—C), 130.0 (Ar—C), 144.2 (Ar—C).

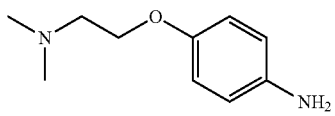

Synthesis of 4-(2-(dimethylamino)ethoxy)aniline

Palladium on carbon (10% Pd, 85 mg) was added to a solution of N,N-dimethyl-2-(4-nitrophenoxy)ethan-1-amine (854 mg, 4.06 mmol) in MeOH (40 mL). The reaction flask was evacuated under vacuum and backflushed with H$_2$, before being stirred for 16 hr at RT under a H$_2$ atmosphere. The catalyst was removed over celite and the solvent was removed in vacuo to afford the target compound as a brown oil (0.673 g, 3.74 mmol, 92%). Rf 0.38 (9:1 DCM:MeOH); IR (cm$^{-1}$) 3335, 3216, 2943, 2867, 2822, 2774, 1627, 1508; $^1$H NMR (400 MHz, CDCl$_3$) 2.35 (6H, s, N(CH$_3$)$_2$), 2.70 (2H, t, J=5.8 Hz, OCH$_2$CH$_2$), 3.47 (2H, br s, NH$_2$), 4.00 (2H, t, J=5.8 Hz, OCH$_2$CH$_2$), 6.64 (2H, d, J=8.8 Hz, H-3/5), 6.78 (2H, d, J=8.8 Hz, H-2/6); $^{13}$C NMR (100 MHz, CDCl$_3$) 45.8 (N(CH$_3$)$_2$), 58.4 (OCH$_2$CH$_2$), 66.6 (OCH$_2$CH$_2$), 115.8 (Ar—C), 116.4 (Ar—C), 140.1 (Ar—C), 152.0 (Ar—C).

General Procedure for the Preparation of Aniline Pyridyl Pyrazolopyrimidinones mCPBA (1.1 equiv.) was added to a solution of the appropriate pyrazolopyrimidinones (1.0 equiv.) in toluene (10 mL/mmol) and the resulting mixture was stirred at RT for 1 h. DIPEA (5.2 equiv.) and the relevant substituted aniline or amine (1.3 equiv.) were added, and the reaction mixture was stirred at RT for 18 h. Saturated NaHCO$_3$ solution (15 mL/mmol) was added, and the mixture was extracted with EtOAc (2×20 mL/mmol). The combined organic extracts were washed with brine (5 mL/mmol), dried (MgSO$_4$) and concentrated in vacuo. The resultant residues were purified via chromatography on silica to give the target compounds (12-89%).

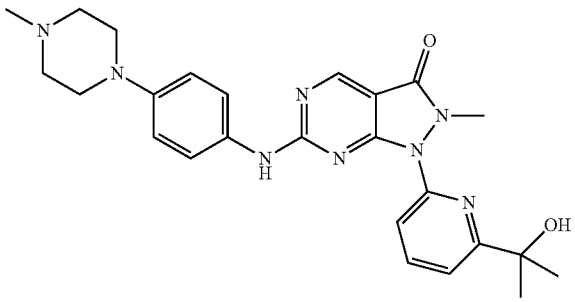 [SMILES: CN1CCN(c2ccc(Nc3ncc4c(=O)n(C)n(-c5cccc(C(C)(C)O)n5)c4n3)cc2)CC1]

Synthesis of 1-(6-(2-hydroxypropan-2-yl)pyridin-2-yl)-2-methyl-6-((4-(4-methylpiperazin-1-yl)phenyl)amino)-1,2-dihydro-3H-pyrazolo[3,4-d]pyrimidin-3-one (CM-185)

1-(6-(2-Hydroxypropan-2-yl)pyridin-2-yl)-2-methyl-6-(methylthio)-1,2-dihydro-3H-pyrazolo[3,4-d]pyrimidin-3-one (0.101 g, 0.29 mmol), mCPBA (70% w/w, 83 mg, 0.34 mmol), 4-methyl-1-(4-aminophenyl)piperazine (75 mg, 0.40 mmol) and DIPEA (275 μL, 1.58 mmol) were reacted in toluene (3 mL) according to the described general procedure. Purification via silica gel chromatography (9:1 DCM:MeOH) afforded the target compound as a yellow solid (0.16 mmol, 56%). Rf 0.39 (9:1 DCM:MeOH); M.p. 192-195° C.; IR (cm$^{-1}$) 3265, 3184, 3090, 2972, 2928, 2810, 1668, 1619, 1536, 1512; $^1$H NMR (400 MHz, DMSO-d$_6$) 1.46 (6H, s, C(CH$_3$)$_2$), 2.23 (3H, s, N(CH$_2$CH$_2$)$_2$NCH$_3$), 2.44-2.49 (4H, m, N(CH$_2$CH$_2$)$_2$NMe), 3.08-3.13 (4H, m, N(CH$_2$CH$_2$)$_2$NMe), 3.42 (3H, s, N$^2$—CH$_3$), 5.32 (1H, s, OH), 6.93 (2H, d, J=9.0 Hz, H-3"/5"), 7.59 (1H, d$_{app}$, J=7.9 Hz, H-5'), 7.62 (2H, d, J=9.0 Hz, H-2"/6"), 7.80 (1H, d$_{app}$, J=7.5 Hz, H-3'), 8.08 (1H, dd, J=7.9, 7.5 Hz, H-4'), 8.81 (1H, s, H-4). 10.11 (1H, br s, C$^6$—NH); $^{13}$C NMR (100 MHz, DMSO-d$_6$) 30.9 (C(CH$_3$)$_2$), 33.0 (N$^2$—CH$_3$), 46.3 (piperazine N—CH$_3$), 49.0 (piperazine-CH$_2$), 55.1 (piperazine-CH$_2$), 72.8 (C(CH$_3$)$_2$), 116.0, 116.7, 121.5, 131.4, 139.3, 147.6, 156.2, 160.9, 161.8, 168.1; MS [M+H]$^+$ m/z 475.2.

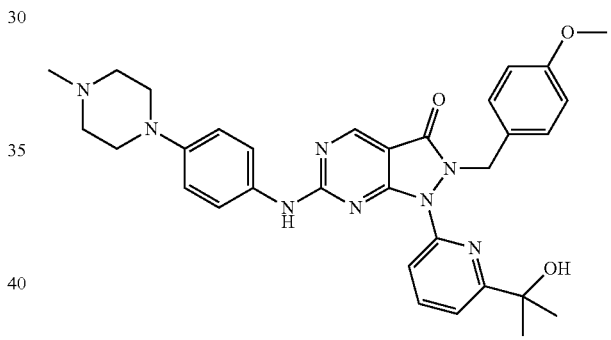

Synthesis of 1-(6-(2-hydroxypropan-2-yl)pyridin-2-yl)-2-(4-methoxybenzyl)-6-((4-(4-methylpiperazin-1-yl)phenyl)amino)-1,2-dihydro-3H-pyrazolo[3,4-d]pyrimidin-3-one (CM-188)

1-(6-(2-Hydroxypropan-2-yl)pyridin-2-yl)-2-(4-methoxybenzyl)-6-(methylthio)-1,2-dihydro-3H-pyrazolo[3,4-d]pyrimidin-3-one (0.156 g, 0.36 mmol), mCPBA (70% w/w, 98 mg, 0.39 mmol), 4-methyl-1-(4-aminophenyl)piperazine (87 mg, 0.46 mmol) and DIPEA (310 μL, 1.78 mmol) were reacted in toluene (4 mL) according to the described general procedure. Purification via silica gel chromatography (9:1 DCM:MeOH) afforded the target compound as a yellow solid (0.188 g, 0.32 mmol, 89%). Rf 0.46 (9:1 DCM:MeOH); M.p. 196-199° C.; IR (cm$^{-1}$) 3275, 3186, 2963, 2936, 2838, 1684, 1603, 1536, 1512; $^1$H NMR (400 MHz, CDCl$_3$) 1.64 (6H, s, C(CH$_3$)$_2$), 2.40 (3H, s, N—CH$_3$), 2.62-2.67 (4H, m, N—(CH$_2$CH$_2$)$_2$—NMe), 3.20-3.25 (4H, m, N—CH$_2$CH$_2$—NMe), 3.72 (3H, s, OCH$_3$), 5.29 (2H, s, N$^2$—CH$_2$), 6.67 (2H, d, J=8.6 Hz, benzyl H-2/6), 6.85 (2H, d, J=8.6 Hz, benzyl H-3/5), 6.91 (2H, d, J=8.7 Hz, H-3"/5"), 7.37 (1H, d$_{app}$, J=7.8 Hz, H-5'), 7.43 (2H, d, J=8.7 Hz, H-2"/6"), 7.57 (1H, d$_{app}$, J=8.1 Hz, H-3'), 7.82 (1H, dd, J=8.1, 7.8 Hz, H-4'), 8.83 (1H, s, H-4); $^{13}$C NMR (100 MHz, CDCl$_3$) 30.6 (C(CH$_3$)$_2$), 46.0 (N—CH$_3$), 48.1 (N$^2$—CH$_2$), 49.4 (piperazine-CH$_2$), 55.0 (OCH$_3$), 55.2 (piperazine-CH$_2$), 72.5 (C(CH$_3$)$_2$), 113.9, 116.0, 116.3, 116.5, 122.1, 127.7, 129.5, 130.4, 138.8, 147.4, 148.1, 156.3, 159.2, 161.0, 162.5, 165.8; MS [M+H]$^+$ m/z 581.4.

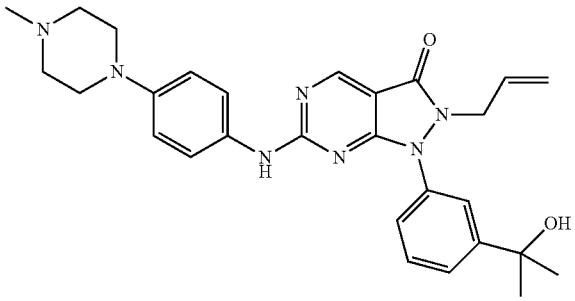 [SMILES: C=CCn1c(=O)c2cnc(Nc3ccc(N4CCN(C)CC4)cc3)nc2n1-c1cccc(C(C)(C)O)c1]

Synthesis of 2-allyl-1-(3-(2-hydroxypropan-2-yl) phenyl)-6-((4-(4-methylpiperazin-1-yl)phenyl) amino)-1,2-dihydro-3H-pyrazolo[3,4-d]pyrimidin-3-one (CM-169)

2-Allyl-1-(3-(2-hydroxypropan-2-yl)phenyl)-6-(methylthio)-1,2-dihydro-3H-pyrazolo[3,4-d]pyrimidin-3-one (60 mg, 0.17 mmol), mCPBA (70% w/w, 46 mg, 0.19 mmol), 4-methyl-1-(4-aminophenyl)piperazine (42 mg, 0.22 mmol) and DIPEA (155 μL, 0.88 mmol) were reacted in toluene (2 mL) according to the described general procedure. Purification via silica gel chromatography (9:1 DCM:MeOH) afforded the target compound as a pale yellow solid (53 mg, 0.11 mmol, 64%). Rf 0.39 (9:1 DCM:MeOH); M.p. 164-167° C.; IR (cm$^{-1}$) 3287, 2972, 2935, 2838, 2798, 1701, 1668, 1606, 1542, 1512; $^1$H NMR (400 MHz, CDCl$_3$) 1.64 (6H, s, C(CH$_3$)$_2$), 2.39 (3H, s, N—CH$_3$), 2.60-2.64 (4H, m, N—(CH$_2$CH$_2$)$_2$—NMe), 3.18-3.23 (4H, m, N—CH$_2$CH$_2$—NMe), 4.40 (2H, d$_{app}$, J=6.1 Hz, N$^2$—CH$_2$), 5.00 (1H, d$_{app}$, J=17.2, alkene C—H$^{trans}$), 5.12 (1H, d$_{app}$, J=10.1 Hz, alkene C—H$^{cis}$), 5.73 (1H, ddt, J=17.2, 10.1, 6.1 Hz, alkene C—H), 6.90 (2H, d, J=8.8 Hz, H-3"/5"), 7.29-7.34 (1H, m, H-5'), 7.45 (2H, d, J=8.8 Hz, H-2"/6"), 7.49 (2H, d$_{app}$, J=4.8 Hz, H-4'/6'), 7.60 (1H, S$_{app}$, H-2'), 8.83 (1H, s, H-4); $^{13}$C NMR (100 MHz, CDCl$_3$) 31.9 (C(CH$_3$)$_2$), 46.1 (N—CH$_3$), 46.5 (N$^2$—CH$_2$), 49.4 (piperazine-CH$_2$), 55.0 (piperazine-CH$_2$), 72.4 (C(CH$_3$)$_2$), 116.6, 119.2, 123.7, 129.1, 130.7, 131.1, 136.2, 150.9, 156.3, 162.7; MS [M+H]$^+$ m/z 500.2.

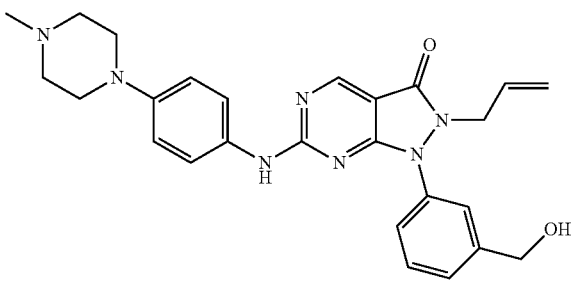 [SMILES: C=CCn1c(=O)c2cnc(Nc3ccc(N4CCN(C)CC4)cc3)nc2n1-c1cccc(CO)c1]

Synthesis of 2-allyl-1-(6-(hydroxymethyl)pyridin-2-yl)-6-((4-(4-methylpiperazin-1-yl)phenyl)amino)-1,2-dihydro-3H-pyrazolo[3,4-d]pyrimidin-3-one (CM-170)

2-Allyl-1-(6-(hydroxymethyl)pyridin-2-yl)-6-(methylthio)-1,2-dihydro-3H-pyrazolo[3,4-d]pyrimidin-3-one (0.156 g, 0.47 mmol), mCPBA (70% w/w, 0.127 g, 0.52 mmol), 4-methyl-1-(4-aminophenyl)piperazine (0.117 g, 0.61 mmol) and DIPEA (425 μL, 2.44 mmol) were reacted in toluene (5 mL) according to the described general procedure. Purification via silica gel chromatography (9:1 DCM:MeOH) afforded the target compound as a yellow solid (0.134 g, 0.29 mmol, 61%). Rf 0.34 (9:1 DCM:MeOH); M.p. 197-200° C.; IR (cm$^{-1}$) 3253, 3176, 3065, 2939, 2818, 1687, 1674, 1610; $^1$H NMR (400 MHz, CDCl$_3$) 2.39 (3H, s, N—CH$_3$), 2.59-2.64 (4H, m, N—(CH$_2$CH$_2$)$_2$—NMe), 3.19-3.25 (4H, m, N—CH$_2$CH$_2$—NMe), 4.73 (2H, d$_{app}$, J=6.0 Hz, N$^2$—CH$_2$), 4.82 (2H, s, CH$_2$OH), 4.98 (1H, d$_{app}$, J=17.2, alkene C—H$^{trans}$), 5.07 (1H, d$_{app}$, J=10.2 Hz, alkene C—H$^{cis}$), 5.73 (1H, ddt, J=17.2, 10.2, 6.0 Hz, alkene C—H), 6.94 (2H, d, J=8.6 Hz, H-3"/5"), 7.24 (1H, dapp, J=7.5 Hz, H-5'), 7.47 (2H, d, J=8.6 Hz, H-2"/6"), 7.77 (1H, d$_{app}$, J=8.1 Hz, H-3'), 7.87 (1H, dd, J=8.1, 7.5 Hz, H-4'), 8.84 (1H, s, H-4); $^{13}$C NMR (100 MHz, CDCl$_3$) 46.1 (N—CH$_3$), 47.8 (N2-CH$_2$), 49.5 (piperazine-CH$_2$), 55.1 (piperazine-CH$_2$), 64.3 (CH$_2$OH), 116.4, 116.7, 117.8, 119.1, 122.0, 130.4, 131.6, 138.6, 148.2, 148.4, 156.3, 158.9, 161.4, 162.4; MS [M+H]$^+$ m/z 473.2.

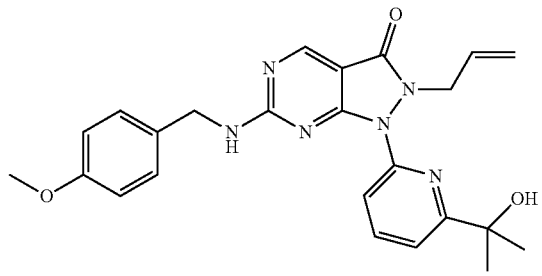 [SMILES: C=CCn1c(=O)c2cnc(NCc3ccc(OC)cc3)nc2n1-c1cccc(C(C)(C)O)n1]

Synthesis of 2-allyl-1-(6-(2-hydroxypropan-2-yl) pyridin-2-yl)-6-((4-methoxybenzyl)amino)-1,2-dihydro-3H-pyrazolo[3,4-d]pyrimidin-3-one (KAC-011)

2-Allyl-1-(6-(2-hydroxypropan-2-yl)pyridin-2-yl)-6-(methylthio)-1,2-dihydro-3H-pyrazolo[3,4-d]pyrimidin-3-one (0.203 g, 0.56 mmol), mCPBA (70% w/w, 0.157 g, 0.62 mmol), 4-methoxybenzylamine (95 μL, 0.73 mmol) and DIPEA (0.50 mL, 2.91 mmol) were reacted in toluene (5 mL) according to the described general procedure. Purification via silica gel chromatography (19:1 DCM:MeOH) afforded the target compound as an off-white solid (55 mg, 0.12 mmol, 22%). Rf 0.38 (19:1 DCM:MeOH); M.p. 136-138° C.; IR (cm$^{-1}$) 3442, 3219, 2972, 2922, 1667, 1614, 1593, 1546; $^1$H NMR (400 MHz, CDCl$_3$) 1.60 (6H, s, C(CH$_3$)$_2$), 3.82 (3H, s, OCH$_3$), 3.98 (1H, s, OH), 4.55-4.61 (2H, m, NHCH$_2$), 4.71-4.78 (2H, m, N$^2$—CH$_2$), 4.96 (1H, d$_{app}$, J=16.4 Hz, alkene C—H$^{trans}$), 5.06 (1H, d$_{app}$, J=9.9 Hz, alkene C—H$^{cis}$), 5.72 (1H, ddt, J=16.4, 9.9, 6.2 Hz, alkene C—H), 6.89 (2H, d, J=8.5 Hz, benzyl H-3/5), 7.26 (2H, d, J=8.5 Hz, benzyl H-2/6), 7.33 (1H, d$_{app}$, J=7.7 Hz, H-5'), 7.73 (1H, d$_{app}$, J=8.1 Hz, H-3'), 7.85 (1H, dd$_{app}$, J=8.1, 7.7 Hz, H-4'), 8.73 (1H, s, H-4); $^{13}$C NMR (100 MHz, CDCl$_3$) 30.5 (C(CH$_3$)$_2$), 42.3 (benzyl CH$_2$), 47.8 (N$^2$—CH$_2$), 55.3 (OCH$_3$), 72.4 (C(CH$_3$)$_2$), 114.1, 115.7, 115.9, 119.0, 129.0, 130.0, 131.7, 138.8, 147.6, 156.3, 159.2, 161.6, 162.7, 163.4, 166.6; MS [M+H]$^+$ m/z 447.4.

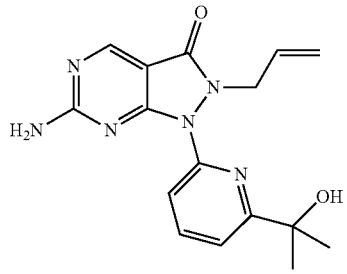 [SMILES: C=CCn1c(=O)c2cnc(N)nc2n1-c1cccc(C(C)(C)O)n1]

Synthesis of 2-allyl-6-amino-1-(6-(2-hydroxypropan-2-yl)pyridin-2-yl)-1,2-dihydro-3H-pyrazolo[3,4-d]pyrimidin-3-one (KAC-030)

2-Allyl-1-(6-(2-hydroxypropan-2-yl)pyridin-2-yl)-6-(methylthio)-1,2-dihydro-3H-pyrazolo[3,4-d]pyrimidin-3-one (50 mg, 0.14 mmol), mCPBA (70% w/w, 32 mg, 0.15 mmol) and ammonia (2M in EtOH, 0.35 mL, 0.70 mmol) were reacted in toluene (2 mL) according to the described general procedure. Purification via KP—NH silica chromatography (19:1 DCM:MeOH) afforded the target compound as a white solid (13 mg, 0.04 mmol, 29%). Rf 0.53 (KP—NH—19:1 DCM:MeOH); M.p. 195-197° C.; IR (cm$^{-1}$) 3325, 3187, 2979, 2924, 2856, 1667, 1649, 1616, 1563; $^1$H NMR (400 MHz, DMSO-d$_6$) 1.46 (6H, s, C(CH$_3$)$_2$), 4.62 (2H, d$_{app}$, J=5.6 Hz, N$^2$—CH$_2$), 4.81 (1H, d$_{app}$, J=17.1 Hz, alkene C—H$^{trans}$), 4.98 (1H, d$_{app}$, J=10.0 Hz, alkene C—H$^{cis}$), 5.32 (1H, s, OH), 5.64 (1H, ddt, J=17.1, 10.0, 5.6 Hz, alkene C—H), 7.53 (2H, br s, NH$_2$), 7.59 (1H, d$_{app}$, J=7.7 Hz, H-5'), 7.71 (1H, d$_{app}$, J=8.1 Hz, H-3'), 7.95 (1H, d$_{app}$, J=8.1, 7.7 Hz, H-4'), 8.70 (1H, s, H-4); $^{13}$C NMR (100 MHz, DMSO-d$_6$) 30.9 (C(CH$_3$)$_2$), 47.1 (N$^2$—CH$_2$), 72.8 (C(CH$_3$)$_2$), 98.9, 116.4, 116.6, 118.6, 132.7, 139.2, 147.8, 156.8, 161.9, 162.0, 165.4, 168.0; MS [M+H]$^+$ m/z 327.2.

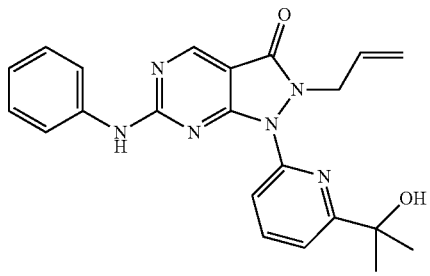 [SMILES: C=CCn1c(=O)c2cnc(Nc3ccccc3)nc2n1-c1cccc(C(C)(C)O)n1]

Synthesis of 2-allyl-1-(6-(2-hydroxypropan-2-yl)pyridin-2-yl)-6-(phenylamino)-1,2-dihydro-3H-pyrazolo[3,4-d]pyrimidin-3-one (KAC-017)

2-Allyl-1-(6-(2-hydroxypropan-2-yl)pyridin-2-yl)-6-(methylthio)-1,2-dihydro-3H-pyrazolo[3,4-d]pyrimidin-3-one (0.101 g, 0.28 mmol), mCPBA (70% w/w, 77 mg, 0.31 mmol), aniline (33 μL, 0.36 mmol) and DIPEA (0.25 mL, 1.45 mmol) were reacted in toluene (3 mL) according to the described general procedure. Purification via silica gel chromatography (19:1 DCM:MeOH) afforded the target compound as a white solid (35 mg, 0.09 mmol, 31%). Rf 0.50 (19:1 DCM:MeOH); M.p. 153-155° C.; IR (cm$^{-1}$) 3245, 3191, 3080, 3056, 2975, 2929, 1671, 1615, 1540; $^1$H NMR (400 MHz, CDCl$_3$) 1.61 (6H, s, C(CH$_3$)$_2$), 3.97 (1H, s, OH), 4.78 (2H, d$_{app}$, J=6.2 Hz, N$^2$—CH$_2$), 4.96 (1H, dd, J=17.0, 1.1 Hz, alkene C—H$^{trans}$), 5.07 (1H, dd, J=10.2, 1.1 Hz, alkene C—H), 5.73 (1H, ddt, J=17.0, 10.2, 6.2 Hz, alkene C—H), 7.15 (1H, dd, J=7.4, 7.3 Hz, H-4"), 7.36-7.41 (3H, m, H-5'/3"/5"), 7.63 (2H, d$_{app}$, J=7.8 Hz, H-2"/6"), 7.79 (1H, d$_{app}$, J=7.9 Hz, H-3'), 7.91 (1H, dd$_{app}$, J=7.9, 7.8 Hz, H-4'), 8.90 (1H, s, H-4); $^{13}$C NMR (100 MHz, CDCl$_3$) 30.6 (C(CH$_3$)$_2$), 47.6 (N$^2$—CH$_2$), 72.5 (C(CH$_3$)$_2$), 101.1, 116.2, 116.3, 119.1, 120.6, 124.0, 128.9, 131.5, 138.2, 138.9, 147.4, 156.3, 161.0, 161.3, 162.0, 165.9; MS [M+H]$^+$ m/z 403.4.

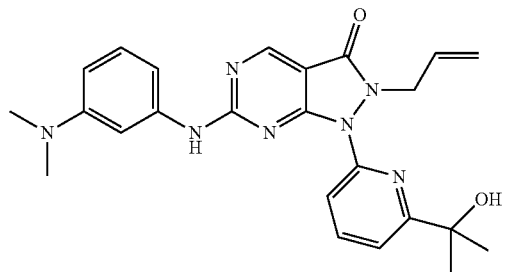 [SMILES: C=CCn1c(=O)c2cnc(Nc3cccc(N(C)C)c3)nc2n1-c1cccc(C(C)(C)O)n1]

Synthesis of 2-allyl-6-((3-(dimethylamino)phenyl)amino)-1-(6-(2-hydroxypropan-2-yl)pyridin-2-yl)-1,2-dihydro-3H-pyrazolo[3,4-d]pyrimidin-3-one (KAC-019)

2-Allyl-1-(6-(2-hydroxypropan-2-yl)pyridin-2-yl)-6-(methylthio)-1,2-dihydro-3H-pyrazolo[3,4-d]pyrimidin-3-one (0.102 g, 0.28 mmol), mCPBA (70% w/w, 80 mg, 0.31 mmol), N$^1$,N$^1$-dimethylbenzene-1,3-diamine (68 mg, 0.36 mmol) and DIPEA (0.25 mL, 1.45 mmol) were reacted in toluene (3 mL) according to the described general procedure. Purification via silica gel chromatography (19:1 DCM:MeOH) afforded the target compound as a pale yellow/green solid (29 mg, 0.06 mmol, 23%). Rf 0.30 (19:1 DCM:MeOH); M.p. 81-84° C.; IR (cm$^{-1}$) 3407, 3219, 3080, 2963, 2926, 1694, 1605, 1572, 1548; $^1$H NMR (400 MHz, CDCl$_3$) 1.61 (6H, s, C(CH$_3$)$_2$), 2.95 (6H, s, N(CH$_3$)$_2$), 3.92 (1H, s, OH), 4.76 (2H, d$_{app}$, J=6.0 Hz, N$^2$—CH$_2$), 4.95 (1H, d$_{app}$, J=17.2 Hz, alkene C—H$^{trans}$), 5.06 (1H, d$_{app}$, J=10.1 Hz, alkene C—H$^{cis}$), 5.73 (1H, ddt, J=17.2, 10.1, 6.0 Hz, alkene C—H), 6.54 (1H, dd, J=8.4, 2.0 Hz, H-4"), 6.87 (1H, br s, H-2"), 7.05 (1H, d$_{app}$, J=7.9 Hz, H-6"), 7.23 (1H, dd, J=8.4, 7.9 Hz, H-5"), 7.37 (1H, d$_{app}$, J=7.6 Hz, H-5'), 7.50 (1H, br s, N—H), 7.81 (1H, d$_{app}$, J=7.9 Hz, H-3'), 7.87 (1H, dd$_{app}$, J=7.9, 7.6 Hz, H-4'), 8.88 (1H, s, H-4); $^{13}$C NMR (100 MHz, CDCl$_3$) 30.5 (C(CH$_3$)$_2$), 40.6 (N(CH$_3$)$_2$), 47.6 (N$^2$—CH$_2$), 72.5 (C(CH$_3$)$_2$), 101.0, 104.8, 108.7, 109.2, 116.1, 116.5, 119.0, 129.4, 131.6, 138.9, 139.0, 147.5, 151.3, 156.3, 161.2, 161.4, 162.1, 165.9; MS [M+H]$^+$ m/z 446.2.

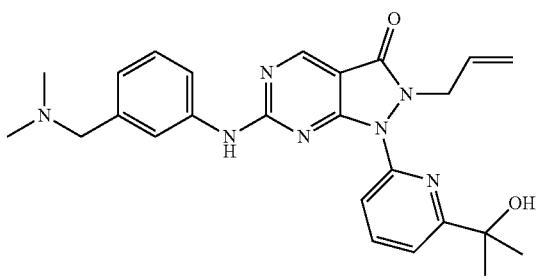 [SMILES: C=CCn1c(=O)c2cnc(Nc3cccc(CN(C)C)c3)nc2n1-c1cccc(C(C)(C)O)n1]

Synthesis of 2-allyl-6-((3-((dimethylamino)methyl)phenyl)amino)-1-(6-(2-hydroxypropan-2-yl)pyridin-2-yl)-1,2-dihydro-3H-pyrazolo[3,4-d]pyrimidin-3-one (KAC-014)

2-Allyl-1-(6-(2-hydroxypropan-2-yl)pyridin-2-yl)-6-(methylthio)-1,2-dihydro-3H-pyrazolo[3,4-d]pyrimidin-3-one (0.103 g, 0.28 mmol), mCPBA (70% w/w, 80 mg, 0.31 mmol), 3-((dimethylamino) methyl)aniline (60 mg, 0.36 mmol) and DIPEA (0.25 mL, 1.45 mmol) were reacted in toluene (3 mL) according to the described general procedure. Purification via silica gel chromatography (EtOAc) afforded the target compound as an off-white solid (35 mg, 0.08 mmol, 27%). Rf 0.18 (EtOAc); M.p. 121-123° C.; IR (cm$^{-1}$) 3407, 3230, 2975, 2927, 2772, 1665, 1610, 1542; $^1$H NMR (400 MHz, CDCl$_3$) 1.61 (6H, s, C(CH$_3$)$_2$), 2.29 (6H, s, N(CH$_3$)$_2$), 3.47 (2H, s, ArCH$_2$), 4.78 (2H, d$_{app}$, J=6.1 Hz, N$^2$—CH$_2$), 4.96 (1H, d$_{app}$, J=17.1 Hz, alkene C—H$^{trans}$), 5.07 (1H, d$_{app}$, J=10.1 Hz, alkene C—H), 5.73 (1H, ddt, J=17.1, 10.1, 6.1 Hz, alkene C—H), 7.10 (1H, d$_{app}$, J=7.5 Hz, H-4"), 7.33 (1H, dd$_{app}$, J=7.9, 7.5 Hz, H-5"), 7.39 (1H, d$_{app}$, J=7.6 Hz, H-5'), 7.54-7.62 (2H, m, H-2"/6"), 7.82 (1H, d$_{app}$, J=7.9 Hz, H-3'), 7.92 (1H, dd$_{app}$, J=7.9, 7.6 Hz, H-4'), 8.89 (1H, s, H-4); $^{13}$C NMR (100 MHz, CDCl$_3$) 30.5 (C(CH$_3$)$_2$), 45.4 (N(CH$_3$)$_2$), 47.6 (N$^2$—CH$_2$), 64.3 (Ar—CH$_2$), 72.5 (C(CH$_3$)$_2$), 101.2, 116.1, 116.4, 119.1, 119.2, 120.8, 124.6, 128.8, 131.6, 138.3, 138.9, 139.7, 147.4, 156.3, 161.1, 161.2, 162.0, 165.9; MS [M+H]$^+$ m/z 460.0.

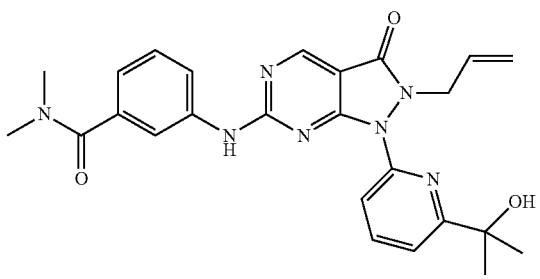 [SMILES: C=CCn1c(=O)c2cnc(Nc3cccc(C(=O)N(C)C)c3)nc2n1-c1cccc(C(C)(C)O)n1]

Synthesis of 3-((2-allyl-1-(6-(2-hydroxypropan-2-yl)pyridin-2-yl)-3-oxo-2,3-dihydro-1H-pyrazolo[3,4-d]pyrimidin-6-yl)amino)-N,N-dimethylbenzamide (KAC-016)

2-Allyl-1-(6-(2-hydroxypropan-2-yl)pyridin-2-yl)-6-(methylthio)-1,2-dihydro-3H-pyrazolo[3,4-d]pyrimidin-3-one (0.104 g, 0.28 mmol), mCPBA (70% w/w, 80 mg, 0.31 mmol), 3-amino-N,N-dimethylbenzamide (60 mg, 0.36 mmol) and DIPEA (0.25 mL, 1.45 mmol) were reacted in toluene (3 mL) according to the described general procedure. Purification via silica gel chromatography (19:1 DCM:MeOH) afforded the target compound as a white solid (16 mg, 0.03 mmol, 12%). Rf 0.34 (19:1 DCM:MeOH); M.p. 93-96° C.; IR (cm$^{-1}$) 3405, 3270, 2972, 2929, 1673, 1615, 1541; $^1$H NMR (400 MHz, CDCl$_3$) 1.60 (6H, s, C(CH$_3$)$_2$), 2.97 (3H, s, NCH$_3$), 3.16 (3H, s, NCH$_3$), 3.97 (1H, s, OH), 4.79 (2H, d$_{app}$, J=6.0 Hz, N$^2$—CH$_2$), 4.95 (1H, d$_{app}$, J=17.0 Hz, alkene C—H$^{trans}$), 5.06 (1H, d$_{app}$, J=10.3 Hz, alkene C—H), 5.72 (1H, ddt, J=17.0, 10.3, 6.0 Hz, alkene C—H), 7.14 (1H, d$_{app}$, J=7.5 Hz, H-4"), 7.35-7.41 (2H, m, H-5'/5"), 7.48 (1H, d$_{app}$, J=8.1 Hz, H-6"), 7.82 (1H, d$_{app}$, J=8.1 Hz, H-3'), 7.94 (1H, br s, N—H), 7.98-8.05 (2H, m, H-4'/2"), 8.89 (1H, s, H-4); $^{13}$C NMR (100 MHz, CDCl$_3$) 30.5 ((C(CH$_3$)$_2$), 35.4 (NCH$_3$), 39.6 (NCH$_3$), 47.6 N$^2$—CH$_2$), 72.5 (C(CH$_3$)$_2$), 101.5, 116.3, 116.6, 118.8, 119.1, 120.9, 121.9, 128.9, 131.5, 137.2, 138.6, 139.6, 147.2, 156.4, 160.8, 161.0, 161.8, 165.8, 171.2; MS [M+H]$^+$ m/z 474.2.

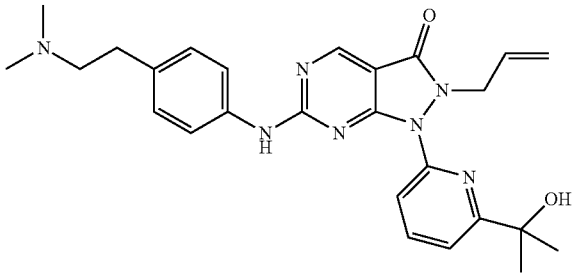 [SMILES: C=CCn1c(=O)c2cnc(Nc3ccc(CCN(C)C)cc3)nc2n1-c1cccc(C(C)(C)O)n1]

Synthesis of 2-allyl-6-((4-(2-(dimethylamino)ethyl)phenyl)amino)-1-(6-(2-hydroxypropan-2-yl)pyridin-2-yl)-1,2-dihydro-3H-pyrazolo[3,4-d]pyrimidin-3-one (KAC-034)

2-Allyl-1-(6-(2-hydroxypropan-2-yl)pyridin-2-yl)-6-(methylthio)-1,2-dihydro-3H-pyrazolo[3,4-d]pyrimidin-3-one (0.150 g, 0.42 mmol), mCPBA (70% w/w, 0.114 g, 0.46 mmol), 4-(2-(dimethylamino) ethyl)aniline (90 mg, 0.55 mmol) and DIPEA (0.38 mL, 2.18 mmol) were reacted in toluene (4 mL) according to the described general procedure. Purification via KP—NH silica chromatography (19:1 DCM:MeOH) afforded the target compound as an off-white solid (36 mg, 0.08 mmol, 18%). Rf 0.14 (9:1 DCM:MeOH); M.p. 116-119° C.; IR (cm$^{-1}$) 3252, 3191, 3099, 2968, 2929, 2855, 2827, 2782, 1745, 1672, 1603, 1568; $^1$H NMR (400 MHz, CDCl$_3$) 1.61 (6H, s, C(CH$_3$)$_2$), 2.33 (6H, s, N(CH$_3$)$_2$), 2.53-2.59 (2H, m, ArCH$_2$CH$_2$), 2.76-2.82 (2H, m, ArCH$_2$CH$_2$), 4.77 (2H, d$_{app}$, J=5.8 Hz, N$^2$—CH$_2$), 4.96 (1H, d$_{app}$, J=17.2 Hz, alkene C—H$^{trans}$), 5.06 (1H, d$_{app}$, J=10.3 Hz, alkene C—H$^{cis}$), 5.73 (1H, ddt, J=17.2, 10.3, 5.8 Hz, alkene C—H), 7.21 (2H, d, J=8.2 Hz, H-3"/5"), 7.39 (1H, d$_{app}$, J=7.7 Hz, H-5'), 7.53 (2H, d, J=8.2 Hz, H-2"/6"), 7.78 (1H, d$_{app}$, J=7.9 Hz, H-3'), 7.90 (1H, dd, J=7.9, 7.7 Hz, H-4'), 8.87 (1H, s, H-4); $^{13}$C NMR (100 MHz, CDCl$_3$) 30.6 (C(CH$_3$)$_2$), 33.8 (ArCH$_2$CH$_2$), 45.5 (N(CH$_3$)$_2$), 47.6 (N$^2$—CH$_2$), 61.5 (ArCH$_2$CH$_2$), 72.5 (C(CH$_3$)$_2$), 101.1, 116.2, 116.3, 119.1, 120.6, 129.0, 131.6, 136.1, 136.2, 138.9, 147.5, 156.4, 161.1, 161.3, 162.1, 165.9; MS[M+H]$^+$ m/z 474.4.

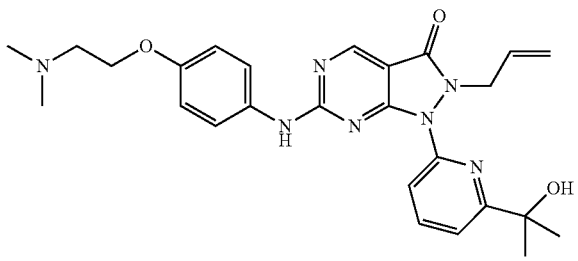 [SMILES: C=CCn1c(=O)c2cnc(Nc3ccc(OCCN(C)C)cc3)nc2n1-c1cccc(C(C)(C)O)n1]

Synthesis of 2-allyl-6-((4-(2-(dimethylamino) ethoxy)phenyl)amino)-1-(6-(2-hydroxypropan-2-yl) pyridin-2-yl)-1,2-dihydro-3H-pyrazolo[3,4-d]pyrimidin-3-one (CM-181)

2-Allyl-1-(6-(2-hydroxypropan-2-yl)pyridin-2-yl)-6-(methylthio)-1,2-dihydro-3H-pyrazolo[3,4-d]pyrimidin-3-one (0.102 g, 0.28 mmol), mCPBA (70% w/w, 78 mg, 0.31 mmol), 4-(2-(dimethylamino) ethoxy)aniline (67 mg, 0.37 mmol) and DIPEA (258 μL, 1.48 mmol) were reacted in toluene (3 mL) according to the described general procedure. Purification via silica gel chromatography (9:1 DCM: MeOH) afforded the target compound as an off-white solid (47 mg, 0.11 mmol, 38%). Rf 0.28 (9:1 DCM:MeOH); M.p. 123-126° C.; IR (cm$^{-1}$) 3248, 3081, 2976, 2937, 2870, 2821, 2773, 1680, 1614, 1512; $^1$H NMR (400 MHz, DMSO-d$_6$) 1.47 (6H, s, C(CH$_3$)$_2$), 2.28 (6H, s, N(CH$_3$)$_2$), 2.69 (2H, t, J=5.2 Hz, OCH$_2$CH$_2$), 4.06 (2H, t, J=5.2 Hz, OCH$_2$CH$_2$), 4.69 (2H, d$_{app}$, J=5.4 Hz, N$^2$—CH$_2$), 4.83 (1H, d$_{app}$, J=17.1 Hz, alkene C—H$^t$), 5.00 (1H, d$_{app}$, J=10.3 Hz, alkene C—H$^{cis}$), 5.33 (1H, s, OH), 5.67 (1H, ddt, J=17.1, 10.3, 5.4 Hz, alkene C—H), 6.94 (2H, d, J=8.4 Hz, H-3"/5"), 7.59-7.66 (3H, m, H-5'/2"/6"), 7.75 (1H, d$_{app}$, J=7.4 Hz, H-3'), 8.05 (1H, dd, J=7.8, 7.4 Hz, H-4'), 8.85 (1H, s, H-4), 10.19 (1H, br s, C$^6$—NH); $^{13}$C NMR (100 MHz, DMSO-d$_6$) 30.9 (C(CH$_3$)$_2$), 45.8 (N(CH$_3$)$_2$), 47.0 (N$^2$—CH$_2$), 58.1 (OCH$_2$CH$_2$), 66.2 (OCH$_2$CH$_2$), 72.8 (C(CH$_3$)$_2$), 114.8, 116.8, 118.7, 132.7, 139.3, 147.5, 154.9, 156.6, 161.6, 168.1; MS [M+H]$^+$ m/z 490.4.

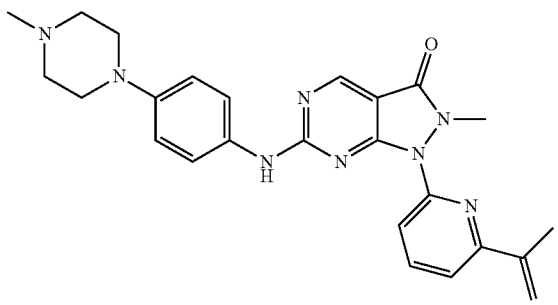 [SMILES: C=C(C)c1cccc(-n2c3nc(Nc4ccc(N5CCN(C)CC5)cc4)ncc3c(=O)n2C)n1]

Synthesis of 6-((4-(4-methylpiperazin-1-yl)phenyl) amino)-1-(6-(prop-1-en-2-yl)pyridin-2-yl)-1,2-dihydro-3H-pyrazolo[3,4-d]pyrimidin-3-one (CM-189)

1-(6-(2-Hydroxypropan-2-yl)pyridin-2-yl)-2-(4-methoxybenzyl)-6-((4-(4-methylpiperazin-1-yl)phenyl) amino)-1,2-dihydro-3H-pyrazolo[3,4-d]pyrimidin-3-one (56 mg, 0.10 mmol) was dissolved in TFA (2 mL) and the mixture was heated at reflux for 16 h. The solvent was removed in vacuo and the resultant residue was partitioned between EtOAc (10 mL) and saturated NaHCO$_3$ solution (10 mL). The organic phase was washed with brine (10 mL) and dried (MgSO$_4$) before being evaporated to dryness. Purification via silica gel chromatography (9:1 DCM:MeOH) afforded the target compound as a pale yellow solid (39 mg, 0.09 mmol, 91%). Rf 0.36 (9:1 DCM:MeOH); M.p. 260-270° C. (decomposed); IR (cm$^{-1}$) 3245, 3175, 2933, 2836, 2791, 1691, 1611; $^1$H NMR (400 MHz, DMSO-d$_6$) 2.20 (3H, s, CCH$_3$), 2.25 (3H, s, N—CH$_3$), 2.47-2.51 (4H, m, N—(CH$_2$CH$_2$)$_2$—NMe), 3.09-3.13 (4H, m, N—CH$_2$CH$_2$—NMe), 5.37 (1H, s, alkene C—H), 6.12 (1H, s, alkene C—H), 6.93 (2H, d, J=8.9 Hz, H-3"/5"), 7.45 (1H, d$_{app}$, J=7.5 Hz, H-3'), 7.67 (2H, d, J=8.9 Hz, H-2"/6"), 7.98 (1H, dd, J=7.8, 7.5 Hz, H-4'), 8.09-8.16 (1H, m, H-5'), 8.83 (1H, s, H-4), 9.88 (1H, s, C$^6$—NH), 11.95 (1H, br s, N$^2$—H); $^{13}$C NMR (100 MHz, DMSO-d$_6$) 20.7 (C(CH$_2$)CH$_3$), 46.1 (N—CH$_3$), 49.1 (piperazine-CH$_2$), 55.1 (piperazine-CH$_2$), 113.4, 116.2, 116.6, 117.3, 121.5, 132.1, 139.4, 142.5, 147.2, 154.7, 156.7, 157.4, 160.3; MS [M+H]$^+$ m/z 443.4.

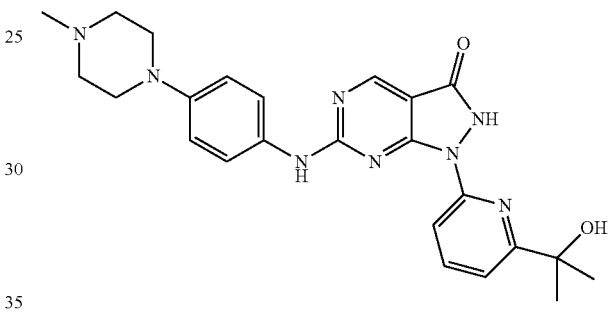

Synthesis of 1-(6-(2-hydroxypropan-2-yl)pyridin-2-yl)-6-((4-(4-methylpiperazin-1-yl)phenyl)amino)-1, 2-dihydro-3H-pyrazolo[3,4-d]pyrimidin-3-one (CM-235)

Sodium para-toluenesulfinate tetrahydrate (25 mg, 0.10 mmol) in MeOH (0.5 mL) was added to a solution of 2-allyl-1-(6-(2-hydroxypropan-2-yl)pyridin-2-yl)-6-((4-(4-methylpiperazin-1-yl)phenyl)amino)-1,2-dihydro-3H-pyrazolo[3,4-d]pyrimidin-3-one (AZD-1775, 50 mg, 0.10 mmol) and tetrakis(triphenylphosphine)palladium(0) (17 mg, 0.015 mmol) in THF (1 mL). The reaction mixture was stirred at RT for 2 hr before EtOAc (5 mL) was added and the resultant off-white precipitate was collected by filtration (36 mg, 0.08 mmol, 80%). Rf 0.21 (1:1 DCM:MeOH); M.p.>350° C.; IR (cm$^{-1}$) 3248, 3168, 2974, 2936, 2791, 1612, 1535; $^1$H NMR (400 MHz, DMSO-d$_6$) 1.52 (6H, s, C(CH$_3$)$_2$), 2.23 (3H, s, N—CH$_3$), 2.45-2.49 (4H, m, N—(CH$_2$CH$_2$)$_2$—NMe), 3.05-3.09 (4H, m, N—CH$_2$CH$_2$—NMe), 5.83 (1H, s, OH), 6.91 (2H, d, J=9.1 Hz, H-3"/5"), 7.19 (1H, d$_{app}$, J=7.5 Hz, H-5'), 7.69 (2H, d, J=9.1 Hz, H-2"/6"), 7.80 (1H, dd, J=7.9, 7.5 Hz, H-4'), 8.13 (1H, d$_{app}$, J=7.9 Hz, H-3'), 8.45 (1H, s, H-4), 9.23 (1H, s, C$^6$—NH); $^{13}$C NMR (100 MHz, DMSO-d$_6$) 31.2 (C(CH$_3$)$_2$), 46.3 (N—CH$_3$), 49.5 (piperazine-CH$_2$), 55.2 (piperazine-CH$_2$), 72.3 (C(CH$_3$)$_2$), 116.4, 120.5, 133.5, 138.6, 146.4, 150.5, 152.5, 159.1, 166.4; MS [M+H]$^+$ m/z 461.2.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. A compound having the chemical structure:

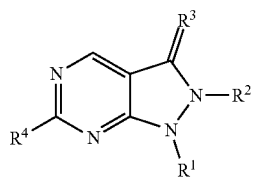

or a pharmaceutically acceptable salt thereof, wherein:
$R^1$ is 3-(2-hydroxypropan-2-yl) phenyl or 6-(2-hydroxypropan-2-yl) pyridin-2-yl;
$R^2$ is allyl, methyl, ethyl, propyl, isopropyl, butyl, or isobutyl;
$R^3$ is O;
$R^4$ is $NR^7R^8$;
$R^7$ and $R^8$ each are independently H or 4-(2 (dimethylamino) ethyl) phenyl); and wherein
$R^7$ and $R^8$ are not simultaneously H.

2. A compound being selected from:

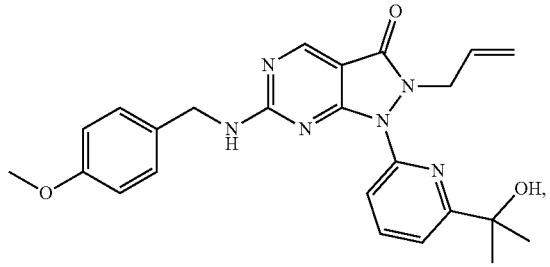

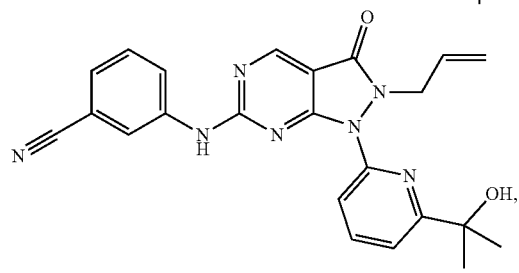

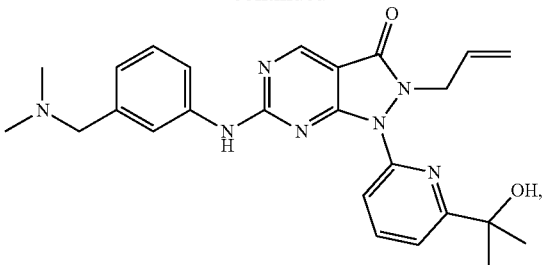

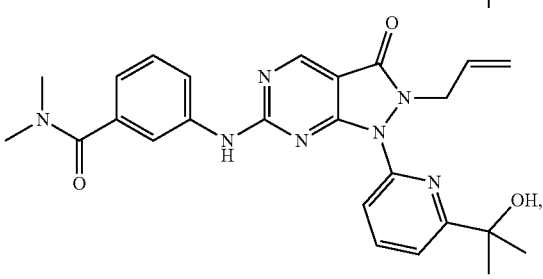

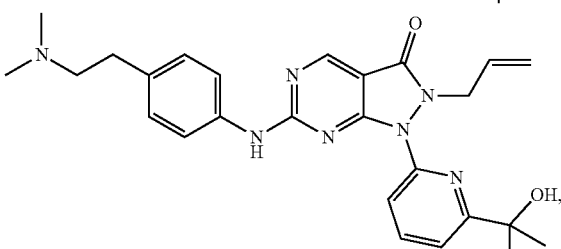

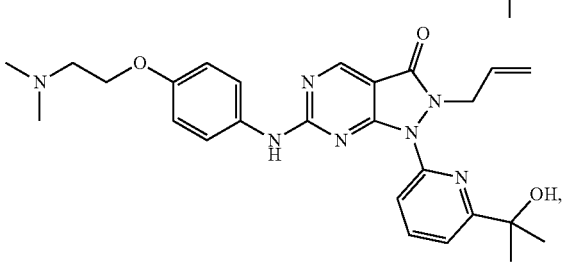

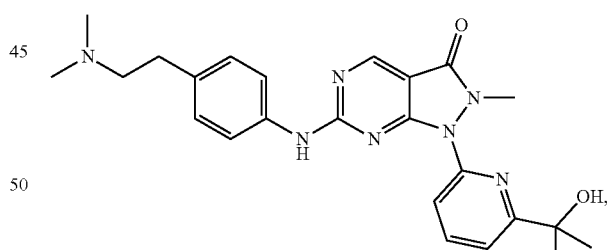

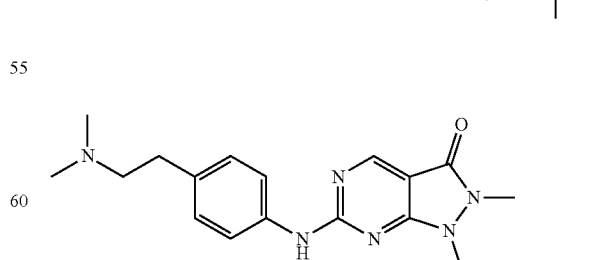

57
-continued
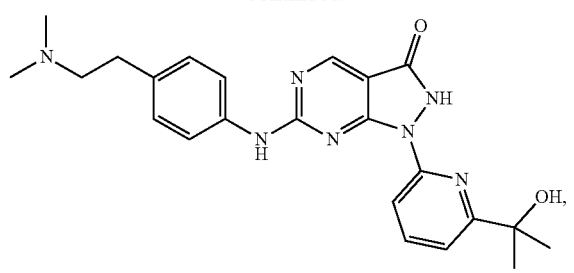
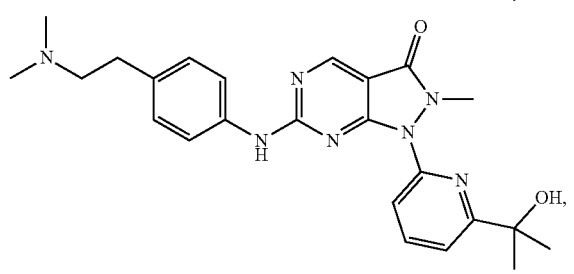
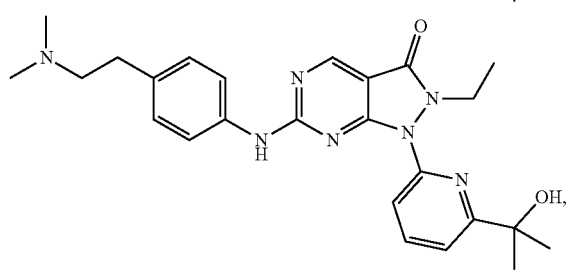
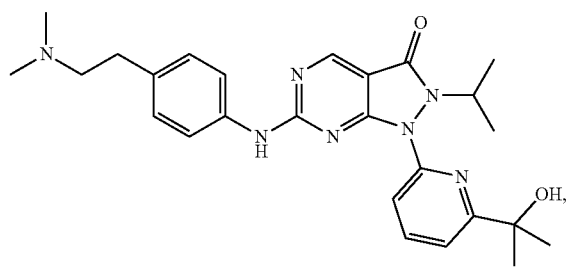
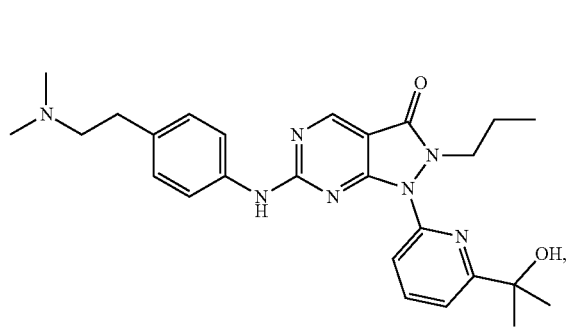
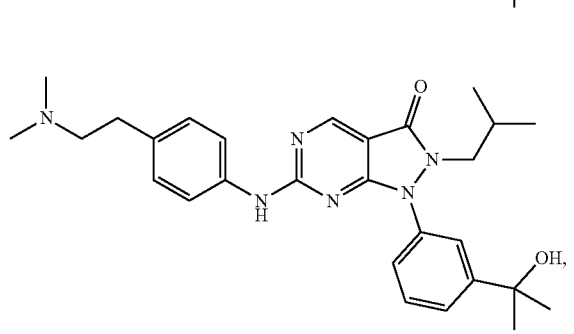
58
-continued
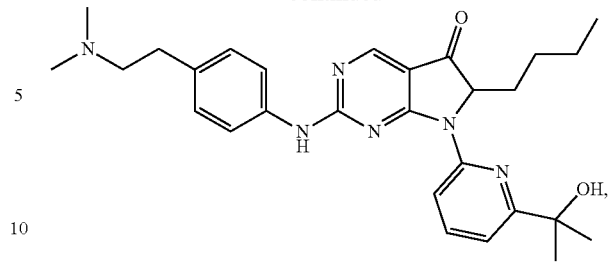
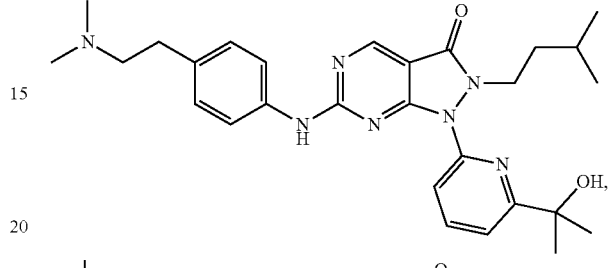
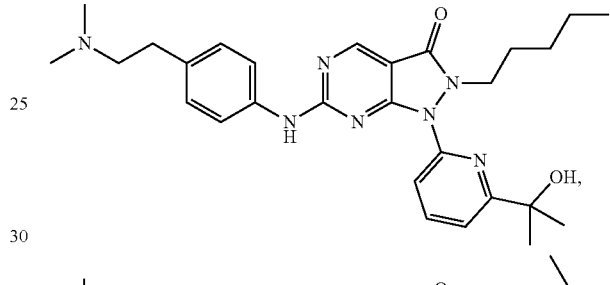
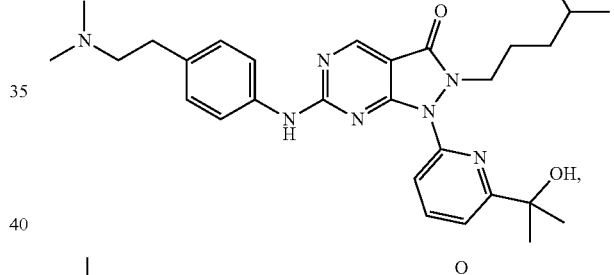
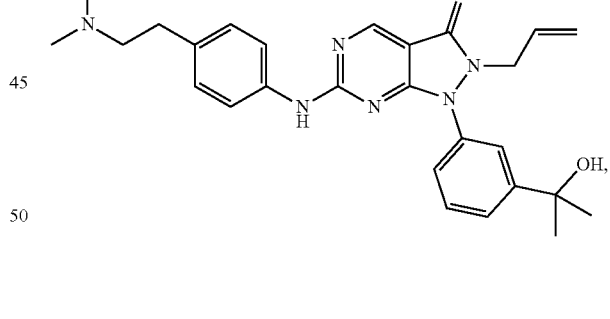
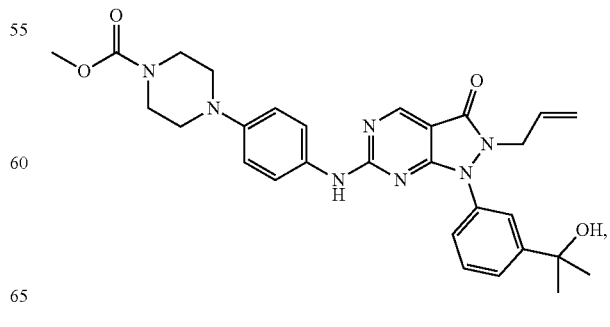

3. The compound of claim 2, being:
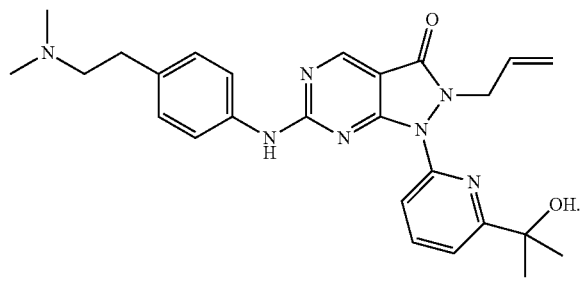 [SMILES: C=CCn1c(=O)c2cnc(Nc3ccc(CCN(C)C)cc3)nc2n1-c1cccc(C(C)(C)O)n1]
4. The compound of claim 2, being:
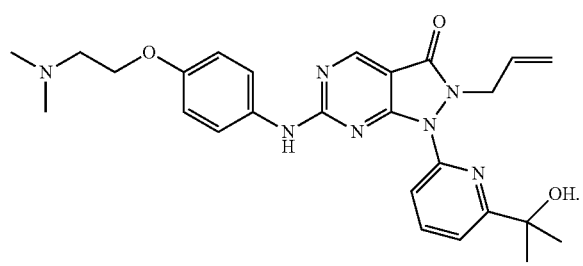 [SMILES: C=CCn1c(=O)c2cnc(Nc3ccc(OCCN(C)C)cc3)nc2n1-c1cccc(C(C)(C)O)n1]
5. The compound of claim 2, being:
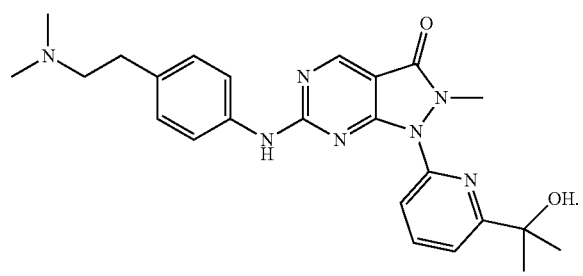 [SMILES: CN(C)CCc1ccc(Nc2ncc3c(=O)n(C)n(-c4cccc(C(C)(C)O)n4)c3n2)cc1]
6. The compound of claim 2, being:
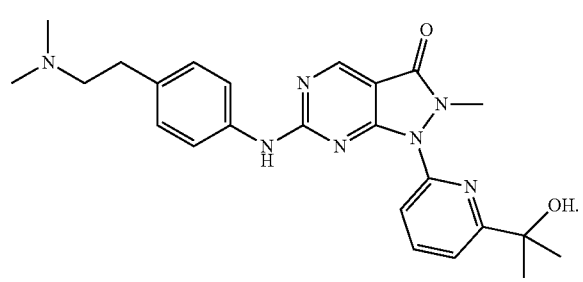 [SMILES: CN(C)CCc1ccc(Nc2ncc3c(=O)n(C)n(-c4cccc(C(C)(C)O)n4)c3n2)cc1]
7. The compound of claim 2, being:
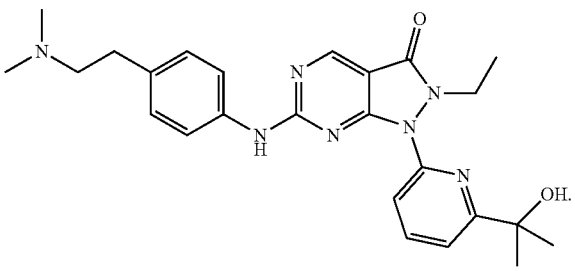 [SMILES: CCn1c(=O)c2cnc(Nc3ccc(CCN(C)C)cc3)nc2n1-c1cccc(C(C)(C)O)n1]
8. The compound of claim 2, being:
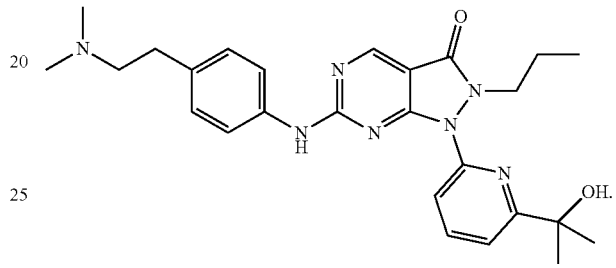
9. The compound of claim 2, being:
10. The compound of claim 2, being:
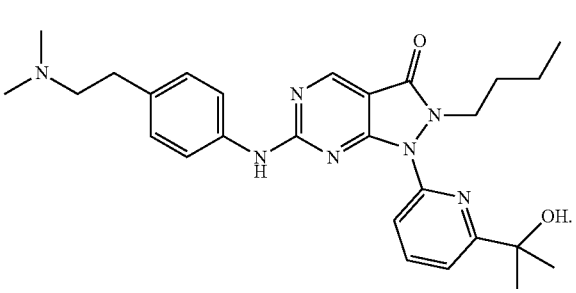 [SMILES: CCCCn1c(=O)c2cnc(Nc3ccc(CCN(C)C)cc3)nc2n1-c1cccc(C(C)(C)O)n1]

11. The compound of claim 2, being:
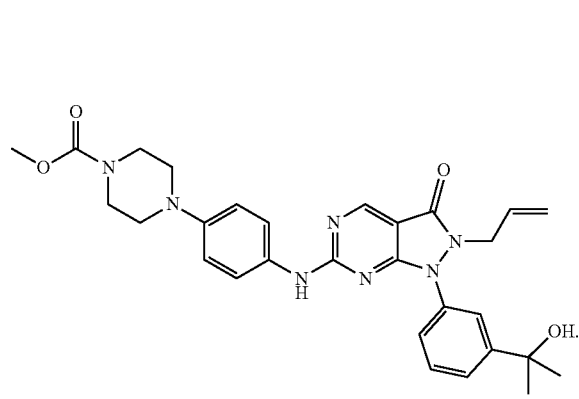 [SMILES: C=CCn1c(=O)c2cnc(Nc3ccc(N4CCN(C(=O)OC)CC4)cc3)nc2n1-c1cccc(C(C)(C)O)c1]
12. A pharmaceutical composition comprising the compound of claim 1, and at least one pharmaceutically acceptable additive.
13. A pharmaceutical kit containing the pharmaceutical composition of claim 12, prescribing information for the composition, and a container.
14. The compound of claim 2, being:
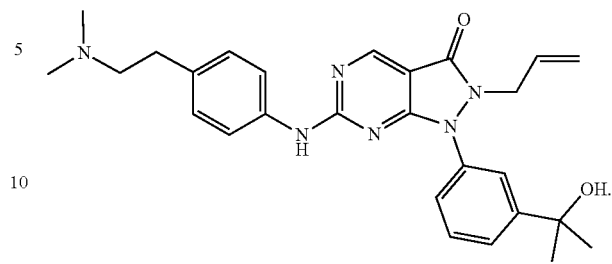
15. The compound of claim 2, being:
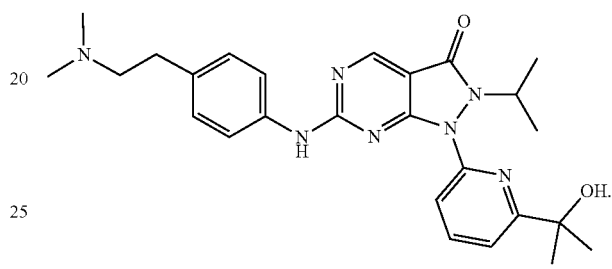
* * * * *